(12) United States Patent
Jonnavittula et al.

(10) Patent No.: US 10,960,343 B2
(45) Date of Patent: *Mar. 30, 2021

(54) METHODS AND SYSTEMS FOR PERFORMING CHEMICAL SEPARATIONS

(71) Applicant: Lummus Technology LLC, The Woodlands, CA (US)

(72) Inventors: Divya Jonnavittula, San Ramon, CA (US); Gaurav Chachra, Berkeley, CA (US); Guido Radaelli, Pleasant Hill, CA (US)

(73) Assignee: Lummus Technology LLC, The Woodlands, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 16/444,923

(22) Filed: Jun. 18, 2019

(65) Prior Publication Data

US 2020/0054983 A1 Feb. 20, 2020

Related U.S. Application Data

(63) Continuation of application No. 16/170,429, filed on Oct. 25, 2018, now abandoned, which is a (Continued)

(51) Int. Cl.
*C07C 2/84* (2006.01)
*C07C 7/12* (2006.01)
(Continued)

(52) U.S. Cl.
CPC ............ *B01D 53/047* (2013.01); *B01J 20/18* (2013.01); *B01J 20/226* (2013.01);
(Continued)

(58) Field of Classification Search
None
See application file for complete search history.

(56) References Cited

U.S. PATENT DOCUMENTS 2,324,172 A 7/1943 Parkhurst
2,486,980 A 11/1949 Robinson
(Continued)

FOREIGN PATENT DOCUMENTS

CA 2041874 C 4/1999
CA 2765769 A1 1/2011
(Continued)

OTHER PUBLICATIONS

Li, et al. Combined Single-Pass Conversion of Methane Via Oxidative Coupling and Dehydroaromatization. Catalysis Letters, Sep. 2003, vol. 89, Issue 3-4, pp. 275-279.
(Continued)

*Primary Examiner* — Philip Y Louie
(74) *Attorney, Agent, or Firm* — Calfee, Halter & Griswold LLP

(57) ABSTRACT

The present disclosure provides a method for generating higher hydrocarbon(s) from a stream comprising compounds with two or more carbon atoms ($C_{2+}$), comprising introducing methane and an oxidant (e.g., $O_2$) into an oxidative coupling of methane (OCM) reactor. The OCM reactor reacts the methane with the oxidant to generate a first product stream comprising the $C_{2+}$ compounds. The first product stream can then be directed to a separations unit that recovers at least a portion of the $C_{2+}$ compounds from the first product stream to yield a second product stream comprising the at least the portion of the $C_{2+}$ compounds.

18 Claims, 30 Drawing Sheets

Related U.S. Application Data continuation of application No. 15/476,889, filed on Mar. 31, 2017, now abandoned.

(60) Provisional application No. 62/436,312, filed on Dec. 19, 2016.

(51) Int. Cl.

| | | |
|---|---|---|
| *B01D 53/047* | (2006.01) | |
| *B01J 20/22* | (2006.01) | |
| *B01J 20/18* | (2006.01) | |
| *B01J 20/34* | (2006.01) | |
| *C01B 21/04* | (2006.01) | |
| *B01D 53/22* | (2006.01) | |

(52) U.S. Cl.
CPC ....... *B01J 20/3408* (2013.01); *B01J 20/3425* (2013.01); *B01J 20/3491* (2013.01); *C01B 21/0466* (2013.01); *C07C 2/84* (2013.01); *C07C 7/12* (2013.01); *B01D 53/228* (2013.01); *B01D 2253/108* (2013.01); *B01D 2253/204* (2013.01); *B01D 2256/12* (2013.01); *B01D 2256/24* (2013.01); *B01D 2257/102* (2013.01); *B01D 2257/104* (2013.01); *B01D 2257/108* (2013.01); *B01D 2257/502* (2013.01); *B01D 2257/504* (2013.01); *B01D 2257/702* (2013.01); *B01D 2257/7022* (2013.01); *B01D 2257/7025* (2013.01); *B01D 2259/40086* (2013.01); *B01D 2259/414* (2013.01); *C01B 2210/0018* (2013.01); *C01B 2210/0045* (2013.01); *Y02C 20/40* (2020.08)

(56) References Cited

U.S. PATENT DOCUMENTS

| | | |
|---|---|---|
| 2,577,701 A | 12/1951 | Deming et al. |
| 2,579,601 A | 12/1951 | Nelson et al. |
| 2,621,216 A | 12/1952 | White |
| 2,643,216 A | 6/1953 | Findlay |
| 2,673,221 A | 3/1954 | Schrader et al. |
| 2,880,592 A | 4/1959 | Davison et al. |
| 2,906,795 A * | 9/1959 | Ballard ............... C07C 9/16 585/304 |
| 2,926,751 A | 3/1960 | Kohl et al. |
| 2,943,125 A | 6/1960 | Ziegler et al. |
| 3,094,569 A | 6/1963 | Thomas |
| 3,128,317 A | 4/1964 | Arkell et al. |
| 3,325,556 A | 6/1967 | De Rosset |
| 3,413,817 A | 12/1968 | Kniel |
| 3,459,678 A | 8/1969 | Hagemeyer, Jr. et al. |
| 3,584,071 A | 6/1971 | McNulty et al. |
| 3,596,473 A | 8/1971 | Streich |
| 3,660,519 A | 5/1972 | Takaaki et al. |
| 3,686,334 A | 8/1972 | Britton |
| 3,686,350 A | 8/1972 | Ono et al. |
| 3,702,886 A | 11/1972 | Argauer et al. |
| 3,709,669 A | 1/1973 | Marion et al. |
| 3,751,878 A | 8/1973 | Collins |
| 3,754,052 A | 8/1973 | Hoffman et al. |
| 3,761,540 A | 9/1973 | Carter et al. |
| 3,862,257 A | 1/1975 | Buben et al. |
| 3,900,526 A | 8/1975 | Johnson et al. |
| 3,931,349 A | 1/1976 | Kuo |
| 3,966,644 A | 6/1976 | Gustafson |
| 3,994,983 A | 11/1976 | Webers et al. |
| 4,012,452 A | 3/1977 | Frampton |
| 4,090,949 A | 5/1978 | Owen et al. |
| 4,101,600 A | 7/1978 | Zhukov et al. |
| 4,107,224 A | 8/1978 | Dwyer |
| 4,126,645 A | 11/1978 | Collins |
| 4,132,745 A | 1/1979 | Amigues et al. |
| 4,140,504 A | 2/1979 | Campbell et al. |
| 4,211,885 A | 7/1980 | Banks |
| 4,232,177 A | 11/1980 | Smith, Jr. |
| 4,311,851 A | 1/1982 | Jung et al. |
| 4,314,090 A | 2/1982 | Shewbart et al. |
| 4,328,130 A | 5/1982 | Kyan |
| 4,329,530 A | 5/1982 | Irvine et al. |
| RE31,010 E | 8/1982 | Gelbein |
| 4,347,392 A | 8/1982 | Cosyns et al. |
| 4,367,353 A | 1/1983 | Inglis |
| 4,370,156 A | 1/1983 | Goddin, Jr. et al. |
| 4,375,566 A | 3/1983 | Kawamata et al. |
| 4,394,303 A | 7/1983 | Gibson |
| 4,433,185 A | 2/1984 | Tabak |
| 4,439,213 A | 3/1984 | Frey et al. |
| 4,440,956 A | 4/1984 | Couvillion |
| 4,465,887 A | 8/1984 | Schammel |
| 4,469,905 A | 9/1984 | Inwood et al. |
| 4,481,305 A | 11/1984 | Jorn et al. |
| 4,489,215 A | 12/1984 | Withers |
| 4,511,747 A | 4/1985 | Wright et al. |
| 4,551,438 A | 11/1985 | Miller |
| 4,552,644 A | 11/1985 | Johnson et al. |
| 4,554,395 A | 11/1985 | Jones et al. |
| 4,567,307 A | 1/1986 | Jones et al. |
| 4,605,488 A | 8/1986 | Chester et al. |
| 4,629,718 A | 12/1986 | Jones et al. |
| 4,673,664 A | 6/1987 | Bambrick |
| 4,717,782 A | 1/1988 | Garwood et al. |
| 4,751,336 A | 6/1988 | Jezl et al. |
| 4,754,091 A | 6/1988 | Jezl et al. |
| 4,754,093 A | 6/1988 | Jezl et al. |
| 4,769,047 A | 9/1988 | Dye |
| 4,777,313 A | 10/1988 | Sofranko et al. |
| 4,814,539 A | 3/1989 | Jezl et al. |
| 4,822,477 A | 4/1989 | Avidan et al. |
| 4,822,944 A | 4/1989 | Brazdil, Jr. et al. |
| 4,831,203 A | 5/1989 | Owen et al. |
| 4,835,331 A | 5/1989 | Hammershaimb et al. |
| 4,849,571 A | 7/1989 | Gaffney |
| 4,855,524 A | 8/1989 | Harandi et al. |
| 4,855,528 A | 8/1989 | Young et al. |
| 4,861,934 A | 8/1989 | Suzuki et al. |
| 4,865,820 A | 9/1989 | Dunster et al. |
| 4,882,400 A | 11/1989 | Dumain et al. |
| 4,891,457 A | 1/1990 | Owen et al. |
| 4,895,823 A | 1/1990 | Kolts et al. |
| 4,900,347 A | 2/1990 | McCue, Jr. et al. |
| 4,935,568 A | 6/1990 | Harandi et al. |
| 4,939,311 A | 7/1990 | Washecheck et al. |
| 4,939,312 A | 7/1990 | Baerns et al. |
| 4,950,311 A | 8/1990 | White, Jr. |
| 4,962,261 A | 10/1990 | Abrevaya et al. |
| 4,966,874 A | 10/1990 | Young et al. |
| 5,003,124 A | 3/1991 | Smith, Jr. et al. |
| 5,004,852 A | 4/1991 | Harandi |
| 5,012,028 A | 4/1991 | Gupta et al. |
| 5,015,799 A | 5/1991 | Walker et al. |
| 5,024,984 A | 6/1991 | Kaminsky et al. |
| 5,025,108 A | 6/1991 | Cameron et al. |
| 5,034,565 A | 7/1991 | Harandi et al. |
| 5,041,405 A | 8/1991 | Lunsford et al. |
| 5,055,627 A | 10/1991 | Smith, Jr. et al. |
| 5,057,468 A | 10/1991 | Adams |
| 5,057,638 A | 10/1991 | Sweeney |
| 5,066,629 A | 11/1991 | Lukey et al. |
| 5,080,872 A | 1/1992 | Jezl et al. |
| 5,082,819 A | 1/1992 | Boeck et al. |
| 5,118,898 A | 6/1992 | Tyler et al. |
| 5,132,472 A | 7/1992 | Durante et al. |
| 5,137,862 A | 8/1992 | Mackrodt et al. |
| 5,168,090 A | 12/1992 | Ebner et al. |
| 5,179,056 A | 1/1993 | Bartley |
| 5,196,634 A | 3/1993 | Washecheck et al. |
| 5,198,596 A | 3/1993 | Kaminsky et al. |
| 5,240,474 A | 8/1993 | Auvil et al. |
| 5,254,781 A | 10/1993 | Calamur et al. |
| 5,263,998 A | 11/1993 | Mackrodt et al. |
| 5,288,935 A | 2/1994 | Alario et al. |
| 5,292,979 A | 3/1994 | Chauvin et al. |

(56) References Cited

U.S. PATENT DOCUMENTS

| | | |
|---|---|---|
| 5,306,854 A | 4/1994 | Choudhary et al. |
| 5,312,795 A | 5/1994 | Kaminsky et al. |
| 5,316,995 A | 5/1994 | Kaminsky et al. |
| 5,326,915 A | 7/1994 | Viola et al. |
| 5,328,883 A | 7/1994 | Washecheck et al. |
| 5,336,825 A | 8/1994 | Choudhary et al. |
| 5,336,826 A | 8/1994 | Brophy et al. |
| 5,345,023 A | 9/1994 | Chauvin et al. |
| 5,348,642 A | 9/1994 | Serrand et al. |
| 5,371,306 A | 12/1994 | Woo et al. |
| 5,395,981 A | 3/1995 | Marker |
| 5,414,157 A | 5/1995 | Durante et al. |
| 5,414,170 A | 5/1995 | McCue et al. |
| 5,430,219 A | 7/1995 | Sanfilippo et al. |
| 5,449,850 A | 9/1995 | Young et al. |
| 5,462,583 A | 10/1995 | Wood et al. |
| 5,473,027 A | 12/1995 | Batchelor et al. |
| 5,500,149 A | 3/1996 | Green et al. |
| 5,523,493 A | 6/1996 | Cameron et al. |
| 5,568,737 A | 10/1996 | Campbell et al. |
| 5,599,510 A | 2/1997 | Kaminsky et al. |
| 5,633,422 A | 5/1997 | Murray |
| 5,659,090 A | 8/1997 | Cameron et al. |
| 5,670,442 A | 9/1997 | Fornasari et al. |
| RE35,632 E | 10/1997 | Leyshon |
| RE35,633 E | 10/1997 | Leyshon |
| 5,679,241 A | 10/1997 | Stanley et al. |
| 5,702,589 A | 12/1997 | Tsang et al. |
| 5,712,217 A | 1/1998 | Choudhary et al. |
| 5,714,657 A | 2/1998 | deVries |
| 5,723,713 A | 3/1998 | Maunders |
| 5,736,107 A | 4/1998 | Inomata et al. |
| 5,744,015 A | 4/1998 | Mazanec et al. |
| 5,749,937 A | 5/1998 | Detering et al. |
| 5,750,821 A | 5/1998 | Inomata et al. |
| 5,763,722 A | 6/1998 | Vic et al. |
| 5,792,895 A | 8/1998 | Commereuc et al. |
| 5,811,618 A | 9/1998 | Wu |
| 5,811,619 A | 9/1998 | Commereuc et al. |
| 5,817,904 A | 10/1998 | Vic et al. |
| 5,817,905 A | 10/1998 | Commereuc et al. |
| 5,819,555 A | 10/1998 | Engdahl |
| 5,830,822 A | 11/1998 | Euzen |
| 5,849,973 A | 12/1998 | Van Der Vaart |
| 5,856,257 A | 1/1999 | Freeman et al. |
| 5,861,353 A | 1/1999 | Viola et al. |
| 5,866,737 A | 2/1999 | Hagemeyer et al. |
| 5,877,363 A | 3/1999 | Gildert et al. |
| 5,877,368 A | 3/1999 | Kiyama et al. |
| 5,897,945 A | 4/1999 | Lieber et al. |
| 5,917,136 A | 6/1999 | Gaffney et al. |
| 5,935,293 A | 8/1999 | Detering et al. |
| 5,935,897 A | 8/1999 | Truebenbach et al. |
| 5,935,898 A | 8/1999 | Truebenbach et al. |
| 5,936,135 A | 8/1999 | Choudhary et al. |
| 5,959,170 A | 9/1999 | Withers, Jr. |
| 6,005,121 A | 12/1999 | Ebner et al. |
| 6,013,851 A | 1/2000 | Verrelst et al. |
| 6,020,533 A | 2/2000 | Lewis et al. |
| 6,030,598 A | 2/2000 | Topham et al. |
| 6,031,145 A | 2/2000 | Commereuc et al. |
| 6,087,545 A | 7/2000 | Choudhary et al. |
| 6,096,934 A | 8/2000 | Rekoske |
| 6,103,654 A | 8/2000 | Commereuc et al. |
| 6,110,979 A | 8/2000 | Nataraj et al. |
| 6,114,400 A | 9/2000 | Nataraj et al. |
| 6,140,535 A | 10/2000 | Williams |
| 6,146,549 A | 11/2000 | Mackay et al. |
| 6,153,149 A | 11/2000 | Rabitz et al. |
| 6,221,986 B1 | 4/2001 | Commereuc et al. |
| 6,328,945 B1 | 12/2001 | Hufton et al. |
| 6,342,149 B1 | 1/2002 | Koster et al. |
| 6,355,093 B1 | 3/2002 | Schwartz et al. |
| 6,380,451 B1 | 4/2002 | Kreischer et al. |
| 6,403,523 B1 | 6/2002 | Cantrell et al. |
| RE37,853 E | 9/2002 | Detering et al. |
| 6,444,869 B2 | 9/2002 | Senetar et al. |
| 6,447,745 B1 | 9/2002 | Feeley et al. |
| 6,455,015 B1 | 9/2002 | Kilroy |
| 6,468,501 B1 | 10/2002 | Chen et al. |
| 6,486,373 B1 | 11/2002 | Abichandani et al. |
| 6,492,571 B1 | 12/2002 | He et al. |
| 6,509,292 B1 | 1/2003 | Blankenship et al. |
| 6,518,220 B2 | 2/2003 | Walsdorff et al. |
| 6,518,476 B1 | 2/2003 | Culp et al. |
| 6,538,169 B1 | 3/2003 | Pittman et al. |
| 6,576,803 B2 | 6/2003 | Cantrell et al. |
| 6,596,912 B1 | 7/2003 | Lunsford et al. |
| 6,610,124 B1 | 8/2003 | Dolan et al. |
| 6,660,812 B2 | 12/2003 | Kuechler et al. |
| 6,660,894 B1 | 12/2003 | Wu et al. |
| 6,683,019 B2 | 1/2004 | Gartside et al. |
| 6,703,429 B2 | 3/2004 | O'Rear et al. |
| 6,713,657 B2 | 3/2004 | O'Rear et al. |
| 6,726,832 B1 | 4/2004 | Baldassari et al. |
| 6,726,850 B1 | 4/2004 | Reyes et al. |
| 6,730,808 B2 | 5/2004 | Bitterlich et al. |
| 6,747,066 B2 | 6/2004 | Wang et al. |
| 6,759,562 B2 | 7/2004 | Gartside et al. |
| 6,761,838 B2 | 7/2004 | Zeng et al. |
| 6,764,602 B2 | 7/2004 | Shutt et al. |
| 6,768,035 B2 | 7/2004 | O'Rear et al. |
| 6,821,500 B2 | 11/2004 | Fincke et al. |
| 6,841,708 B1 | 1/2005 | Benje |
| 6,891,001 B2 | 5/2005 | Kuhlburger |
| 6,914,165 B2 | 7/2005 | Flego et al. |
| 6,964,934 B2 | 11/2005 | Brady et al. |
| 7,093,445 B2 | 8/2006 | Corr, II et al. |
| 7,105,147 B2 | 9/2006 | Kurimura et al. |
| 7,129,195 B2 | 10/2006 | Felder et al. |
| 7,157,612 B2 | 1/2007 | Ewert et al. |
| 7,164,052 B2 | 1/2007 | Carati et al. |
| 7,176,342 B2 | 2/2007 | Bellussi et al. |
| 7,183,451 B2 | 2/2007 | Gattis et al. |
| 7,196,238 B2 | 3/2007 | Nurminen et al. |
| 7,199,273 B2 | 4/2007 | Molinier et al. |
| 7,208,647 B2 | 4/2007 | Peterson et al. |
| 7,214,841 B2 | 5/2007 | Gartside et al. |
| 7,250,543 B2 | 7/2007 | Bagherzadeh et al. |
| 7,291,321 B2 | 11/2007 | Bagherzadeh et al. |
| 7,316,804 B2 | 1/2008 | Taheri et al. |
| 7,361,622 B2 | 4/2008 | Benderly et al. |
| 7,473,814 B2 | 1/2009 | Basset et al. |
| 7,485,595 B2 | 2/2009 | Long et al. |
| 7,525,002 B2 | 4/2009 | Umansky et al. |
| 7,547,813 B2 | 6/2009 | Smith et al. |
| 7,550,644 B2 | 6/2009 | Pfefferle |
| 7,566,428 B2 | 7/2009 | Warner et al. |
| 7,576,296 B2 | 8/2009 | Fincke et al. |
| 7,579,509 B2 | 8/2009 | Benje et al. |
| 7,589,246 B2 | 9/2009 | Iaccino et al. |
| 7,659,437 B2 | 2/2010 | Iaccino et al. |
| 7,663,011 B2 | 2/2010 | Shan et al. |
| 7,667,085 B2 | 2/2010 | Gattis et al. |
| 7,671,244 B2 | 3/2010 | Hafenscher et al. |
| 7,683,227 B2 | 3/2010 | Iaccino et al. |
| 7,687,041 B2 | 3/2010 | Singh |
| 7,687,048 B1 | 3/2010 | Schultz et al. |
| 7,728,186 B2 | 6/2010 | Iaccino et al. |
| 7,781,636 B2 | 8/2010 | Iaccino et al. |
| 7,790,012 B2 | 9/2010 | Kirk et al. |
| 7,790,776 B2 | 9/2010 | Christensen et al. |
| 7,795,490 B2 | 9/2010 | Iaccino et al. |
| 7,799,209 B2 | 9/2010 | Petri |
| 7,799,730 B2 | 9/2010 | Ringer et al. |
| 7,838,710 B2 | 11/2010 | Ryu |
| 7,868,216 B2 | 1/2011 | Chodorge et al. |
| 7,879,119 B2 | 2/2011 | Abughazaleh et al. |
| 7,888,541 B2 | 2/2011 | Gartside et al. |
| 7,888,543 B2 | 2/2011 | Iaccino et al. |
| 7,902,113 B2 | 3/2011 | Zarrinpashne et al. |
| 7,915,461 B2 | 3/2011 | Gattis et al. |
| 7,915,462 B2 | 3/2011 | Gattis et al. |
| 7,915,463 B2 | 3/2011 | Gattis et al. |

(56) References Cited

U.S. PATENT DOCUMENTS

| | | |
|---|---|---|
| 7,915,464 B2 | 3/2011 | Gattis et al. |
| 7,915,465 B2 | 3/2011 | Gattis et al. |
| 7,915,466 B2 | 3/2011 | Gattis et al. |
| 7,932,296 B2 | 4/2011 | Malhotra et al. |
| 7,968,020 B2 | 6/2011 | Behelfer et al. |
| 7,968,759 B2 | 6/2011 | Iaccino et al. |
| 7,977,519 B2 | 7/2011 | Iaccino et al. |
| 7,993,500 B2 | 8/2011 | Gilliam et al. |
| 7,993,599 B2 | 8/2011 | Leveson |
| 8,021,620 B2 | 9/2011 | Nicholas et al. |
| 8,071,836 B2 | 12/2011 | Butler |
| 8,080,215 B2 | 12/2011 | Taheri et al. |
| 8,119,848 B2 | 2/2012 | Cross, Jr. et al. |
| 8,129,305 B2 | 3/2012 | Bagherzadeh et al. |
| 8,137,444 B2 | 3/2012 | Farsad et al. |
| 8,153,851 B2 | 4/2012 | Gartside et al. |
| 8,163,070 B2 | 4/2012 | Hees et al. |
| 8,192,709 B2 | 6/2012 | Reyes et al. |
| 8,227,650 B2 | 7/2012 | Putman et al. |
| 8,232,415 B2 | 7/2012 | Taheri et al. |
| 8,258,358 B2 | 9/2012 | Gartside et al. |
| 8,269,055 B2 | 9/2012 | Fritz et al. |
| 8,277,525 B2 | 10/2012 | Dalton |
| 8,293,805 B2 | 10/2012 | Khan et al. |
| 8,399,527 B1 | 3/2013 | Brown et al. |
| 8,399,726 B2 | 3/2013 | Chinta et al. |
| 8,404,189 B2 | 3/2013 | Andresen et al. |
| 8,435,920 B2 | 5/2013 | White et al. |
| 8,450,546 B2 | 5/2013 | Chinta et al. |
| 8,524,625 B2 | 9/2013 | Dight et al. |
| 8,552,236 B2 | 10/2013 | Iaccino |
| 8,557,728 B2 | 10/2013 | Birdsall et al. |
| 8,575,410 B2 | 11/2013 | Nicholas et al. |
| 8,624,042 B2 | 1/2014 | Grasset et al. |
| 8,658,750 B2 | 2/2014 | Lattner et al. |
| 8,669,171 B2 | 3/2014 | Perraud et al. |
| 8,710,286 B2 | 4/2014 | Butler |
| 8,729,328 B2 | 5/2014 | Chinta et al. |
| 8,742,189 B2 | 6/2014 | Kiesslich et al. |
| 8,742,192 B2 | 6/2014 | Godsmark et al. |
| 8,748,681 B2 | 6/2014 | Nicholas et al. |
| 8,748,682 B2 | 6/2014 | Nicholas et al. |
| 8,759,598 B2 | 6/2014 | Hayashi et al. |
| 8,765,660 B1 | 7/2014 | Li et al. |
| 8,796,497 B2 | 8/2014 | Chinta et al. |
| 8,865,780 B2 | 10/2014 | Bogild Hansen |
| 8,912,109 B2 | 12/2014 | Chinta et al. |
| 8,912,381 B2 | 12/2014 | Chinta et al. |
| 8,921,256 B2 | 12/2014 | Cizeron et al. |
| 8,962,517 B2 | 2/2015 | Zurcher et al. |
| 8,993,473 B2 | 3/2015 | Melde et al. |
| 9,040,762 B2 | 5/2015 | Cizeron et al. |
| 9,079,815 B2 | 7/2015 | Mukherjee et al. |
| 9,133,079 B2 | 9/2015 | Weinberger et al. |
| 9,321,702 B2 | 4/2016 | Nyce et al. |
| 9,321,703 B2 | 4/2016 | Nyce et al. |
| 9,328,297 B1 | 5/2016 | Nyce et al. |
| 9,334,204 B1 | 5/2016 | Radaelli et al. |
| 9,352,295 B2 | 5/2016 | Rafique et al. |
| 9,371,257 B2 | 6/2016 | Chinta et al. |
| 9,376,324 B2 | 6/2016 | Senderov et al. |
| 9,446,343 B2 | 9/2016 | Elliott et al. |
| 9,446,397 B2 | 9/2016 | Gamoras et al. |
| 9,469,577 B2 | 10/2016 | Schammel et al. |
| 9,512,047 B2 | 12/2016 | Nyce et al. |
| 9,527,784 B2 | 12/2016 | Weinberger et al. |
| 9,556,086 B2 | 1/2017 | Schammel et al. |
| 9,567,269 B2 | 2/2017 | Radaelli et al. |
| 9,598,328 B2 | 3/2017 | Nyce et al. |
| 9,670,113 B2 | 6/2017 | Iyer et al. |
| 9,682,900 B2 | 6/2017 | Keusenkothen et al. |
| 9,701,597 B2 | 7/2017 | Rafique et al. |
| 9,718,054 B2 | 8/2017 | Scher et al. |
| 9,738,571 B2 | 8/2017 | Schammel et al. |
| 9,751,079 B2 | 9/2017 | Freer et al. |
| 9,751,818 B2 | 9/2017 | Zurcher et al. |
| 9,790,144 B2 | 10/2017 | Radaelli et al. |
| 9,944,573 B2 | 4/2018 | Radaelli et al. |
| 9,950,971 B2 | 4/2018 | Henao et al. |
| 9,956,544 B2 | 5/2018 | Schammel et al. |
| 9,969,660 B2 | 5/2018 | Iyer et al. |
| 9,975,767 B2 | 5/2018 | Farnell |
| 10,047,020 B2 | 8/2018 | Cizeron et al. |
| 10,195,603 B2 | 2/2019 | Scher et al. |
| 10,300,465 B2 | 5/2019 | Freer et al. |
| 10,301,234 B2 | 5/2019 | Nyce et al. |
| 10,308,565 B2 | 6/2019 | Schammel et al. |
| 10,377,682 B2 | 8/2019 | Rafique et al. |
| 10,407,361 B2 | 9/2019 | Radaelli et al. |
| 10,787,398 B2 | 9/2020 | Nyce et al. |
| 10,787,400 B2 | 9/2020 | Radaelli et al. |
| 10,793,490 B2 | 10/2020 | Radaelli et al. |
| 2002/0007101 A1 | 1/2002 | Senetar et al. |
| 2002/0015670 A1 | 2/2002 | Shah et al. |
| 2002/0150522 A1 | 10/2002 | Heim et al. |
| 2002/0182735 A1 | 12/2002 | Kibby et al. |
| 2003/0033932 A1 | 2/2003 | Sirkar et al. |
| 2003/0045761 A1 | 3/2003 | Kuechler et al. |
| 2003/0072700 A1 | 4/2003 | Goebel et al. |
| 2003/0094398 A1 | 5/2003 | Porter et al. |
| 2003/0189202 A1 | 10/2003 | Li et al. |
| 2003/0233019 A1 | 12/2003 | Sherwood |
| 2004/0158113 A1 | 8/2004 | Srinivas et al. |
| 2004/0220053 A1 | 11/2004 | Bagherzadeh et al. |
| 2004/0231586 A1 | 11/2004 | Dugue et al. |
| 2004/0242940 A1 | 12/2004 | Takahashi et al. |
| 2005/0065391 A1 | 3/2005 | Gattis et al. |
| 2005/0065392 A1 | 3/2005 | Peterson et al. |
| 2005/0107650 A1 | 5/2005 | Sumner |
| 2005/0154228 A1 | 7/2005 | Nakajima et al. |
| 2005/0239634 A1 | 10/2005 | Ying et al. |
| 2006/0018821 A1 | 1/2006 | Suzuki et al. |
| 2006/0063955 A1 | 3/2006 | Lacombe et al. |
| 2006/0155157 A1 | 7/2006 | Zarrinpashne et al. |
| 2006/0194995 A1 | 8/2006 | Umansky et al. |
| 2006/0235246 A1 | 10/2006 | Smith et al. |
| 2006/0283780 A1 | 12/2006 | Spivey et al. |
| 2007/0027030 A1 | 2/2007 | Cheung et al. |
| 2007/0073083 A1 | 3/2007 | Sunley |
| 2007/0083073 A1 | 4/2007 | Bagherzadeh et al. |
| 2007/0112236 A1 | 5/2007 | Bridges et al. |
| 2007/0135668 A1 | 6/2007 | Sumner |
| 2007/0244347 A1 | 10/2007 | Ying et al. |
| 2008/0121383 A1 | 5/2008 | Birk |
| 2008/0138274 A1 | 6/2008 | Garcia-Martinez |
| 2008/0141713 A1 | 6/2008 | Verma |
| 2008/0154078 A1 | 6/2008 | Bozzano et al. |
| 2008/0267852 A1 | 10/2008 | Schumacher et al. |
| 2008/0275143 A1 | 11/2008 | Malhotra et al. |
| 2008/0281136 A1 | 11/2008 | Bagherzadeh et al. |
| 2008/0293980 A1 | 11/2008 | Kiesslich et al. |
| 2008/0300436 A1 | 12/2008 | Cheung et al. |
| 2009/0005236 A1 | 1/2009 | Ying et al. |
| 2009/0042998 A1 | 2/2009 | Hashimoto et al. |
| 2009/0043141 A1 | 2/2009 | Mazanec et al. |
| 2009/0087496 A1 | 4/2009 | Katusic et al. |
| 2009/0110631 A1 | 4/2009 | Garcia-Martinez et al. |
| 2009/0202427 A1 | 8/2009 | Katusic et al. |
| 2009/0203946 A1 | 8/2009 | Chuang |
| 2009/0209412 A1 | 8/2009 | Parent et al. |
| 2009/0209794 A1 | 8/2009 | Lauritzen et al. |
| 2009/0216059 A1 | 8/2009 | Reyes et al. |
| 2009/0259076 A1 | 10/2009 | Simmons et al. |
| 2009/0264693 A1 | 10/2009 | Xie et al. |
| 2009/0267852 A1 | 10/2009 | Tahmisian, Jr. et al. |
| 2009/0277837 A1 | 11/2009 | Liu et al. |
| 2009/0312583 A1 | 12/2009 | Sigl et al. |
| 2010/0000153 A1 | 1/2010 | Kurkjian et al. |
| 2010/0003179 A1 | 1/2010 | Katusic et al. |
| 2010/0028735 A1 | 2/2010 | Basset et al. |
| 2010/0185034 A1 | 7/2010 | Nishimura et al. |
| 2010/0191031 A1 | 7/2010 | Sundaram |
| 2010/0197482 A1 | 8/2010 | Basset et al. |
| 2010/0197986 A1 | 8/2010 | Midorikawa et al. |

(56) References Cited

U.S. PATENT DOCUMENTS

| | | |
|---|---|---|
| 2010/0222203 A1 | 9/2010 | Baba et al. |
| 2010/0249473 A1 | 9/2010 | Butler |
| 2010/0331174 A1 | 12/2010 | Chinta et al. |
| 2010/0331593 A1 | 12/2010 | Chinta et al. |
| 2010/0331595 A1 | 12/2010 | Chinta et al. |
| 2011/0036728 A1 | 2/2011 | Farsad |
| 2011/0049132 A1 | 3/2011 | Lee |
| 2011/0052466 A1 | 3/2011 | Liu |
| 2011/0071331 A1 | 3/2011 | Basset et al. |
| 2011/0124488 A1 | 5/2011 | Meitner et al. |
| 2011/0160508 A1 | 6/2011 | Ma et al. |
| 2011/0171121 A1 | 7/2011 | Senderov et al. |
| 2011/0189559 A1 | 8/2011 | De Miranda et al. |
| 2011/0230690 A1 | 9/2011 | Tiita et al. |
| 2011/0240926 A1 | 10/2011 | Schellen et al. |
| 2011/0257453 A1 | 10/2011 | Chinta et al. |
| 2011/0257454 A1 | 10/2011 | Thorman et al. |
| 2011/0263917 A1 | 10/2011 | Van Hal et al. |
| 2011/0315012 A1 | 12/2011 | Kuznicki et al. |
| 2012/0006054 A1 | 1/2012 | Keller |
| 2012/0041246 A1 | 2/2012 | Scher et al. |
| 2012/0065412 A1 | 3/2012 | Abdallah et al. |
| 2012/0095275 A1 | 4/2012 | Coleman et al. |
| 2012/0129690 A1 | 5/2012 | Larcher et al. |
| 2012/0172648 A1 | 7/2012 | Seebauer |
| 2012/0197053 A1 | 8/2012 | Cantrell et al. |
| 2012/0198769 A1 | 8/2012 | Schirrmeister et al. |
| 2012/0202986 A1 | 8/2012 | Hassan et al. |
| 2012/0204716 A1 | 8/2012 | Schirrmeister et al. |
| 2012/0215045 A1 | 8/2012 | Butler |
| 2012/0222422 A1 | 9/2012 | Nunley et al. |
| 2012/0258852 A1 | 10/2012 | Martinez et al. |
| 2012/0277474 A1 | 11/2012 | Graham Ronald et al. |
| 2013/0023708 A1 | 1/2013 | Majumder et al. |
| 2013/0023709 A1 | 1/2013 | Cizeron et al. |
| 2013/0025201 A1 | 1/2013 | Dalton |
| 2013/0040806 A1 | 2/2013 | Dismukes et al. |
| 2013/0042480 A1 | 2/2013 | Turulin |
| 2013/0142707 A1 | 6/2013 | Chinta et al. |
| 2013/0158322 A1 | 6/2013 | Nyce et al. |
| 2013/0165728 A1 | 6/2013 | Zurcher et al. |
| 2013/0172649 A1 | 7/2013 | Chinta et al. |
| 2013/0178680 A1 | 7/2013 | Ha et al. |
| 2013/0183231 A1 | 7/2013 | Senderov et al. |
| 2013/0225880 A1 | 8/2013 | Brown et al. |
| 2013/0225884 A1 | 8/2013 | Weinberger et al. |
| 2013/0253248 A1 | 9/2013 | Gamoras et al. |
| 2013/0270180 A1 | 10/2013 | Zhang et al. |
| 2013/0289324 A1 | 10/2013 | Price et al. |
| 2013/0291720 A1 | 11/2013 | Blood et al. |
| 2013/0292300 A1 | 11/2013 | Ying et al. |
| 2014/0012053 A1 | 1/2014 | Iyer et al. |
| 2014/0018589 A1 | 1/2014 | Iyer et al. |
| 2014/0061540 A1 | 3/2014 | Long et al. |
| 2014/0080699 A1 | 3/2014 | Ghose et al. |
| 2014/0107385 A1 | 4/2014 | Schammel et al. |
| 2014/0121433 A1 | 5/2014 | Cizeron et al. |
| 2014/0128484 A1 | 5/2014 | Hassan et al. |
| 2014/0128485 A1 | 5/2014 | Hassan et al. |
| 2014/0135552 A1 | 5/2014 | Nicholas et al. |
| 2014/0135553 A1 | 5/2014 | Nicholas et al. |
| 2014/0135554 A1 | 5/2014 | Nicholas et al. |
| 2014/0171707 A1 | 6/2014 | Nyce et al. |
| 2014/0181877 A1 | 6/2014 | Haykinson et al. |
| 2014/0194663 A1 | 7/2014 | Butler |
| 2014/0194664 A1 | 7/2014 | Sawyer et al. |
| 2014/0235911 A1 | 8/2014 | Laha |
| 2014/0249339 A1 | 9/2014 | Simanzhenkov et al. |
| 2014/0274671 A1 | 9/2014 | Schammel et al. |
| 2014/0275619 A1 | 9/2014 | Chen et al. |
| 2014/0377137 A1 | 12/2014 | Mignon et al. |
| 2014/0378728 A1 | 12/2014 | Davis et al. |
| 2015/0010467 A1 | 1/2015 | Ito et al. |
| 2015/0038750 A1 | 2/2015 | Weiss et al. |
| 2015/0045599 A1 | 2/2015 | Frey et al. |
| 2015/0065767 A1* | 3/2015 | Henao .................. B01J 15/005 585/300 |
| 2015/0099914 A1 | 4/2015 | Garza et al. |
| 2015/0152025 A1* | 6/2015 | Cizeron .................. C07C 2/84 585/324 |
| 2015/0210610 A1* | 7/2015 | Rafique .................. C07C 2/84 585/315 |
| 2015/0218786 A1 | 8/2015 | Cullen |
| 2015/0232395 A1 | 8/2015 | Nyce et al. |
| 2015/0307415 A1 | 10/2015 | Rafique et al. |
| 2015/0314267 A1 | 11/2015 | Schammel et al. |
| 2015/0321974 A1 | 11/2015 | Schammel et al. |
| 2015/0329438 A1 | 11/2015 | Nyce et al. |
| 2015/0329439 A1 | 11/2015 | Nyce et al. |
| 2015/0368167 A1 | 12/2015 | Weinberger et al. |
| 2015/0376527 A1 | 12/2015 | Xu |
| 2016/0074844 A1 | 3/2016 | Freer et al. |
| 2016/0089637 A1 | 3/2016 | Chang et al. |
| 2016/0167973 A1 | 6/2016 | Boorse et al. |
| 2016/0200643 A1 | 7/2016 | Nyce et al. |
| 2016/0237003 A1 | 8/2016 | Mammadov et al. |
| 2016/0250618 A1 | 9/2016 | Long et al. |
| 2016/0272556 A1 | 9/2016 | Rafique et al. |
| 2016/0272557 A1 | 9/2016 | Radaelli et al. |
| 2016/0289143 A1 | 10/2016 | Duggal et al. |
| 2016/0318828 A1 | 11/2016 | Washburn et al. |
| 2016/0368834 A1 | 12/2016 | Nyce et al. |
| 2016/0376148 A1 | 12/2016 | Mamedov et al. |
| 2017/0014807 A1 | 1/2017 | Liang et al. |
| 2017/0106327 A1 | 4/2017 | Sadasivan Vijayakumari et al. |
| 2017/0107162 A1 | 4/2017 | Duggal et al. |
| 2017/0113980 A1 | 4/2017 | Radaelli et al. |
| 2017/0190638 A1 | 7/2017 | Liang et al. |
| 2017/0247803 A1 | 8/2017 | Sofranko |
| 2017/0260114 A1 | 9/2017 | Nyce et al. |
| 2017/0267605 A1 | 9/2017 | Tanur et al. |
| 2017/0275217 A1 | 9/2017 | Weinberger et al. |
| 2017/0283345 A1 | 10/2017 | Schammel et al. |
| 2017/0297975 A1 | 10/2017 | Radaelli et al. |
| 2017/0320793 A1 | 11/2017 | Fritz |
| 2017/0341997 A1 | 11/2017 | Nyce et al. |
| 2018/0118637 A1 | 5/2018 | Zurcher et al. |
| 2018/0162785 A1 | 6/2018 | Liang et al. |
| 2018/0169561 A1 | 6/2018 | Jonnavittula et al. |
| 2018/0179125 A1 | 6/2018 | Radaelli et al. |
| 2018/0186707 A1 | 7/2018 | Abudawoud et al. |
| 2018/0215682 A1 | 8/2018 | Rafique et al. |
| 2018/0222818 A1 | 8/2018 | Radaelli et al. |
| 2018/0272303 A1 | 9/2018 | Simanzhenkov et al. |
| 2018/0282658 A1 | 10/2018 | Takahama et al. |
| 2018/0305273 A1 | 10/2018 | Patel et al. |
| 2018/0305274 A1 | 10/2018 | Rafique et al. |
| 2018/0327334 A1 | 11/2018 | Radaelli et al. |
| 2018/0353940 A1 | 12/2018 | Liang et al. |
| 2019/0010096 A1 | 1/2019 | Schammel et al. |
| 2019/0119182 A1 | 4/2019 | McCormick et al. |
| 2019/0143288 A1 | 5/2019 | Bao et al. |
| 2019/0169089 A1 | 6/2019 | Cizeron et al. |
| 2019/0169090 A1 | 6/2019 | Sarsani et al. |
| 2019/0177246 A1 | 6/2019 | Nyce et al. |
| 2019/0389788 A1 | 12/2019 | Mamedov et al. |
| 2020/0031734 A1 | 1/2020 | Cizeron et al. |
| 2020/0031736 A1 | 1/2020 | Weinberger et al. |
| 2020/0048165 A1 | 2/2020 | Duggal et al. |
| 2020/0055796 A1 | 2/2020 | Nyce et al. |
| 2020/0071242 A1 | 3/2020 | Patel et al. |
| 2020/0131100 A1 | 4/2020 | Schammel et al. |
| 2020/0172452 A1 | 6/2020 | Duggal et al. |
| 2020/0189994 A1 | 6/2020 | Radaelli et al. |
| 2020/0207684 A1 | 7/2020 | Rafique et al. |
| 2020/0207685 A1 | 7/2020 | Nyce et al. |
| 2020/0216370 A1 | 7/2020 | Rafique et al. |
| 2020/0231519 A1 | 7/2020 | Abudawoud et al. |

FOREIGN PATENT DOCUMENTS

| | | |
|---|---|---|
| CA | 2800142 C | 6/2018 |
| CN | 1403375 A | 3/2003 |
| CN | 101224432 A | 7/2008 |

(56) References Cited

FOREIGN PATENT DOCUMENTS

| | | |
|---|---|---|
| CN | 101387019 A | 3/2009 |
| CN | 101747927 A | 6/2010 |
| CN | 102093157 A | 6/2011 |
| CN | 102125825 A | 7/2011 |
| DE | 1905517 A1 | 8/1970 |
| DE | 2540257 A1 | 4/1977 |
| DE | 3406751 A1 | 8/1985 |
| DE | 4039960 A1 | 9/1991 |
| DE | 4338414 C1 | 3/1995 |
| DE | 4338416 C1 | 4/1995 |
| DE | 102011080294 A1 | 2/2013 |
| EP | 106392 A1 | 4/1984 |
| EP | 177327 A2 | 4/1986 |
| EP | 253522 A2 | 1/1988 |
| EP | 303438 A2 | 2/1989 |
| EP | 336823 A1 | 10/1989 |
| EP | 608447 A1 | 8/1994 |
| EP | 634211 A1 | 1/1995 |
| EP | 722822 A1 | 7/1996 |
| EP | 761307 A1 | 3/1997 |
| EP | 764467 A1 | 3/1997 |
| EP | 716064 B1 | 7/1998 |
| EP | 1110930 A1 | 6/2001 |
| EP | 1632467 A1 | 3/2006 |
| EP | 1749807 A1 | 2/2007 |
| EP | 1749806 B1 | 10/2008 |
| EP | 3081292 A1 | 10/2016 |
| FR | 649429 A | 12/1928 |
| FR | 2600556 A1 | 12/1987 |
| GB | 733336 A | 7/1955 |
| GB | 2191212 A | 12/1987 |
| JP | 2005161225 A | 6/2005 |
| RU | 2412147 C2 | 2/2011 |
| RU | 2447048 C1 | 4/2012 |
| WO | 8607351 A1 | 12/1986 |
| WO | 0204119 A1 | 1/2002 |
| WO | 2004033488 A2 | 4/2004 |
| WO | 2004056479 A1 | 7/2004 |
| WO | 2004103936 A1 | 12/2004 |
| WO | 2005067683 A2 | 7/2005 |
| WO | 2007125360 A1 | 11/2007 |
| WO | 2007130515 A2 | 11/2007 |
| WO | 2008005055 A2 | 1/2008 |
| WO | 2008014841 A1 | 2/2008 |
| WO | 2008022147 A1 | 2/2008 |
| WO | 2008073143 A2 | 6/2008 |
| WO | 2008150451 A2 | 12/2008 |
| WO | 2008150451 A3 | 3/2009 |
| WO | 2009071463 A2 | 6/2009 |
| WO | 2009074203 A1 | 6/2009 |
| WO | 2009115805 A1 | 9/2009 |
| WO | 2010005453 A2 | 1/2010 |
| WO | 2011008464 A1 | 1/2011 |
| WO | 2011041184 A2 | 4/2011 |
| WO | 2011050359 A1 | 4/2011 |
| WO | 2010069488 A8 | 5/2011 |
| WO | 2011149996 A2 | 12/2011 |
| WO | 2012047274 A2 | 4/2012 |
| WO | 2012047274 A3 | 5/2012 |
| WO | 2012162526 A2 | 11/2012 |
| WO | 2013106771 A2 | 7/2013 |
| WO | 2013169462 A1 | 11/2013 |
| WO | 2013175204 A1 | 11/2013 |
| WO | 2013177433 A2 | 11/2013 |
| WO | 2013177461 A2 | 11/2013 |
| WO | 2014011646 A1 | 1/2014 |
| WO | 2014044387 A1 | 3/2014 |
| WO | 2014049445 A2 | 4/2014 |
| WO | 2014089479 A1 | 6/2014 |
| WO | 2013177433 A3 | 8/2014 |
| WO | 2014131435 A1 | 9/2014 |
| WO | 2014143880 A1 | 9/2014 |
| WO | 2015000061 A1 | 1/2015 |
| WO | 2015003193 A2 | 1/2015 |
| WO | 2015021177 A1 | 2/2015 |
| WO | 2015048295 A1 | 4/2015 |
| WO | 2015066693 A1 | 5/2015 |
| WO | 2015081122 A2 | 6/2015 |
| WO | 2015105911 A1 | 7/2015 |
| WO | 2015106023 A1 | 7/2015 |
| WO | 2015081122 A3 | 12/2015 |
| WO | 2016012371 A1 | 1/2016 |
| WO | 2016149507 A1 | 9/2016 |
| WO | 2016160563 A1 | 10/2016 |
| WO | 2016205411 A2 | 12/2016 |
| WO | 2016210006 A2 | 12/2016 |
| WO | 2016210006 A3 | 4/2017 |
| WO | 2017065947 A1 | 4/2017 |
| WO | 2016205411 A3 | 9/2017 |
| WO | 2017180910 A1 | 10/2017 |
| WO | 2018009356 A1 | 1/2018 |
| WO | 2018085820 A1 | 5/2018 |
| WO | 2018102601 A1 | 6/2018 |
| WO | 2018114900 A1 | 6/2018 |
| WO | 2018118105 A1 | 6/2018 |
| WO | 2019010498 A1 | 1/2019 |
| WO | 2019055220 A1 | 3/2019 |

OTHER PUBLICATIONS

Li, et al. Energy and Fuels. 2008, 22: 1897-1901.

Ling, et al. Preparation of Ag core Au shell Nanowires and Their Surface Enhanced Raman Spectroscopic Studies. Acta Chimica Sinica. 65 (9): 779-784, 2007.

Liu, et al. A novel Na2 W04-Mn.SiC monolithic foam catalyst with improved thermal properties for the oxidative coupling of methane. Catalysis Communications 9: 1302-1306, 2008.

Liu, et al. Increasing the Density of Adsorbed Hydrogen with Coordinatively Unsaturated Metal Centers in Metal-Organic Frameworks Langmuir, 2008, 24:4772-77.

Lunsford, J.H. Catalytic conversion of methane to more useful chemicals and fuels: a challenge for the 21st century. Catalysis Today (2000) 63:165-174.

Lunsford. The Catalytic Oxidative Coupling of Methane. Angew. Chem Int. Ed. Engl. 1995; 34:970-980.

Lunsford, et al. The oxidative coupling of methane on chlorinated Lithium-doped magnesium oxide. J. Chem. Soc., Chem. Commun., 1991, 1430-1432.

Makal, et al., Methane storage in advanced porous materials, Critical Review, Chem. Soc. Rev., 2012, 41:7761-7779.

Matherne, et al. Chapter 14, Direct Conversion of Methane to C2's and Liquid Fuels: Process Economics, Methane Conversion by Oxidative Processes (1992), 463-482.

Miltenburg, A.S. Adsorptive Separation of Light Olefin/Paraffin Mixtures: Dispersion of Zeolites. (2007) Ponsen & Looijen B.V., Wageningen, the Netherlands.

Mimoun, H. et al. Oxypyrolysis of Natural Gas. Appl Catalysis (1990) 58:269-280.

Mleczko, et al. Catalytic oxidative coupling of methane-reaction engineering aspects and process schemes. Fuel Processing Technology 42:217-248, 1995.

Mokhatab et al. "Handbook of Natural Gas Transmission and Processing: Principles and Practices" 2015. Chapter 7, pp. 237-242. (Year 2015).

Morgan, C.R. et al. Gasoline from Alcohols. Ind Eng Chem Prod Res Dev(1981) 20:185-190.

Natural Gas Spec Sheet, 2003, prepared by Florida Power and Light Company.

Neltner, et al. Production of Hydrogen Using Nanocrystalline Protein-templated catalysts on M12 Phage. ACSNano 4(6):3227-3236, 2010.

Neltner. Hybrid Bio-templated Catalysts. Doctoral Thesis, Massachusetts Institute of Technology, Jun. 2010, 156 pages.

Nexant/Chemsystems HDPE Report, Perp 09/10-3, Jan. 2011.

Nghiem, XS. Ethylene Production by Oxidative Coupling of Methane: New Process Flow Diagram based on Adsorptive Separation. Berlin, Mar. 14, 2014.

Nielsen, et al. Treat LPGs with amines. Hydrocarbon Process 79 (1997): 49-59.

(56) References Cited

OTHER PUBLICATIONS

Nijem, et al. Tuning the gate opening pressure of Metal-Organic Frameworks (MOFs) for the selective separation of hydrocarbons. J Am Chem Soc. Sep. 19, 2012;134(37):15201-4. Epub Sep. 10, 2012.

Niu, et al. Preparation and characterization of La2 O3CO3 nanowires with high surface areas. Jounral of the Chinese Rare Earth Society 23 (Spec. Issue): 33-36, Dec. 2005.

Ogura et al. Formation of Uniform Mesopores in ZSM-5 Zeolite through Treatment in Alkaline Solution, Chemistry Letters, 2000, pp. 882-883.

Ohashi, Y. et al. Development of Carbon Dioxide Removal System from the Flue Gas of Coal Fired Power Plant. Energy Procedia (2011) 4:29-34.

Oil Refinery—Wikipedia, The Free Encyclopedia Website. Jan. 2009.

Olah, G. Hydrocarbon Chemistry. 2nd Edition, John Wiley & Sons, 2003.

Olefins Conversion Technology, Website Accessed Aug. 28, 2014, http:www.CBI.com.

Pak, et al. Elementary Reactions in the Oxidative Coupling of Methane over Mn/NA2 W04/SiO2 and Mn/NA2 W04/Mg0 Catalysts. Journal of Catalysis 179:222-230, 1998.

Pan, Sharp separation of C2/C3 hydrocarbon mixtures by zeolitic imidazolate framework-8 (ZIF-8) membranes synthesized in aqueous solutions. Chem Commun (Camb). Oct. 7, 2011;47(37):10275-7. doi: 10.1039/c1cc14051e. Epub Aug. 22, 2011.

Process Systems; "Steam Tables" Apr. 8, 2017—https://web.archive.org/web/20170408152403/https://valvesonline.com.au/references/steamtables/.

Qiu, et al. Steady-state conversion of methane to aromatics in high yields using an integrated recycle reaction system. Catalysis Letters 48: 11-15, 1997.

Rousseau, Handbook of Separation Process Technology, 1987, p. 682.

Saito, et al. Dehydrogenation of Propane Over a Silica-Supported Gallium Oxide Catalyst. Catalysis Letters, Sep. 2003, vol. 89, Issue 3-4, pp. 213-217.

Schweer, et al. OCM in a fixed bed reactor: limits and perspectives. Catalysis Today, vol. 21, No. 2-3, Dec. 1, 1994, pp. 357-369.

Seeberger, A. et al. Gas Separation by Supported Ionic Liquid Membranes. DGMK-Conference, Hamburg, Germany (2007).

Simons, K. Membrane Technologies for CO2 Capture. Dissertation, U. of Twente (2010).

Smith, et al. Recent developments in solvent absorption technologies at the CO2CRC in Australia. Energy Procedia 1 (2009): 1549-1555.

Somorjai, et al. High technology catalysts towards 100% selectivity Fabrication, characterization and reaction studies. Catalysis today 100:201-215, 2005.

Sugiyama, et al. Redox Behaviors of Magnesium Vanadate Catalysts During the Oxidative Dehydrogenation of Propane. Catalysis Letters, Sep. 2003, vol. 89, Issue 3-4, pp. 229-233.

Suzuki, K. Toshiba's Activity in Clean Coal and Carbon Capture Technology for Thermal Power Plants. APEC Clean Fossil Energy Technical and Policy Seminar (Feb. 22, 2012).

Tabak, S.A. et al. Conversion of Methanol over ZSM-5 to Fuels and Chemicals. Cat Today (1990) 307-327.

Takanabe, et al. Mechanistic Aspects and Reaction Pathways for Oxidative Coupling of Methane on Mn/NA2 W04/SiO2 Catalysts. Journal of Physical Chemistry C 113(23):10131-10145, 2009.

Takanabe, et al. Rate and Selectivity Enhancements Mediated by OH Radicals in the Oxidative coupling of Methane Catalyzed by Mn/NA2 W04/SiO2 . Angewandte Chemie International Edition 47:7689-7693, 2008.

Tong, et al. Development strategy research of downstream products of ethene in Tianjin. Tianjin Economy, pp. 37-40,1996.

Trautmann, et al. Cryogenic technology for nitrogen rejection from variable content natural gas. Presented at the XIV Convencion Internacional de Gas, Caracas, Venezuela, May 10-12, 2000, 13 pages.

Wang, et al. Autothermal oxidative coupling of methane on the SrCO3/Sm2 03 catalysts. Catalysis communications 10: 807-810, 2009.

Wang, et al. Comparative study on oxidation of methane to ethane and ethylene over NA2 W04-Mn/SiO2 catalysts prepared by different methods. Journal of Molecular Catalysis A: Chemical 245:272-277, 2006.

Wang, et al. Low temperature selective oxidation of methane to ethane and ethylene over BaCO3/La2 03 catalysts prepared by urea combustion method. Catalysis communications 7: 5963, 2006.

Wang, et al., Critical Influence of BaCO3 on Low Temperature Catalytic Activity of BaCO3/Zr02 Catalysts for Oxidative Coupling of Methane, Catalysis Letters (2009), 129:156-162.

Water Electrolysis & Renewable Energy Systems. FuelCellToday (May 2013).

Wikipedia search, Adiabatic Process, Mar. 2011, 10 pages.

Witek-Krowiak, A. et al. Carbon Dioxide Removal in a Membrane Contactor-Selection of Absorptive Liquid/Membrane System. Intl J Chem Eng and Appl. (2012) 3(6):391-395.

Wong, et al. Oxidative coupling of methane over alkali metal oxide promoted La2 03/BaCO3 catalysts. J. Chem. Tech. Biotechnol. 65:351-354, 1996.

Wu, et al., High-Capacity Methane Storage in Metal-Organic Frameworks M2(dhtp): The Important Role of Open Metal Sites, J. Am. Chem. Soc. 131 (13):4995-5000.

Xu, et al. Maximise ethylene gain and acetylene selective hydrogenation efficiency. Petroleum technology quarterly 18.3 (2013): 39-42.

Xu, G. et al. An Improved CO2 Separation and Purification System Based on Cryogenic Separation and Distillation Theory. Energies (2014) 7:3484-3502.

Yan, D. Modeling and Application of a Thermoelectric Generator. Thesis, Univ. Toronto (2011).

Yang, et al. Anistropic synthesis of boat shaped core shell Au-Ag nanocrystals and nanowires. Nanotechnology 17: 2304-2310, 2006.

Yu, et al. Oxidative coupling of methane over acceptor-doped SrTi 03: Correlation between p-type conductivity and C2 selectivity and C2 yield. Journal of Catalysis. 13 (5): 338-344, 1992.

Zhang, Q. Journal of Natural Gas Chem., 12:81, 2003.

Zhao, et al. Technologies and catalysts for catalytic preparation of ethene. Industrial catalysis 12 (Supplement): 285-289, 2004.

Zhou, et al. Functionalization of lanthanum hydroxide nanowires by atom transfer radical polymerization. Nanotechnology 18, 2007, 7 pages.

Zhou. BP-UOP Cyclar Process. Handbook of Petroleum Refining Processes, The McGraw-Hill Companies (2004), pp. 2.29-2.38.

Zhou, et al., Enhanced H2 Adsorption in Isostructural Metal-Organic Frameworks with Open Metal Sites: Strong Dependence of the Binding Strength on Metal Ions, J. Am. Chem. Soc., 2008, 130(46):15268-69.

Zimmerman, et al. Ethylene. Ulmann's Encyclopedia of Inudstrial Chemisty, Wiley-VCH Verlag GmbH & Co. KGaA, Weinheim, Germany, 2009, 66 pages.

International search report and written opinion dated Sep. 5, 2017 for PCT Application PCTUS2017025544.

U.S. Appl. No. 15/476,889 Office Action dated Apr. 30, 2018.

Extended European Search Report dated Jul. 14, 2020 for EP Application No. 17885254.7.

Chemical Engineering—"Separation Processes: Supercritical CO2: A Green Solvent" Feb. 1, 2010.

Agarwal, et al., Aqueous Au-Pd colloids catalyze selective CH4 oxidation to CH3OH with O2 under mild conditions, Science 358, Oct. 13, 2017, 223-27.

Ahari, et al. Effects of operating parameters on oxidative coupling of methane over Na-WMn/SiO2 catalyst at elevated pressures. Journal of Natural Gas Chemistry. vol. 20, Issue 2, Mar. 2011, pp. 204-213.

American Petroleum Institute Publication 534 Heat Recovery Steam Generators Jan. 1995 (51 pages).

(56) References Cited

OTHER PUBLICATIONS

Autothermal Partial Oxidative Coupling of Methane. Ip.com, Prior Art Database Technical Disclosure, Jul. 29, 2008, 5 pages.
Barrett, et al. The determination of pore volume and area distributions in porous substances—Compuatations from nitrogen isotherms. J. Am. Chem. Soc., 1951, vol. 73, pp. 373-380.
Berstad, D. et al. Low-temperature $CO_2$ removal from natural gas. Energy Procedia (2012) 26:41-48.
Bloch, et al. Hydrocarbon Separations in a Metal-Organic Framework with Open Iron(II) Coordination Sites, Science, 2012, 335:1606-1610.
Bollmann, et al. Ethylene tetramerization: a new route to produce 1-octene in exceptionally high selectivities. J Am Chem Soc. Nov. 17, 2004;126(45):14712-3.
Botella, et al. Effect of Potassium Doping on the Catalytic Behavior of Mo-V-Sb Mixed Oxide Catalysts in the Oxidation of Propane to Acrylic Acid. Catalysis Letters, Sep. 2003, vol. 89, Issue 3-4, pp. 249-253.
Carter, et al. High activity ethylene trimerisation catalysts based on diphosphine ligands. Chem Commun (Camb). Apr. 21, 2002;(8):858-9.
Caskey, et al., Dramatic Tuning of Carbon Dioxide Uptake via Metal Substitution in a Coordination Polymer with Cylindrical Pores, J. Am. Chem. Soc., (2009), 130(33): 10870-71.
Cavani, et al. Oxidative dehydrogenation of ethane and propane: How far from commercial implementation? Catalysis Today. 2007; 127(1-4):113-131.
Chemsystems PERP Report Ethylene Oxide/Ethylene Glycol 2005.
Chen, et al. M2 Forming—A Process for Aromatization of Light Hydrocarbons. Ind. Eng. Chem. Process. Des. Dev. 1986, 25, 151-155.
Choudhary, et al. Aromatization of dilute ethylene over Ga-modified ZSM-5 type zeolite catalysts. Microporous and Mesoporous Materials 47: 253-267, 2001.
Choudhary, et al. Oxidative conversion of methane/natural gas into higher hydrocarbons. Catalysis Surveys from Asia 8(1): Feb. 15-25, 2004.
Choudhary, et al. Surface Basicity and Acidity of Alkaline Earth-Promoted $La_2O_3$ Catalysts and Their Performance in Oxidative Coupling of Methane. Journal of Chemical Technology and Bio technology 72:125-130, 1998.
Christopher, et al. Engineering Selectivity in Heterogeneous Catalysis: Ag Nanowires as Selective Ethylene Epoxidation Catalysts. Journal of the American Chemical Society 130: 11264-11265, 2008.
Corma, From Microporous to Mesoporous Molecular Sieve Materials and Their Use in Catalysis, Chern. Rev., 97, 1997, pp. 2373-2419.
Debart, et al. α-$MNO_2$ Nanowires: A catalyst for the $O_2$ Electrode in Rechargeabl Lithium Batteries. Angewandte Chemie International Edition 47: 4521-4524, 2008.
Dietzel, et al., Adsorption properties and structure of $CO_2$ adsorbed on open coordination sites of metal-organic framework Ni2(dhtp) from gas adsorption, IR spectroscopy and X-ray diffraction, Chem. Commun. (2008), 5125-5127.
Ding, X et al. Effect of acid density of HZSM-5 on the oligomerization of ethylene in FCC dry gas. J Nat Gas Chem (2009) 18:156-160.
Duan, et al. Three-dimensional copper (II) metal-organic framework with open metal sites and anthracene nucleus for highly selective $C_2H_2/CH_4$ and $C_2NH_2/CO_2$ gas separation at room temperature. Microporous and Mesoporous Materials. vol. 181, Nov. 15, 2013, pp. 99-104.
Enger, et al. A review of catalytic partial oxidation of methane to synthesis gas with emphasis on reaction mechanisms over transition metal catalysts. Applied Catalysis A: General 346 (1-2): Aug. 1-27, 2008.
Fallah, et al., A New Nano-($2Li_2O/MgO$) Catalyst/Porous Alpha-Alumina Composite for the Oxidative Coupling of Methane Reaction, AIChE Journal, Mar. 2010, 56(3):717-28.

Gao, et al. A study on methanol steam reforming to $CO_2$ and $H_2$ over the $La_2CO_4$ nanofiber catalyst. Journal of Solid State Chemistry 181: 7-13, 2008.
Gao, et al. The direct decomposition of NO over the $La_2CuO_4$ nanofiber catalyst. Journal of Solid State Chemistry 181: 2804-2807, 2008.
Geier, et al., Selective adsorption of ethylene over ethane and propylene over propane in the metal-organic frameworks M2(dobdc) (M = Mg, Mn, Fe, Co, Ni, Zn), Chem. Sci., 2013, 4:2054-2061.
Ghosh, et al., Absorption of carbon dioxide into aqueous potassium carbonate promoted by boric acid, Energy Procedia, Feb. 2009, pp. 1075-1081.
Godini, et al. Techno-economic analysis of integrating the methane oxidative coupling and methane reforming processes. Fuel processing technology 2013 v.106 pp. 684-694.
Goto et al, Mesoporous Material from Zeolite, Journal of Poruous Materials, 2002, pp. 43-48.
Graves, C.R. Recycling $CO_2$ into Sustainable Hydrocarbon Fuels: Electrolysis of $CO_2$ and $H_2O$. Dissertation, Columbia University (2010).
Guo, et al. Current Status and Some Perspectives of Rare Earth Catalytic Materials. Journal of the Chinese Rare Earth Society 25(1): Feb. 1-15, 2007.
Guo, X. et al. Direct, Nonoxidative Conversion of Methane to Ethylene, Aromatics, and Hydrogen. Science (2014) 344:616-619.
Gupta, M. Review on Heat Recovery Unit with Thermoelectric Generators. Intl J Eng and Innov Tech (IJEIT) (2014) 4 (4):128-131.
Haag, W.O. et al. Aromatics, Light Olefins and Gasoline from Methanol: Mechanistic Pathways with ZSM-5 Zeolite Catalyst. J Mol Catalysis (1982) 17:161-169.
He, et al. A microporus metal-organic framework for highly selective separation of acetylene, ethylene, and ethane from methane at room temperature. Chemistry. Jan. 9, 2012; 18(2):613-9. doi 10.1002/chem.201102734. Epub Dec. 8, 2011.
Hosseinpour, Performance of CaX Zeolite for Separation of $C_2H_6$, $C_2H_4$, and $CH_4$ by Adsorption Process; Capacity, Selectivity, and Dynamic Adsorption Measurements, Separation Science and Technology, 2011, 46:349-355.
Huang, et al. Exploiting shape effects of $La_2O_3$ nanocrystals for oxidative coupling of methane reaction. Nanoscale 5 (22): 10844-10848, 2013.
Huang, et al. Exploiting shape effects of $La_2O_3$ nanocrystals for oxidative coupling of methane reaction. Nanoscale—Electronic Supplementary Material, 2013, 7 pages.
Iwamoto, M. One step formation of propene from ethene or ethanol through metathesis on nickel ion-loaded silica. Molecules. Sep. 13, 2011;16(9):7844-63.
Kaibe, H. et al. Recovery of Plant Waste Heat by a Thermoelectric Generating System. Komatsu Tech Report (2011) 57(164):26-30.
Kaminsky, M.P. et al. Deactivation of Li-Based Catalysts for Methane Oxidative Coupling. Poster ACS Symposium on Natural Gas Upgrading II (Apr. 5-10, 1992).
Kaminsky, M.P. et al. Oxygen X-Ray Absorption Near-Edge Structure Characterization of the Ba-Doped Yttria Oxidative Coupling Catalyst. J Catalysis (1992) 136:16-23.
Keller, Gas-Adsorption Processes: State of the Art, American Chemical Society, 1983,pp. 145-169.
Keller, et al. Synthesis of Ethylene via Oxidative Coupling of Methane. Journal of Catalysis 73: 9-19, 1982.
Knuuttila, et al. Advanced Polyethylene Technologies—Controlled Material Properties. Long Term Properties of Polyolefins Advances in Polymer Science vol. 169, 2004, pp. 13-28.
Kuang, et al. Grafting of PEG onto lanthanum hydroxide nanowires. Materials Letters 62:4078-4080, 2008.
Labinger. Oxidative coupling of methane: an inherent limit to selectivity? Catal. Lett. 1988; 1:371-376.
Li, B. et al. Advances in $CO_2$ capture technology: A patent review. Applied Energy (2013) 102:1439-1447.

* cited by examiner

METHODS AND SYSTEMS FOR PERFORMING CHEMICAL SEPARATIONS

CROSS-REFERENCE

This application is a continuation of U.S. patent application Ser. No. 16/170,429, filed Oct. 25, 2018, which is a continuation of U.S. patent application Ser. No. 15/476,889, filed Mar. 31, 2017, which claims priority to U.S. Provisional Patent Application No. 62/436,312, filed Dec. 19, 2016, each of which is entirely incorporated herein by reference for all purposes.

STATEMENT OF GOVERNMENT SUPPORT

This invention was made with government support under grant numbers DE-EE0005769 awarded by the United States Department of Energy (DOE). The government has certain rights in the invention.

BACKGROUND

The modern refining and petrochemical industry may make extensive use of fractionation technology to produce and separate various potentially desirable compounds from crude oil. The conventional fractionation technology may be energy intensive and costly to install and operate. Cryogenic distillation has been used to separate and recover hydrocarbon products in various refining and petrochemical industries.

SUMMARY

Recognized herein is a need for non-cryogenic separation methods and systems, such as for oxidative coupling of methane (OCM) processes.

Aspects of the present disclosure provide processes for recovering olefins from a stream containing mix of hydrocarbons by utilizing techniques based on the use of adsorbents. In some embodiments, systems and methods enable the separation, pre-separation, purification and/or recovery of hydrocarbons, including, but not limited to, olefins such as ethylene and propylene, paraffins such as methane and ethane, and $CO_2$, from a multicomponent hydrocarbon stream such as an effluent stream from an oxidative coupling of methane (OCM) reactor or an ethylene-to-liquids (ETL) reactor. The hydrocarbon stream can also be a feed to the OCM or ETL reactor in certain cases. In certain cases, the feed to the ETL reactor is an effluent from OCM reactor. In some cases, a separation process utilizing adsorbents can be used to purify and pre-treat existing hydrocarbon streams (such as refinery off-gases, cracker off-gas, streams from NGL plants, and others), followed by use of the resulting olefin rich stream (e.g., pressure swing adsorption tail gas) as the ETL feed.

The present disclosure provides various improvements in OCM and ETL processes, such as, without limitation, a separation and pre-separation process to recover desired or predetermined components from an OCM reactor effluent, $CO_2$ recovery and capture techniques, enhanced heat recovery methods to utilize the OCM reaction heat more efficiently, and techniques and technologies to further reduce the carbon footprint of the OCM process.

An aspect of the present disclosure provides a method for separating a product from a gas mixture, the method comprising: (a) at a first total pressure, directing a gas mixture comprising at least one impurity and a product gas into a pressure swing adsorption (PSA) vessel containing an adsorbent to adsorb the product gas on the adsorbent, wherein the product gas has a first partial pressure; (b) at a second total pressure, directing a sweep gas into the PSA vessel to adsorb the sweep gas on the adsorbent and displace the product from the adsorbent to yield a displaced product, wherein the sweep gas has a second partial pressure that is greater than the first partial pressure of the product in the gas mixture; and (c) desorbing the sweep gas from the adsorbent such that additional product is capable of adsorbing on the adsorbent.

In some embodiments, (c) is performed at substantially the first total pressure. In some embodiments, an amount of the product that adsorbs on the adsorbent at the first partial pressure in (a) is substantially equivalent to the amount of sweep gas that adsorbs on the adsorbent at the second partial pressure in (b). In some embodiments, an amount of heat released by the adsorption of the product in (a) is substantially equivalent to an amount of heat released by the adsorption of the sweep gas in (b). In some embodiments, the displaced product is enriched relative to the concentration of the product in the gas mixture by a factor of at least about 2, 3, 4, 5, 10, 15, 20 or more. In some embodiments, the displaced product includes at least some of the sweep gas. In some embodiments, the method further comprises, following displacing the product from the adsorbent, separating the product from the sweep gas (e.g., by distillation). In some embodiments, the product is ethylene. In some embodiments, the sweep gas is ethane. In some embodiments, the gas mixture comprises at least 3, 4, 5, 6, 7, 8, 9, 10 or more impurities. In some embodiments, the at least one impurity comprise carbon monoxide (CO), carbon dioxide ($CO_2$), methane, ethane, hydrogen ($H_2$), or any combination thereof. In some embodiments, the product has a concentration of less than about 30%, 25%, 20%, 15%, 10%, 5%, 1% or less in the gas mixture. In some embodiments, the adsorbent is a metal organic framework (MOF). In some embodiments, the MOF is $M_2$(dobdc). In some embodiments, at the first pressure, a selectivity of the adsorbent for adsorbing the product as compared to the at least one impurity is at least about 5, 10, 15, 20, 25, 30, 35, 40, 45, 50, 60, 70, 80, 90, 100 or more. In some embodiments, the at least one impurity is methane. In some embodiments, the gas mixture is derived from an effluent from an oxidative coupling of methane (OCM) reactor. In some embodiments, the method further comprises recycling the at least one impurity to the OCM reactor following the adsorption of the product from the gas mixture. In some embodiments, the method further comprises, prior to recycling the at least one impurity to the OCM reactor, converting carbon dioxide ($CO_2$), carbon monoxide (CO), and/or hydrogen ($H_2$) components of the at least one impurity to methane ($CH_4$). In some embodiments, following the adsorption of the product from the gas mixture, the gas mixture comprises a predetermined amount of a given impurity. In some embodiments, the given impurity is $CO_2$. In some embodiments, the adsorbent comprises (i) a first material that adsorbs the product and the given impurity, and (ii) a second material that adsorbs the product but does not substantially adsorb the given impurity. In some embodiments, an amount of the first material relative to an amount of the second material is selected to achieve the desired amount of the desired impurity. In some embodiments, the first material is a CaX zeolite and the second material is a metal organic framework.

Another aspect of the present disclosure provides a system for recovering compounds with two or more carbon atoms ($C_{2+}$ compounds) from an oxidative coupling of methane (OCM) process, the system comprising: (a) an OCM reactor configured to receive oxygen ($O_2$) and methane ($CH_4$) and react the $O_2$ and $CH_4$ to produce an OCM product stream, which OCM product stream comprises $C_{2+}$ compounds including ethylene ($C_2H_4$) and ethane ($C_2H_6$) and (ii) $C_1$ compounds including carbon dioxide ($CO_2$) and un-reacted $CH_4$; (b) a first separations unit fluidically coupled to the OCM reactor and configured to receive the OCM product stream, wherein the first separations unit is configured to separate the OCM product stream into (i) a first light stream comprising the un-reacted $CH_4$ and a first portion of the $CO_2$ (ii) a first heavy stream comprising the $C_2H_4$ and the $C_2H_6$ and a second portion of the $CO_2$; (c) a methanation reactor fluidically coupled to the first separation unit and to the OCM reactor, wherein the methanation reactor is configured to receive the first light stream and convert the first portion of the $CO_2$ into additional $CH_4$, which additional $CH_4$ is recycled to the OCM reactor; and (d) a second separations unit fluidically coupled to the first separations unit and configured to receive the first heavy stream, wherein the second separations unit is configured to separate the first heavy stream into (i) a second light stream comprising the $C_2H_6$ and (ii) a second heavy stream comprising the $C_2H_4$.

In some embodiments, the OCM reactor has a catalytic section and a cracking section, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$. In some embodiments, the second light stream is recycled to the cracking section of the OCM reactor. In some embodiments, the second portion of the $CO_2$ is vented. In some embodiments, the system further comprises a $CO_2$ removal unit fluidically coupled to the first separations unit and the second separations unit and configured to receive the first heavy stream, which $CO_2$ removal unit is configured to separate the second portion of the $CO_2$ from the first heavy stream before passing the first heavy stream on to the second separations unit. In some embodiments, the first separations unit contains CaX zeolite. In some embodiments, the second separations unit contains a metal organic framework (MOF). In some embodiments, the MOF is $M_2$(dobdc). In some embodiments, the MOF is $M_2$(m-dobdc). In some embodiments, the first separations unit is a pressure swing adsorption (PSA) unit. In some embodiments, the second separations unit is a pressure swing adsorption (PSA) unit. In some embodiments, the first separations unit is configured to be purged with vacuum, with ethane, with propane, or with any combination thereof. In some embodiments, the second separations unit is configured to be purged with vacuum, with ethane, with propane, or with any combination thereof. In some embodiments, the first separations unit and the second separations unit are configured to be purged with propane. In some embodiments, the first separations unit and the second separations unit are layers of a separation bed. In some embodiments, the first separations unit and the second separations unit are combined in a single separations unit having $M_2$(m-dobdc).

Another aspect of the present disclosure provides a method for separating oxygen ($O_2$) from nitrogen ($N_2$), the method comprising: (a) at a first pressure, directing a mixture of $O_2$ and $N_2$ into a pressure swing adsorption (PSA) vessel containing an adsorbent to adsorb the $O_2$ on the adsorbent, wherein the adsorbent is a metal organic framework (MOF) that is selective for $O_2$; and (b) at a second pressure that is less than the first pressure, desorbing the $O_2$ from the adsorbent with a purge gas.

In some embodiments, the method further comprises depressurizing the PSA vessel prior to (b). In some embodiments, the second pressure is less than atmospheric pressure. In some embodiments, the second pressure is less than about 1 bar, 0.9 bar, 0.8 bar, 0.7 bar, 0.6 bar, 0.5 bar, 0.4 bar, 0.3 bar, 0.2 bar, 0.1 bar or less. In some embodiments, the purge gas displaces the $O_2$ from the adsorbent, whereby the purge gas becomes adsorbed on the adsorbent. In some embodiments, the purge gas is $CO_2$ or $CH_4$. In some embodiments, the purge gas is air. In some embodiments, the purge gas is the $N_2$ that is not adsorbed in (a). In some embodiments, the MOF is $M_2$(dobdc). In some embodiments, the MOF is $Fe_2$(dobdc). In some embodiments, the mixture of $O_2$ and $N_2$ is air. In some embodiments, the first pressure is a pressure such that the adsorbent is at least about 70%, 80%, 90%, 95%, 99% saturated with $O_2$. In some embodiments, (a) is performed for less than about 1 minute. In some embodiments, (a) and (b) are performed at different temperatures.

Another aspect of the present disclosure provides a system for separating oxygen ($O_2$) from nitrogen ($N_2$), the system comprising: a pressure swing adsorption (PSA) vessel containing an adsorbent, wherein the PSA vessel is configured to receive a mixture of $O_2$ and $N_2$ at a first pressure and adsorb the $O_2$ on the adsorbent, wherein the adsorbent is a metal organic framework (MOF) that is selective for $O_2$; a source of a purge gas in fluid communication with the PSA vessel; and a controller operatively coupled to the source of the purge gas, wherein the controller is programmed to subject the purge gas to flow from the source of the purge gas to the PSA vessel to desorb the $O_2$ from the adsorbent at a second pressure that is less than the first pressure.

In some embodiments, the controller is programmed to depressurize the PSA vessel prior to subjecting the purge gas to flow from the source of the purge gas to the PSA vessel. In some embodiments, the second pressure is less than atmospheric pressure. In some embodiments, the second pressure is less than about 1 bar, 0.9 bar, 0.8 bar, 0.7 bar, 0.6 bar, 0.5 bar, 0.4 bar, 0.3 bar, 0.2 bar, 0.1 bar or less. In some embodiments, the purge gas is $CO_2$ or $CH_4$. In some embodiments, the purge gas is air. In some embodiments, the MOF is $M_2$(dobdc). In some embodiments, the MOF is $Fe_2$(dobdc). In some embodiments, the system further comprises an oxidative coupling of methane (OCM) reactor downstream of the PSA vessel, wherein the OCM reactor is configured to (i) receive methane ($CH_4$) and at least a portion of the $O_2$ and (ii) react the at least the portion of the $O_2$ and the $CH_4$ in an OCM process to yield a product stream comprising compounds with two or more carbon atoms ($C_{2+}$ compounds).

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and the $CH_4$ in an OCM process to yield a product stream comprising (i) $C_{2+}$ compounds including olefins and paraffins and (ii) carbon monoxide (CO) and/or carbon dioxide ($CO_2$); (b) directing the product stream from the OCM reactor into a separations unit that selectively adsorbs the olefins from the paraffins, wherein the separations unit comprises (i) a pressure swing adsorption (PSA) unit, (ii) a temperature swing adsorption (TSA) unit, or (iii) a membrane unit, and wherein the PSA unit, the TSA unit or the membrane unit comprises a sorbent that selectively adsorbs the olefins; and (c) desorbing the olefins from the sorbent.

In some embodiments, the separations unit selectively separates ethylene from the paraffins. In some embodiments, the sorbent has dispersed metal ions that are capable of complexing with the olefins. In some embodiments, the sorbent is selected from a zeolite, a molecular sieve sorbent, a carbon molecular sieve, an activated carbon, a carbon nanotube, a metal-organic framework (MOF), and a polymeric resin. In some embodiments, the method further comprises separating the CO and/or $CO_2$ from the $C_{2+}$ compounds. In some embodiments, the sorbent is a MOF, the olefin is ethylene, and the ethylene is desorbed from the MOF using ethane, propane or any combination thereof.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) $C_1$ compounds including un-reacted $CH_4$; and (b) directing the product stream into a separations unit that separates the $C_{2+}$ compounds from the $C_1$ compounds, which separations unit does not contain a de-methanizer.

In some embodiments, the separations unit contains a distillation column and an oil absorber. In some embodiments, the distillation column does not condense methane. In some embodiments, the separations unit comprises a MOF. In some embodiments, the $C_{2+}$ compounds are desorbed from the MOF using ethane, propane or any combination thereof.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor that reacts the $O_2$ and $CH_4$ in an OCM process to yield a product stream comprising (i) $C_{2+}$ compounds including ethylene ($C_2H_4$) and (ii) $C_1$ compounds including un-reacted $CH_4$; and (b) directing the product stream into a separations unit containing a metal organic framework (MOF) that produces (i) a bottoms stream comprising the $C_{2+}$ compounds and (ii) an overhead stream comprising the $C_1$ compounds.

In some embodiments, the method further comprises (c) directing the overhead stream to a methanation unit for converting carbon dioxide ($CO_2$) and/or carbon monoxide (CO) into methane ($CH_4$); and (d) directing the $CH_4$ into the OCM reactor. In some embodiments, the method further comprises (e) directing the bottoms stream to a second separations unit containing a metal organic framework (MOF) that separates olefins from paraffins. In some embodiments, the separations unit comprises a pressure swing absorber (PSA) that contains the MOF. In some embodiments, the separations unit comprises a temperature swing absorber (TSA) that contains the MOF. In some embodiments, the overhead stream includes hydrogen ($H_2$). In some embodiments, the $C_{2+}$ compounds are desorbed from the MOF using ethane, propane or any combination thereof.

Another aspect of the present disclosure provides a method for generating compounds with two or more carbon atoms ($C_{2+}$ compounds), comprising: (a) directing oxygen ($O_2$) and methane ($CH_4$) into an oxidative coupling of methane (OCM) reactor having a catalytic section and a cracking section to produce an OCM product stream, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$, and which product stream comprises (i) $C_{2+}$ compounds including ethylene ($C_2H_4$) and ethane ($C_2H_6$) and (ii) $C_1$ compounds including un-reacted $CH_4$; (b) directing the product stream into a separations unit containing a metal organic framework (MOF) that produces (i) a first stream comprising the $C_2H_4$, (ii) a second stream comprising the $C_2H_6$ and (iii) a third stream comprising the $C_1$ compounds; (c) directing the second stream into the cracking section; and (d) directing the third stream into the catalytic section.

In some embodiments, the third stream is directed to a methanation unit prior to directing to the catalytic section, which methanation unit converts carbon dioxide ($CO_2$) and/or carbon monoxide (CO) into methane ($CH_4$). In some embodiments, the separations unit comprises a pressure swing absorber (PSA) that contains the MOF. In some embodiments, the separations unit comprises a temperature swing absorber (TSA) that contains the MOF. In some embodiments, the third stream includes hydrogen ($H_2$). In some embodiments, the ethylene is desorbed from the MOF using ethane, propane or any combination thereof.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including olefins and paraffins and (ii) carbon monoxide (CO) and/or carbon dioxide ($CO_2$); and a separations unit fluidically coupled to the OCM reactor and configured to receive the product stream from the OCM reactor, wherein the separations unit selectively adsorbs the olefins from the paraffins, wherein the separations unit comprises (i) a pressure swing adsorption (PSA) unit, (ii) a temperature swing adsorption (TSA) unit, or (iii) a membrane unit, and wherein the PSA unit, the TSA unit or the membrane unit comprises a sorbent that selectively adsorbs the olefins, which olefins can be desorbed from the sorbent.

In some embodiments, the separations unit selectively separates ethylene from the paraffins. In some embodiments, the sorbent has dispersed metal ions that are capable of complexing with the olefins. In some embodiments, the sorbent is selected from a zeolite, a molecular sieve sorbent, a carbon molecular sieve, an activated carbon, a carbon nanotube, a metal-organic framework (MOF), and a polymeric resin. In some embodiments, the system further comprises a module capable of separating the CO and/or $CO_2$ from the $C_{2+}$ compounds. In some embodiments, the sorbent is a MOF, the olefin is ethylene, and the ethylene is desorbed from the MOF using ethane, propane or any combination thereof.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) $C_1$ compounds including un-reacted $CH_4$; and a separations unit fluidically coupled to the OCM reactor and configured to receive the product stream from the OCM reactor, wherein the separations unit separates the $C_{2+}$ compounds from the $C_1$ compounds, and wherein the separations unit does not contain a de-methanizer.

In some embodiments, the separations unit contains a distillation column and an oil absorber. In some embodiments, the distillation column does not condense methane. In some embodiments, the separations unit comprises a MOF. In some embodiments, the $C_{2+}$ compounds are desorbed from the MOF using ethane, propane or any combination thereof.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ in an OCM process to yield a product stream comprising (i) $C_{2+}$ compounds including ethylene ($C_2H_4$) and (ii) $C_1$ compounds including un-reacted $CH_4$; and a separations unit fluidically coupled to the OCM reactor and configured to receive the product stream from the OCM reactor, wherein the separations unit contains a metal organic framework (MOF) that produces (i) a bottoms stream comprising the $C_{2+}$ compounds and (ii) an overhead stream comprising the $C_1$ compounds.

In some embodiments, the system further comprises a methanation unit fluidically coupled to the separations unit and configured receive the overhead stream from the separations unit, wherein the methanation unit converts carbon dioxide ($CO_2$) and/or carbon monoxide (CO) into methane ($CH_4$), and wherein the $CH_4$ is directed into the OCM reactor. In some embodiments, the system further comprises a second separations unit fluidically coupled to the separations unit and configured receive the bottoms stream from the separations unit, wherein the second separations unit contains a metal organic framework (MOF) that separates olefins from paraffins. In some embodiments, the separations unit comprises a pressure swing absorber (PSA) that contains the MOF. In some embodiments, the separations unit comprises a temperature swing absorber (TSA) that contains the MOF. In some embodiments, the overhead stream includes hydrogen ($H_2$). In some embodiments, the $C_{2+}$ compounds are desorbed from the MOF using ethane, propane or any combination thereof.

Another aspect of the present disclosure provides a system for generating compounds with two or more carbon atoms ($C_{2+}$ compounds), comprising: an oxidative coupling of methane (OCM) reactor configured to receive oxygen ($O_2$) and methane ($CH_4$) and react the $O_2$ and $CH_4$ to produce an OCM product stream, the OCM reactor having a catalytic section and a cracking section, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$, and which product stream comprises (i) $C_{2+}$ compounds including ethylene ($C_2H_4$) and ethane ($C_2H_6$) and (ii) $C_1$ compounds including un-reacted $CH_4$; and a separations unit fluidically coupled to the OCM reactor and configured to receive the product stream from the OCM reactor, wherein the separations unit contains a metal organic framework (MOF) that produces (i) a first stream comprising the $C_2H_4$, (ii) a second stream comprising the $C_2H_6$ and (iii) a third stream comprising the $C_1$ compounds, and wherein the second stream and the third stream are directed into the cracking section and the catalytic section respectively.

In some embodiments, the third stream is directed to a methanation unit prior to directing to the catalytic section, which methanation unit converts carbon dioxide ($CO_2$) and/or carbon monoxide (CO) into methane ($CH_4$). In some embodiments, the separations unit comprises a pressure swing absorber (PSA) that contains the MOF. In some embodiments, the separations unit comprises a temperature swing absorber (TSA) that contains the MOF. In some embodiments, the third stream includes hydrogen ($H_2$). In some embodiments, the ethylene is desorbed from the MOF using ethane, propane or any combination thereof.

Another aspect of the present disclosure provides an adsorbent, comprising: (a) a first material that adsorbs (i) a product gas at a first heat of adsorption and (ii) a sweep gas at a second heat of adsorption; and (b) a second material that adsorbs the sweep gas at a third heat of adsorption, wherein the first material and the second material are included in a mixed material in a relative proportion such that the mixed material has an average heat of adsorption for the sweep gas, and wherein an absolute value of a difference between the first heat of adsorption and the average heat of adsorption is less than an absolute value of a difference between the first heat of adsorption and the second heat of adsorption.

In some embodiments, the first material is a metal-organic framework. In some embodiments, the second material is a metal-organic framework. In some embodiments, the first and second materials are different metal-organic frameworks. In some embodiments, the product gas is ethylene. In some embodiments, the sweep gas is propane. In some embodiments, at least one of the first material and the second material is a zeolite. In some embodiments, the first heat of adsorption, the second heat of adsorption and the third heat of adsorption have negative values. In some embodiments, the absolute value of the difference between the first heat of adsorption and the average heat of adsorption for the sweep gas is less than or equal to about 50% of the absolute value of the difference between the first heat of adsorption and the second heat of adsorption. In some embodiments, the mixed material comprises regions of the first material and of the second material having an average diameter of less than or equal to about 10 millimeters (mm). In some embodiments, the mixed material has a three dimensional shape that is adapted for use in a pressure swing adsorption unit.

Another aspect of the present disclosure provides an adsorbent, comprising: (a) a first material that adsorbs (i) a product gas at a first heat of adsorption and (ii) a sweep gas at a second heat of adsorption; and (b) a second material that adsorbs (i) the product gas at a third heat of adsorption and (ii) the sweep gas at a fourth heat of adsorption, wherein the first material and the second material are included in a mixed material in a relative proportion such that the mixed material has a first average heat of adsorption for the product gas and a second average heat of adsorption for the sweep gas, and wherein an absolute value of a difference between the first average heat of adsorption and the second average heat of adsorption is less than an absolute value of a difference between the first heat of adsorption and the second heat of adsorption.

In some embodiments, the second average heat of adsorption is substantially equal to the first average heat of adsorption. In some embodiments, the second average heat of adsorption is less than or equal to about 50% of the first average heat of adsorption. In some embodiments, an absolute value of a difference between the third heat of adsorption and the fourth heat of adsorption is less than an absolute value of a difference between the first heat of adsorption and the second heat of adsorption. In some embodiments, the first material is a metal-organic framework. In some embodiments, the second material is a metal-organic framework. In some embodiments, the first and second materials are different metal-organic frameworks. In some embodiments, the product gas is ethylene. In some embodiments, the sweep gas is propane. In some embodiments, at least one of the first material and the second material is a zeolite. In some embodiments, the first heat of adsorption, the second heat of adsorption, the third heat of adsorption and the fourth heat of adsorption have negative values. In some embodiments, the mixed material comprises regions of the first material and of the second material having an average diameter of less than or equal to about 10 millimeters (mm). In some embodiments, the mixed material has a three dimensional shape that is adapted for use in a pressure swing adsorption unit.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings or figures (also "FIG." and "FIGs." herein), of which:

DETAILED DESCRIPTION

Figure 1:
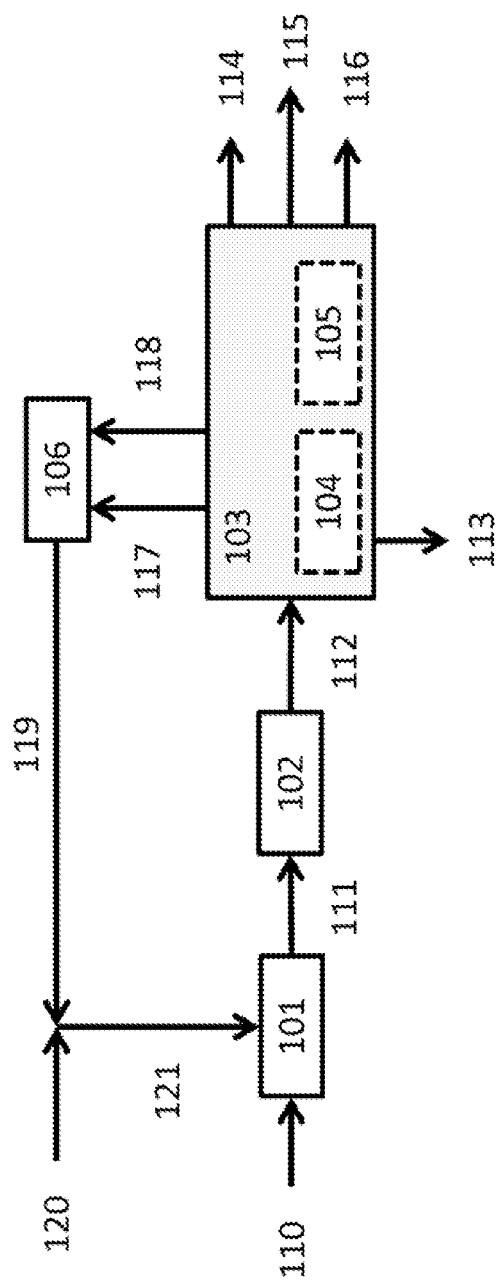
FIG. 1 shows an example oxidative coupling of methane (OCM) system of the present disclosure with advanced separation.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "higher hydrocarbon," as used herein, generally refers to a higher molecular weight and/or higher chain hydrocarbon. A higher hydrocarbon can have a higher molecular weight and/or carbon content that is higher or larger relative to a starting material in a given process (e.g., OCM or ETL). A higher hydrocarbon can be a higher molecular weight and/or chain hydrocarbon product that is generated in an OCM or ETL process. For example, ethylene is a higher hydrocarbon product relative to methane in an OCM process. As another example, a $C_{3+}$ hydrocarbon is a higher hydrocarbon relative to ethylene in an ETL process. As another example, a $C_{5+}$ hydrocarbon is a higher hydrocarbon relative to ethylene in an ETL process. In some cases, a higher hydrocarbon is a higher molecular weight hydrocarbon.

The term "OCM process," as used herein, generally refers to a process that employs or substantially employs an oxidative coupling of methane (OCM) reaction. An OCM reaction can include the oxidation of methane to a higher hydrocarbon and water, and involves an exothermic reaction. In an OCM reaction, methane can be partially oxidized and coupled to form one or more $C_{2+}$ compounds, such as ethylene. In an example, an OCM reaction is $2CH_4 + O_2 \rightarrow C_2H_4 + 2H_2O$. An OCM reaction can yield $C_{2+}$ compounds. An OCM reaction can be facilitated by a catalyst, such as a heterogeneous catalyst. Additional by-products of OCM reactions can include CO, $CO_2$, $H_2$, as well as hydrocarbons, such as, for example, ethane, propane, propene, butane, butene, and the like.

The term "non-OCM process," as used herein, generally refers to a process that does not employ or substantially employ an oxidative coupling of methane reaction. Examples of processes that may be non-OCM processes include non-OCM hydrocarbon processes, such as, for example, non-OCM processes employed in hydrocarbon processing in oil refineries, a natural gas liquids separations processes, steam cracking of ethane, steam cracking or naphtha, Fischer-Tropsch processes, and the like.

The terms "$C_{2+}$" and "$C_{2+}$ compound," as used herein, generally refer to a compound comprising two or more carbon atoms. For example, $C_{2+}$ compounds may include, without limitation, alkanes, alkenes, alkynes and aromatics containing two or more carbon atoms. $C_{2+}$ compounds can include aldehydes, ketones, esters and carboxylic acids. Examples of $C_{2+}$ compounds may include ethane, ethene, acetylene, propane, propene, butane, and butene.

The term "non-$C_{2+}$ impurities," as used herein, generally refers to material that does not include $C_{2+}$ compounds. Examples of non-$C_{2+}$ impurities, which may be found in certain OCM reaction product streams, may include nitrogen ($N_2$), oxygen ($O_2$), water ($H_2O$), argon (Ar), hydrogen ($H_2$) carbon monoxide (CO), carbon dioxide ($CO_2$) and methane ($CH_4$).

The term "small scale," as used herein, generally refers to a system that generates less than or equal to about 250 kilotons per annum (KTA) of a given product, such as an olefin (e.g., ethylene).

The term "world scale," as used herein, generally refers to a system that generates greater than about 250 KTA of a given product, such as an olefin (e.g., ethylene). In some examples, a world scale olefin system generates at least about 1,000, 1,100, 1,200, 1,300, 1,400, 1,500, 1,600, or more KTA of an olefin.

The term "item of value," as used herein, generally refers to money, credit, a good or commodity (e.g., hydrocarbon). An item of value can be traded for another item of value.

The term "carbon efficiency," as used herein, generally refers to the ratio of the number of moles of carbon present in all process input streams (in some cases including all hydrocarbon feedstocks, such as, natural gas and ethane and fuel streams) to the number of moles of carbon present in all commercially (or industrially) usable or marketable products of the process. Such products can include hydrocarbons that can be employed for various downstream uses, such as petrochemical or for use as commodity chemicals. Such products can exclude CO and $CO_2$. The products of the process can be marketable products, such as $C_{2+}$ hydrocarbon products containing at least about 99% $C_{2+}$ hydrocarbons and all sales gas or pipeline gas products containing at least about 90% methane. Process input streams can include input streams providing power for the operation of the process. In some cases, power for the operation of the process can be provided by heat liberated by an OCM reaction. In some cases, the systems or methods of the present disclosure have a carbon efficiency of at least about 50%, at least about 55%, at least about 60%, at least about 65%, at least about 70%, at least about 75%, at least about 80%, at least about 85%, or at least about 90%. In some cases, the systems or methods of the present disclosure have a carbon efficiency of between about 50% and about 85%, between about 55% and about 80%, between about 60% and about 80%, between about 65% and about 85%, between about 65% and about 80%, or between about 70% and about 80%.

The term "$C_{2+}$ selectivity," as used herein, generally refers to the percentage of the moles of methane that are converted into $C_{2+}$ compounds.

The term "specific oxygen consumption," as used herein, generally refers to the mass (or weight) of oxygen consumed by a process divided by the mass of $C_{2+}$ compounds produced by the process.

The term "specific $CO_2$ emission," as used herein, generally refers to the mass of $CO_2$ emitted from the process divided by the mass of $C_{2+}$ compounds produced by the process.

The term "unit," as used herein, generally refers to a unit operation. A unit operation may be one or more basic operations in a process. A unit may have one or more sub-units (or sub-systems). Unit operations may involve a physical change or chemical transformation, such as separation, crystallization, evaporation, filtration, polymerization, isomerization, other reactions, or combinations thereof. A unit may include one or more individual components. For example, a separations unit may include one or more separations columns or an amine unit may include one or more amine columns.

The term "sorbent," as used herein, generally refers to a material that may be used to adsorb or absorb another material, such as from a liquid or gas phase. A sorbent may be an adsorbent or an absorbent.

Separations Including Pressure Swing Adsorption (PSA)

Various non-cryogenic separation techniques have been employed for gas separations, purifications and recovery of hydrocarbons. Membrane based processes and adsorbents have been studied for large scale applications for olefins recovery. Since the development of synthetic adsorbents and pressure swing adsorption (PSA) cycles, adsorption has been playing an important role in gas separation and purification.

Processes of the present disclosure can employ a variety of different separations techniques, alone or in combination. For example, OCM processes can employ amine and caustic systems for $CO_2$ removal, molecular sieve guard beds for water removal, and cryogenic distillation or other separation techniques for recovery and purification of hydrocarbon components. Cryogenic separation can refer to separations using temperature levels below 120 K or about −153° C. Other techniques may include Selexol™ and Rectisol™ processes for $CO_2$ removal.

OCM product effluent can comprise a mixture of hydrocarbons including but not limited to methane, ethane, ethylene, propane, propylene, butanes, butenes, and/or higher hydrocarbons. OCM product effluent can also comprise varying amounts of other components such as hydrogen ($H_2$), nitrogen ($N_2$), carbon monoxide (CO), carbon dioxide ($CO_2$) and water ($H_2O$). The product of an OCM reaction can include ethylene. The ethylene product can be polymer grade, refinery grade or chemical grade. Depending on the purity level required, different separation and/or purification techniques can be employed with the OCM process. To recover high purity ethylene, separation methods such as those discussed herein can be used to remove a wide range of components.

Advantages of the advanced OCM processes described herein can include reducing the cost, reducing the number of unit operations ("units") used, and hence improving the overall process for producing high purity polymer grade ethylene. Overall conversion and carbon efficiency can also be improved. The separation methods disclosed herein can also improve the overall conversion and carbon efficiency.

Various separation and purification techniques discussed herein can be used to separate the OCM product effluent (e.g., process gas) into a plurality of streams, including but not limited to a first stream comprising methane, hydrogen, carbon monoxide and other lighter inerts and a second stream comprising ethane, ethylene, propylene, and higher hydrocarbons. Separation systems or subsystems employed can include those discussed herein, such as a cryogenic demethanizer, a membrane separation system, or a PSA based system.

The separation techniques discussed herein can be employed to remove $CO_2$, such as from an OCM product effluent stream. One or more separations techniques can be used to remove $CO_2$ including but not limited to absorption, adsorption, $CO_2$ distillation, membrane separation and combinations thereof. The separation technique can be cryogenic or non-cryogenic.

FIG. 1 shows a block flow diagram for an example OCM process. Oxygen 110 and methane 121 can be fed into an OCM reactor 101 for conversion into higher hydrocarbon compounds including ethylene. The OCM product stream 111 can be directed to a compressor 102, and the compressed product stream 112 can be fed into a separations system 103. The separations system can include pretreatment units 104, such as impurity and $CO_2$ removal units, as well as separations units 105, such as cryogenic, non-cryogenic, complexation, membrane, and other separations units. The separations system can be a combination of more than one separation techniques, such as those discussed above and elsewhere herein. The separation system can replace or supplement $CO_2$ removal, moisture removal, and/or cryogenic separation systems of existing OCM process systems. The compressor system may be optional for some types of separation processes. From the separations system, $CO_2$ can be vented 113, ethane 114 can be recovered, and optionally recycled to the OCM reactor, ethylene product 115 can be recovered, and $C_{3+}$ products 116 can be recovered. Additionally, $CO_2$ 117 and methane 118 can be directed from the separations system into a methanation unit 106. The methanation unit can produce methane from the $CO_2$, for recycling 119 back to the OCM reactor. Additional methane 120 can be added to the OCM reactor supply stream 121.

Cryogenic separation (e.g., distillation) can be used for recovering ethylene, propylene, and/or other components from olefin plants, refinery gas streams, and/or other sources. These separations in some instances may be difficult to accomplish due to e.g., proximity of relative volatilities, and significant temperature and pressure requirements for operation. The ethane/ethylene distillation can be performed at about −25° C. and 320 pounds per square inch gauge (psig) in a column containing over 100 trays. Distillation of propane and propylene can be performed at about −30° C. and 30 psig. These can be some of the most energy intensive distillations in the chemical and petrochemical industry. In general, the use of distillation towers to separate recover and purify components can be energy intensive.

Also provided in the present disclosure are adsorbents that may be employed for separation and purification of olefin rich streams. The adsorbents may include PSA-based adsorbent systems to separate, purify, and recover olefins like ethylene and propylene from streams containing one or more impurities such as methane, hydrogen, carbon monoxide, carbon dioxide, ethane, or others. The streams, or parts of the streams, can be generated in an OCM process, an ETL process, or combinations thereof. The streams can be final product streams where PSA is used to recover and purify the final product. The streams can be intermediate streams which are purified prior to use as a feed in a subsequent process, such as an ETL process, an ethylene cracker (steam cracker), a refining unit, a fuel gas system, a natural gas recovery plant or any other product fractionation or product treatment unit.

A pressure swing adsorption (PSA) process cycle is a process in which adsorption and desorption take place at different (higher or lower) conditions including such as temperatures, pressures, or combinations thereof. For example, reduction of pressure can be used to shift the adsorption equilibrium and affect regeneration of the adsorbent. Low pressure may not be as effective as temperature elevation in totally reversing adsorption, unless very high feed to purge pressure ratios are applied. Therefore, some PSA cycles can have high residual loadings and thus low operating loadings. These low capacities at high concentration may require that cycle times be short for reasonably sized beds (e.g., seconds to minutes). These short cycle times may be attainable because particles of adsorbent respond quickly to changes in pressure. Example uses for PSA processes include purification as well as applications where contaminants are present at high concentrations.

Figure 2:
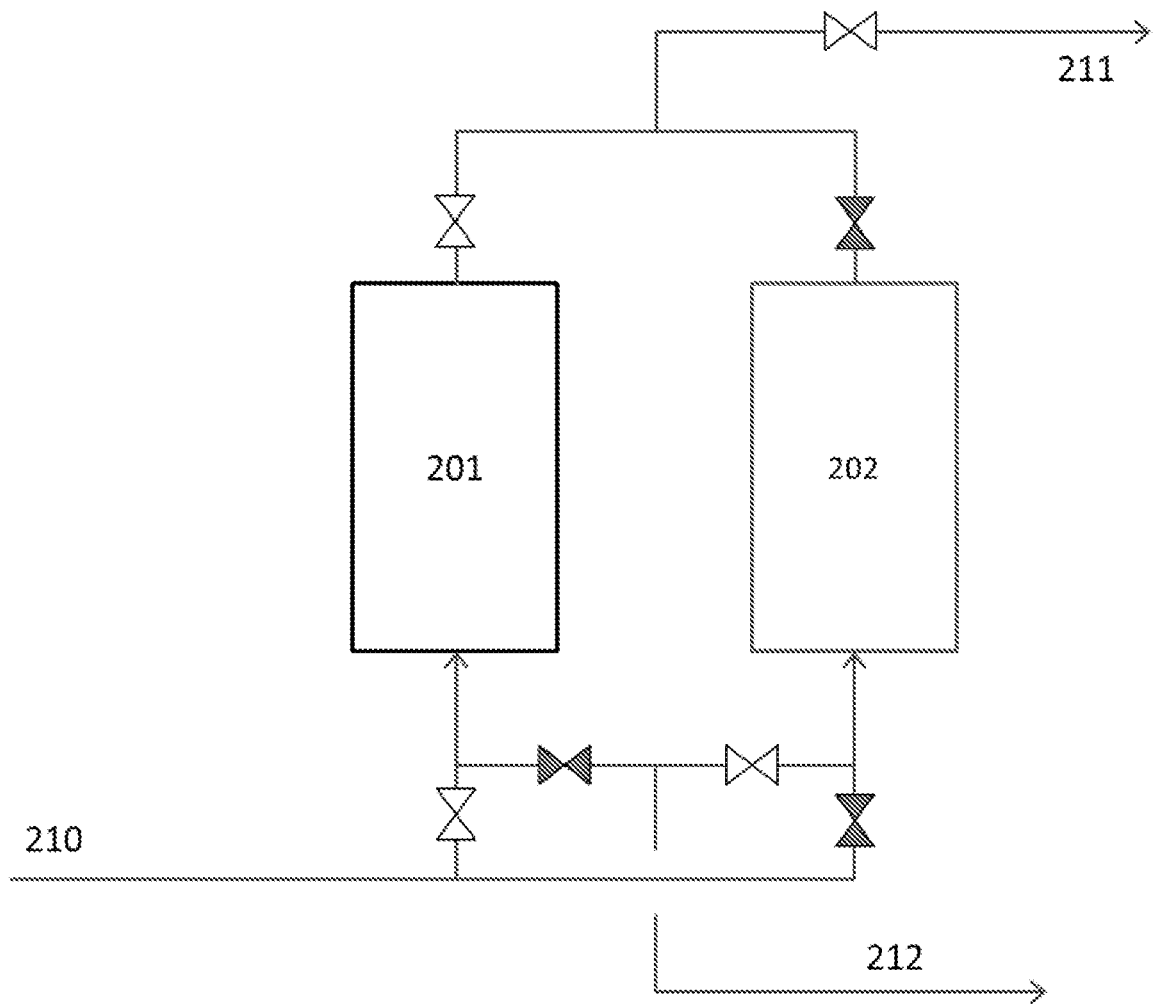
FIG. 2 shows an example of a pressure swing adsorption (PSA) system of the present disclosure.

As shown in FIG. 2, an example PSA system can comprise two fixed bed adsorbers 201 and 202 undergoing a cyclic operation of four steps—adsorption, blowdown, purge, and pressurization. The PSA system may be configured to receive a feed 210 and produce a product stream 211, and a PSA off gas stream 212. For improving the performance of the basic Skarstrom™ cycle (FIG. 2), additional operation steps such as pressure equalization, product pressurization, and co-current depressurization can be employed. Besides these steps, the number of beds can be modified to achieve the optimal operation and multi-bed processes can be used in commercial applications like hydrogen recovery. Similarly, a TSA system can be used where a swing in temperature causes the sorption and desorption.

PSA cycles can be used for purification of wet gases and of hydrogen. High pressure hydrogen which may be employed in processes such as hydrogenation, hydrocracking, and ammonia and methanol production can be produced by PSA beds compounded of activated carbon, zeolites and carbon molecular sieves. Other example applications include: air separation, methane enrichment, iso/normal separations, and recovery of CO and $CO_2$.

Adsorbents Including Metal Organic Frameworks (MOF)

Adsorbents can be natural or synthetic materials, such as those having amorphous or microcrystalline structure. Example adsorbents useful for large scale operation include but are not limited to activated carbon, molecular sieves, silica gels, and activated alumina. Other useful adsorbents may include pi complexation sorbents, silver and copper complexation adsorbents, zeolites, synthetic zeolites, mesoporous materials, activated carbons, high surface area coordination polymers, molecular sieves, carbon molecular sieves (CMS), silica gels, MCM, activated alumina, carbon nanotubes, pillared clays, polymeric resins, and combinations thereof.

For systems where the incoming stream is a multi-component mixture of gases and the number of compounds to be separated cannot be removed by a single adsorbent, different layers of adsorbents can be used. For example, hydrogen purification from a methane stream in a reforming operation, where $H_2$ is contaminated with $H_2O$, $CO_2$, CO, and unconverted $CH_4$, can employ activated carbon to remove $H_2O$ and $CO_2$ in combination with additional layers of different adsorbents used to increase the loading of CO.

Zeolites, molecular sieves, and carbon molecular sieves (CMS) can be used for industrial separations employing PSA. Inorganic materials, like special kinds of titanosilicates, can be used for kinetic separations.

For systems configured to separate ethane/ethylene and propane/propylene, example types of adsorbents include zeolites/molecular sieves and pi complexation sorbents. Zeolites/molecular sieves can be used for kinetic separation, such as separation based on higher diffusivity of olefins over that of paraffins. The use of 4 A zeolite is one such example. For example, a three-bed system can be used to recover olefins from a stream containing 80-85% olefins and 10-15% paraffins, using a 4 A type zeolite at elevated temperatures (e.g., the Petrofin process). Pi complexation sorbents, such as $AgNO_3/SiO_2$, can give excellent results as compared to 4 A zeolite. PSA units as discussed herein can employ a range of different sorbents, including but not limited to a zeolite/molecular sieve sorbent, a pi complexation based sorbent, a carbon molecular sieve sorbent or any other form of activated carbon, carbon nanotubes, polymeric resin based sorbents, other sorbents or combinations thereof.

Adsorbents can be selected based on a number of different criteria. Adsorbent selection criteria can include capacity for the target components (e.g., affinity for the desired components to be separated from the multi-component feed stream), selectivity between components competing for same adsorption sites, regenerability of the adsorbent, (e.g., the ability of the adsorbent to release the adsorbed target components at a reasonable pressure rate of gas diffusion into the adsorbent—this can also affect the size of the bead that is chosen and consequently the pressure drop across the bed; an insufficient diffusion rate can require smaller diameter beads that can result in higher pressure drop and hence increased operating costs), and chemical compatibility (e.g., selecting an adsorbent resistant to chemical attack that may poison or destroy the adsorbent, such as liquid hydrocarbons causing physical breakdown of the adsorbent resulting in loss of efficiency and back pressure).

Separations, such as of ethylene and propylene, can be conducted using an amorphous fluoropolymer based membrane. Facilitated transport using silver ions can selectively transport ethylene and/or propylene. The membrane can be a part of a membrane contactor system. The feed to the system can be of a low to moderate olefin concentration. The feed to the system can contain other hydrocarbons, including, but not limited to, methane, ethane, propane, butane, butenes, $C_5$ components and higher hydrocarbons. The feed can also contain $CO_2$, CO, $H_2$, and inert components, such as nitrogen.

The separation section of OCM unit can employ cryogenic distillation systems. In some cases, the distillation section can be partially or completely replaced by efficient advanced separation technologies that operate at higher/room temperatures, such as membranes or PSA. This can result in energy savings.

Among the materials used for membranes and adsorption beds, metal-organic frameworks (MOFs) can be beneficial. MOFs can comprise metal ions and organic linkers. MOFs can be highly porous sponge-like materials. The choice of metal ion and linker can define the structure and hence the properties of MOFs. MOFs can exhibit advantages of both organic and inorganic moieties. They can be more advantageous than zeolites due to their higher surface areas and higher flexibility in pore sizes (e.g., based on their synthesis). They can be better suited than typical membranes for separation since they can be more robust, more mechanically and thermally stable, and can avoid issues such as carrier poisoning or reduction of complexing agents.

The process effluent from OCM can comprise light gases, such as methane, hydrogen, carbon dioxide, ethylene, ethane, acetylene, propane, propene and $C_{4+}$ compounds. MOFs can be used to separate $C_{2+}$ compound streams from the bulk $CH_4$ and $H_2$ in effluent. MOFs can also be used to recover ethylene from a mixed stream of $C_2$ compounds, $C_3$ compounds and $C_{4+}$ compounds, remove $CO_2$, and recover hydrogen for further processing.

Different combinations of MOFs can be synthesized to provide different separation properties. MOFs can be useful in hydrocarbon separation due to their capability of separating component gases by mechanisms such as molecular sieving, characteristic gate opening pressures for different penetrant molecules or other changes in the structure of the MOFs due to adsorbent/adsorbate interactions. Without being limited by theory, adsorption selectivity can arise from interactions using it-complexation between the double bond in ethylene molecules and partial positive charges of co-ordinatively unsaturated metal ions (e.g., Cu(II)). MOFs such as HKUST-1 can be used to separate ethylene from ethane. Other MOFs capable of separating ethylene over ethane include $Ag^+$ based MOFs, $Co_2$(2,5-dihydroxyterephthalate, or "dhtp"), and $Mg_2$(dhtp). MOFs such as ZIF-7, ZIF-8, and ZIF-4 can be used for selective adsorption of paraffins (e.g., ethane) over ethylene due to the gate-opening effect or the breathing behavior of the MOF. ZIF-8 can adsorb alkanes (e.g., methane) over alkenes (e.g., ethylene). The selectivity of this separation can be controlled by adjusting the hydration level of the MOF. MOFs such as ZIF-67, SBMOF-1, SBMOF-2, Cu-TDPAT, USTA-33a, ZJU-61, USTA-33, USTA-10a can be used for selective separation of methane from other hydrocarbons such as $C_2$ compounds. The MOF $M_2$(dobdc) can be used to effectively separate acetylene, ethylene, ethane, and methane collectively or individually from their mixtures. The $M_2$(dobdc) can be in the meta form $M_2$(m-dobdc) or the para form $M_2$(p-dobdc). The metal can be any suitable metal such as iron (Fe), nickel (Ni), manganese (Mn) or cobalt (Co). Further information on these MOFs can be found in PCT Publication No. WO 2015/066693A1, which is incorporated herein by reference in its entirety. IRMOFs, such as MOF-5, can be used for separation of hydrogen from hydrogen/methane and hydrogen/$C_2$ mixtures. RPM3-Zn can be used to separate $C_1$-$C_4$ paraffins. MOFs such as UTSA-100, SIF SIX, ZJU-5 can be utilized for acetylene removal from the olefins stream where back-end acetylene removal is used rather than acetylene hydrogenation. MOFs such as M-(dobdc) can be modified with amines to selectively remove $CO_2$. Several MOFs such as ZIF-68-70, 78, 79, 81 82, MOF-11, MOF-508b, PCN-60, 61, MIL-100, MIL-101, ZIF-8, SNU-9, MIL-102(Cr), MIL-53(Cr) have been studied for removal of $CO_2$ from methane and nitrogen and can be utilized for, e.g., a front end $CO_2$ removal system. MOFs such as $M_2$(dobpdc) can be used to remove $CO_2$ from other gases and can be used for $CO_2$ removal front or back of the OCM process described herein. MOFs such as Fe-BTTri can be used for CO removal from various components such as $CO_2$, $N_2$, $CH_4$ and can be used for back end CO removal in the OCM unit.

MOFs can be used in the adsorbent beds of PSA/TSA system or as a part of membrane based applications. As part of membrane systems, they can be incorporated in thin film membranes or mixed matrix membranes (MMMs). With MMMs, MOFs have shown improved gas separation qualities, with increased permeability and selectivity using MMMs. Mixed matrix membranes can combine the advantages of easy and cheap fabrication of polymer membranes with the improved gas separation properties of different MOFs.

OCM and/or ETL Systems with Adsorptive Separation

PSA technology can be applied to processes including those involving a hydrocarbon stream containing a mix of the following hydrogen, carbon dioxide, carbon monoxide, methane, ethane, ethylene, propane, propylene, butanes, butenes and/or other higher hydrocarbons needing to be purified or separated into desirable products (e.g., ethylene, methane, hydrogen, or propylene).

Hydrocarbon streams can be produced via traditional refining and petrochemical processes. Hydrocarbon streams can be produced from OCM or ETL reactor systems.

The present disclosure provides the use of PSA in processes and systems for oxidative coupling of methane (OCM) and ethylene-to-liquids (ETL) operations, and the application of adsorbent based processes used in conjunction with OCM and ETL processes to generate significant process improvements and enhance the economic value of the processes. OCM systems are described in, for example, U.S. Patent Publication No. US 2015/0210610, which is entirely incorporated herein by reference. ETL systems are described in, for example, U.S. Patent Publication No. 2015/0232395, which is entirely incorporated herein by reference.

Figure 3:
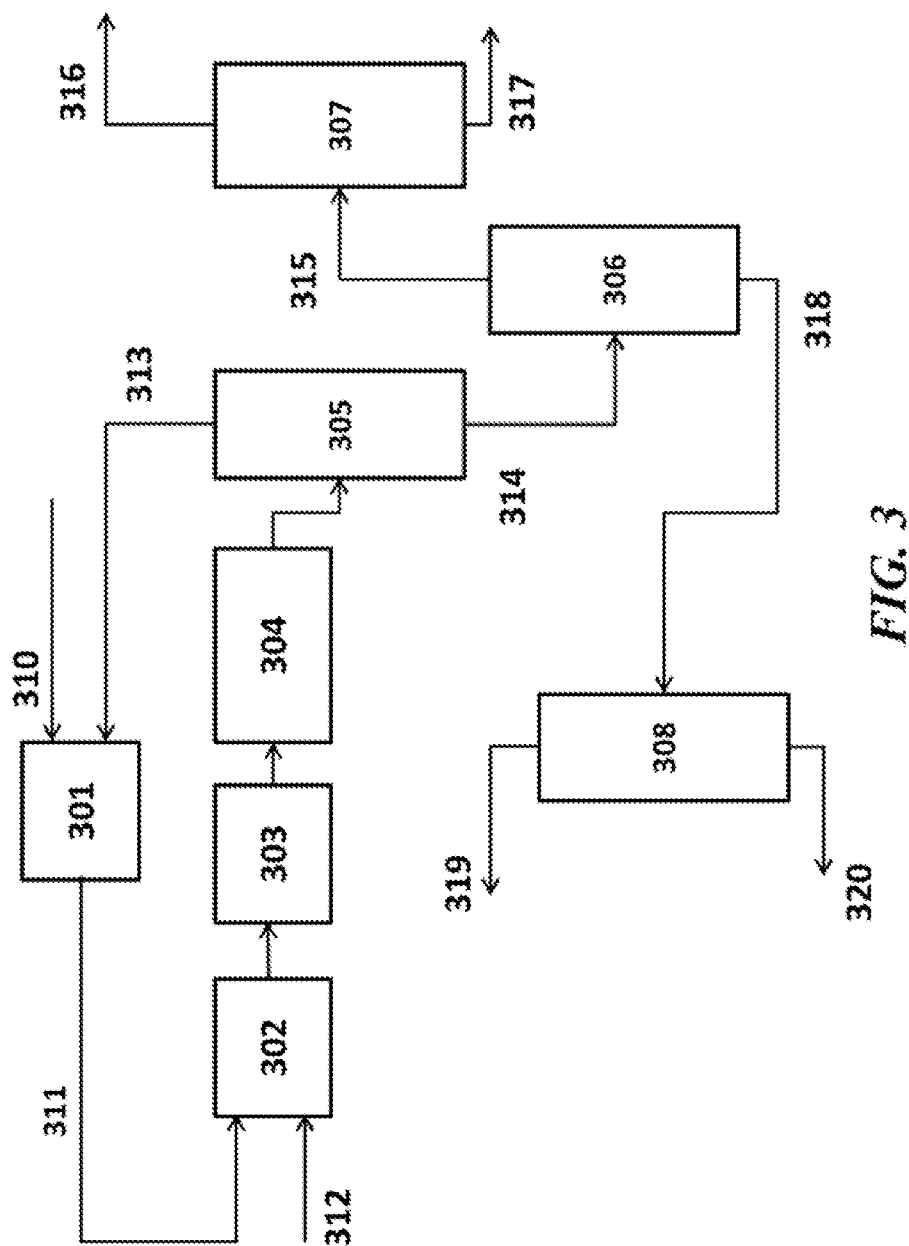
FIG. 3 shows an example of an OCM system of the present disclosure.

An OCM system, such as that shown in FIG. 3, can include an OCM or OCM-post-bed-cracking (PBC) reactor 302, a process gas compression system 303, a process gas treatment system 304, a cryogenic separations system, and a methanation system 301. The feed to the OCM system can be an oxygen feed 312 and a methane source feed 311 (such as a natural gas feed stream or other methane source). In some cases, additional ethane feed can be supplied to the PBC section of the OCM reactor, where paraffins such as ethane in the OCM product stream and/or additional ethane can be cracked to olefins such as ethylene. The separations sub-system can comprise a series of fractionation towers, like a demethanizer 305, deethanizer 306, $C_2$ splitter 307, depropanizer 308, debutanizer, and others. Overhead 313 from the demethanizer can be directed into the methanation system along with hydrogen or natural gas 310 to produce additional methane. The bottoms stream 314 from the demethanizer can be directed to the deethanizer. The overhead stream 315 from the deethanizer can be directed to the $C_2$ splitter, and there split into ethylene 316 and ethane 317 streams. The bottoms stream 318 from the deethanizer can be directed to the depropanizer, and there split into a $C_3$ product stream 319 and a $C_{4+}$ product stream 320. The cryogenic separations system can comprise additional ethylene and propylene refrigeration sub-systems to provide for the chilling requirements of the system.

Figure 4:
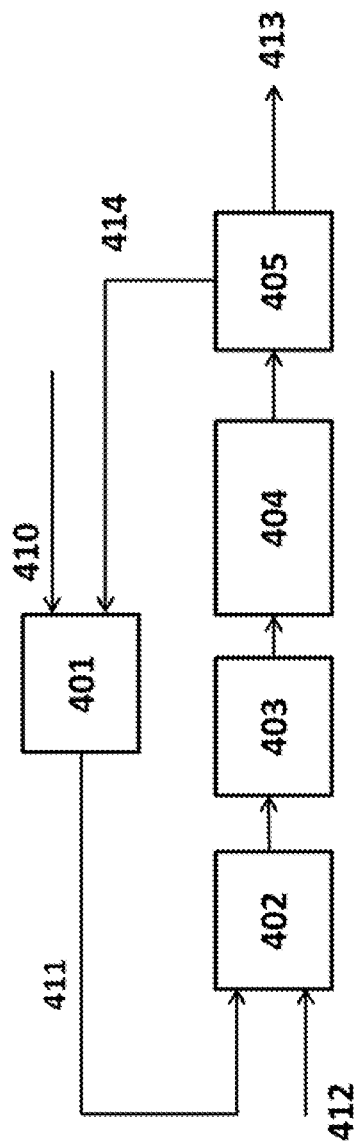
FIG. 4 shows an example of an OCM system of the present disclosure with a single stage PSA unit.

Stand-alone OCM processes can use adsorptive separation. In certain cases, the separations section of the OCM system can be eliminated, or partially eliminated, by utilizing an advanced separations method as discussed in this application. The advanced separation method can be a PSA unit or a membrane based method, or a cryogenic system. FIG. 4 shows an example schematic of OCM with a PSA unit. The PSA unit can separate methane, $CO_2$, CO, and/or $H_2$ from ethane, ethylene, propane, propylene, and/or higher hydrocarbons. Methane 411 and oxygen 412 can be directed into an OCM reactor 402 and reacted to produce higher hydrocarbon products including ethylene. The OCM product can be compressed in a process gas compression system 403, treated in a process gas treatment system 404, and separated in the PSA 405 into a product stream 413 and a recycle stream 414. The recycle stream can be directed to a methanation unit 401, which can also receive a natural gas stream 410 and produce methane for the OCM reactor. The extent of separation and degree of recovery can depend on e.g., the type of adsorbent(s), pressure differential, and number of PSA stages employed. The feed to the PSA unit can have one or more of the following components: $H_2$, $N_2$, $O_2$, CO, $CO_2$, $CH_4$, ethane, ethylene, acetylene, propane, propylene, butanes, butenes, butadiene, water, and higher paraffinic and/or olefinic components. The PSA product gas can comprise components including but not limited to: $H_2$, $N_2$, CO, $CO_2$, $CH_4$, $O_2$, ethane, ethylene and acetylene. PSA product gas can comprise components from about 0% to about 99.99% recovery. The PSA tail gas can comprise less than or equal to about 99.99%, 90%, 80%, 70%, 60%, 50% or less ethylene. The PSA tail gas can comprise greater than or equal to about 10%, 20%, 30%, 40%, 50%, 60%, 70%, 80%, 90%, 99.99% or more ethylene. The PSA tail gas can comprise about less than or equal to about 99%, 90%, 80%, 70%, 60%, 50%, 40%, 30%, 20%, 10%, 1% or less ethane. The PSA tail gas can comprise greater than or equal to about 0.1%, 1%, 10%, 20%, 30%, 40%, 50%, 60%, 70%, 80%, 90%, 99% or more ethane. The PSA tail gas can comprise less than or equal to about 90%, 80%, 70%, 60%, 50%, 40%, 30%, 20%, 10%, 1% or less methane, hydrogen, acetylene, $N_2$, $O_2$, $H_2O$ and/or $CO_2$. The PSA tail gas can comprise greater than or equal to about 0.1%, 1%, 10%, 20%, 30%, 40%, 50%, 60% methane, hydrogen, acetylene, $N_2$, $O_2$, $H_2O$ and/or $CO_2$. Based on the process configuration, including the type of adsorbents employed, pressure differential and the operation, various different recoveries are possible.

As discussed above, the PSA unit can comprise one or more adsorbent materials that can be suitable to achieve the component recoveries. The sorbent can be a zeolite/molecular sieve based be a mesoporous material, a carbon based sorbent, or a it-complexation sorbent. In some cases the sorbent material can be a polymeric resin, carbon nanotubes, and carbon fibers. The PSA unit can be configured to have layers of different sorbents so as to result in high recoveries from the multi-component feed streams to the desired products.

Figure 5:
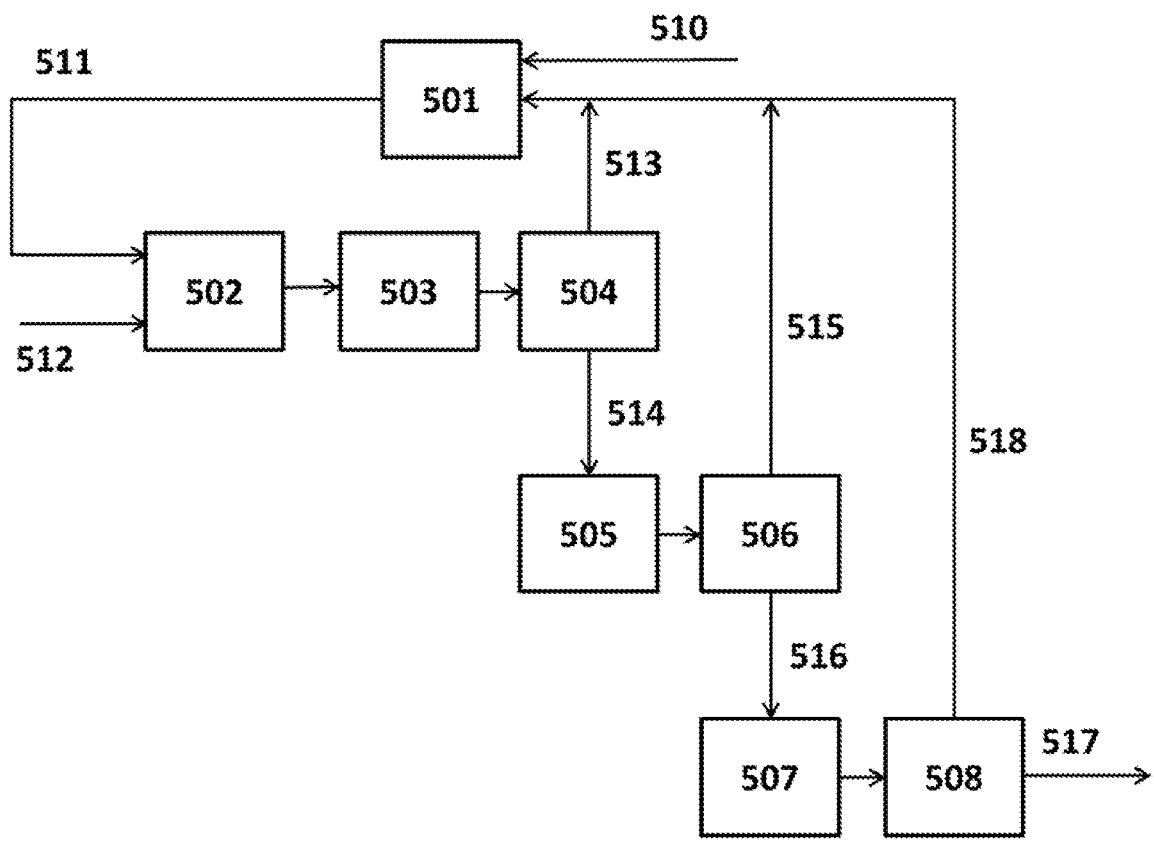
FIG. 5 shows an example of an OCM system of the present disclosure with a multi stage PSA unit.

In certain cases the PSA can be a multi stage unit (see, e.g., FIG. 5). In such a unit, an OCM reactor 502 can receive a methane stream 511 and an oxygen stream 512, and react the methane and oxygen to produce higher hydrocarbon products including ethylene in an OCM product stream. The OCM product stream can be compressed in a first compressor 503 and directed to a first PSA separation 504. The tail gas 514 from the first PSA can be compressed in a second compressor 505 and fed to a second PSA separation 506, the tail gas 516 from which can be compressed in a third compressor 507 and separated in a third PSA separation 508. The tail gas from the third PSA can be the final purified stream 517 containing ethylene up to 99.9% purity. PSA product streams 513, 515, and 518 can be directed to recycle, such as via a methanation unit 501 along with a natural gas stream 510. Each PSA stage can be a dual-bed PSA or a multi-bed PSA system.

In certain cases, the process requirements can dictate that only a limited amount of recovery is required in the PSA unit and subsequent recovery and purification is performed in a fractionation column or the gas is a feed for a downstream process unit. The downstream process unit can be an ETL system, an ethylene steam cracker system, a gas processing plant, NGL extraction plant, a refinery off-gas separations system, or other process unit.

OCM process retrofits can use adsorptive separation. OCM can be employed to convert a feedstock comprising methane to ethylene and other olefins. Historically, ethylene has been produced via steam cracking of gaseous or liquid hydrocarbon feedstocks like ethane, propane, LPG, or naphtha. As in most of the refining and petrochemical operations, a steam cracking operation can involve a cryogenic fractionation or a separations section that consists of a series of fractionation columns to successively recover various components at high product purity.

The present disclosure includes the application of PSA processes to an OCM retrofit of an existing ethylene cracker (e.g., steam cracker).

Figure 13:
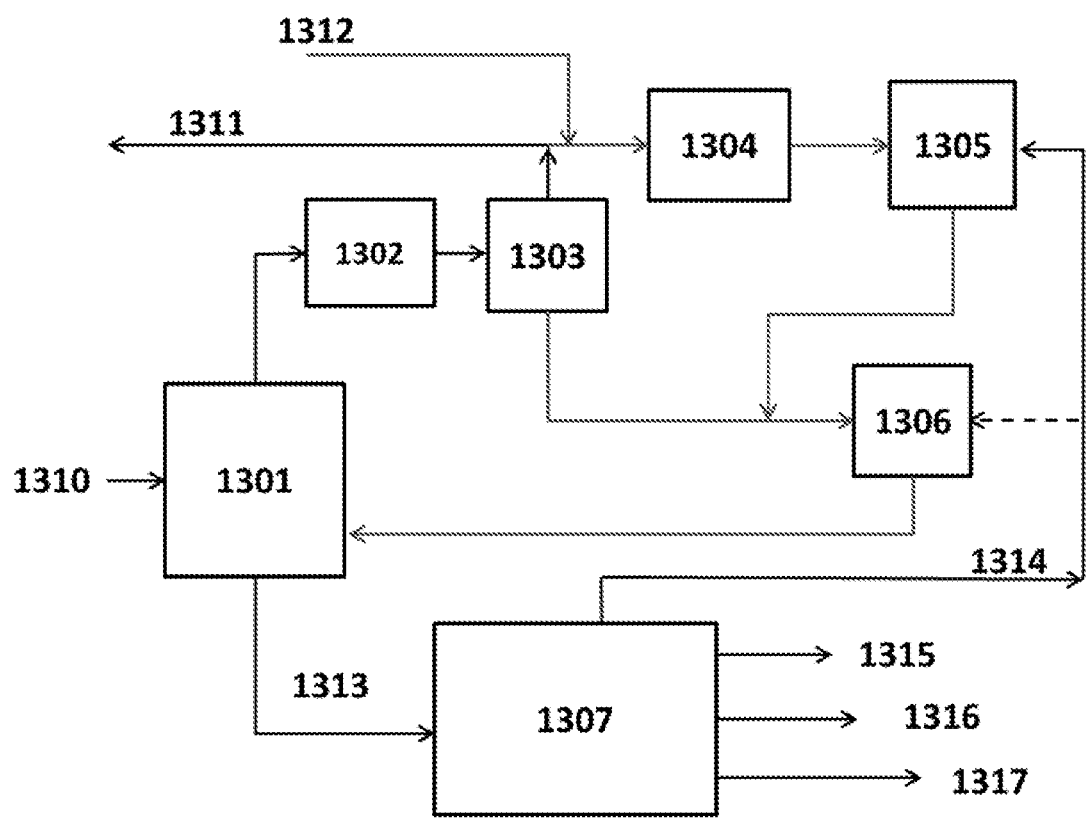
FIG. 13 shows an example system of the present disclosure using an alternate scheme for a PSA unit integrated with an OCM-ETL system for a refining application.

An example application for OCM combined with a PSA unit involves an existing petrochemical plant such as a steam cracker is considering low cost ways to add ethylene capacity. An example revamp to add capacity may include addition of, or debottlenecking of, the existing fractionation towers for the entire flow addition for the revamp. However, as shown in FIG. 13, the use of a PSA unit as disclosed herein can provide a low cost alternative to traditional revamps. An OCM unit with a PSA unit retrofitted to an existing steam cracker can be an effective way of adding ethylene capacity at a low marginal cost. The advantages of adding a PSA unit may include that no additional cryogenic separation is required for the added capacity. For ethylene revamps, one of the key areas during debottlenecking may be the refrigeration systems and/or the fractionation columns, but utilizing the PSA to separate or pre-separate the additional product stream can result in a simpler and easier debottlenecking. As in shown in FIG. 13, for example, the tail gas from the PSA can be sent to the cracker system where the ethylene is recovered.

Figure 6:
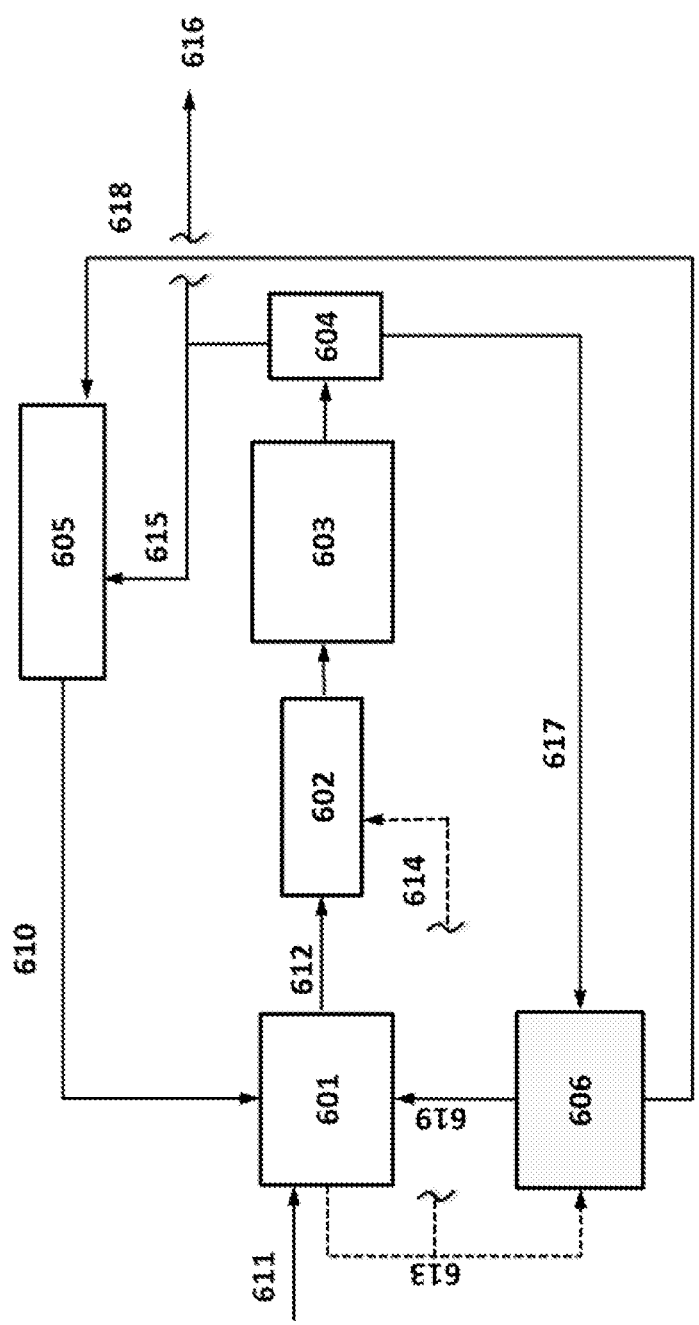
FIG. 6 shows an example system of the present disclosure using a retrofit of OCM to a cracker, with a single stage PSA unit.

FIG. 6 shows an example of an OCM process integrated with an existing ethylene cracker using a PSA system for separations. The OCM reactor 601 takes in methane 610 and oxygen 611 and produces an OCM effluent 612 having $CO_2$, $CH_4$ and $C_2H_4$, in some cases amongst other components, such as $H_2$ and CO. The OCM reaction can be exothermic and can produce steam 613. The OCM effluent can be compressed in a compressor 602 and optionally treated in an acid gas removal system 603, and fed into a pressure swing adsorption (PSA) unit 604. In some cases the acid gas removal system may have an additional knock out drum to condense and separate any condensates and water. It also can include a drier to remove water. The PSA unit can produce a product stream that can include $H_2$, $CH_4$, ethane, $CO_2$ and CO. The overhead stream 615 can be fed into a methanation subsystem 605 (e.g., methanation reactor) to provide methane for the OCM reactor, and some of the overhead stream can be purged 616 to a fuel gas system, for example. Additional methane can be provided by way of a natural gas stream or other methane stream. The PSA tail gas 617 can comprise most of the ethylene, the content of which may range from about 50% to about 99.9% depending on the process configuration and operation of the PSA system. The PSA tail gas can also comprise $H_2$, CO, $CO_2$, $CH_4$, ethane, propane, propylene, butanes, butenes, and other components. The process of FIG. 6 can further include an existing ethylene cracker 606. The PSA tail gas can be fractionated using existing separations capacity in the ethylene cracker. The heavy components can be processed in the fractionation towers of the ethylene cracker, optionally first being compressed in the existing process gas compressor of the ethylene cracker. In some cases, the heavy components stream can be routed to the $CO_2$ removal unit of the existing ethylene cracker subsystem to meet the $CO_2$ specification. The OCM reactor can receive a $C_2$ recycle stream 619 from the cracker complex.

The combination of an OCM unit and an existing ethylene cracker can provide synergistic benefits. It can provide for a low cost alternative to add ethylene capacity to the existing cracker. In some cases, prior to retrofit of an ethylene cracker with OCM, the entire overhead from the existing demethanizer is used as fuel gas, and can now be available as one of the feeds to the methanation unit. In some cases, the demethanizer overhead off-gas comprises up to about 80%, 85%, 90%, 95%, or more methane, which can be converted to ethylene in the OCM reactor, hence increasing the total ethylene capacity. In some cases, the hydrogen content in the existing demethanizer overhead is substantial, and may be enough to meet the hydrogen requirement of the methanation unit.

In some cases, retrofitting an ethylene cracker with OCM reduces (or allows for reduction of) the severity of cracking in the existing cracker, enabling value addition by increasing the production of pyrolysis gasoline components in the cracker effluent, as the OCM reactor produces the ethylene that may be needed to achieve the total system capacity. The cracker can then be operated on high propylene mode to produce more propylene and at the same time meeting the ethylene production rate by the new OCM unit. This retrofit can result in greater flexibility for the ethylene producer with respect to the existing cracker operation.

In some instances, the overall carbon efficiency can be increased as the methane and hydrogen from the existing demethanizer off-gases can be utilized to convert the carbon dioxide and carbon monoxide to methane, which is fed to the OCM reactor.

In some instances, ethane and/or propane recycle streams from the existing cracker can be routed to the OCM unit (e.g., instead of the cracking furnaces). These recycle streams are typically routed to the cracking furnaces where they are cracked to extinction. This can provide an advantage over routing the recycle streams to OCM over the cracking furnace, such as higher selectivity to ethylene in the OCM process.

Figure 7:
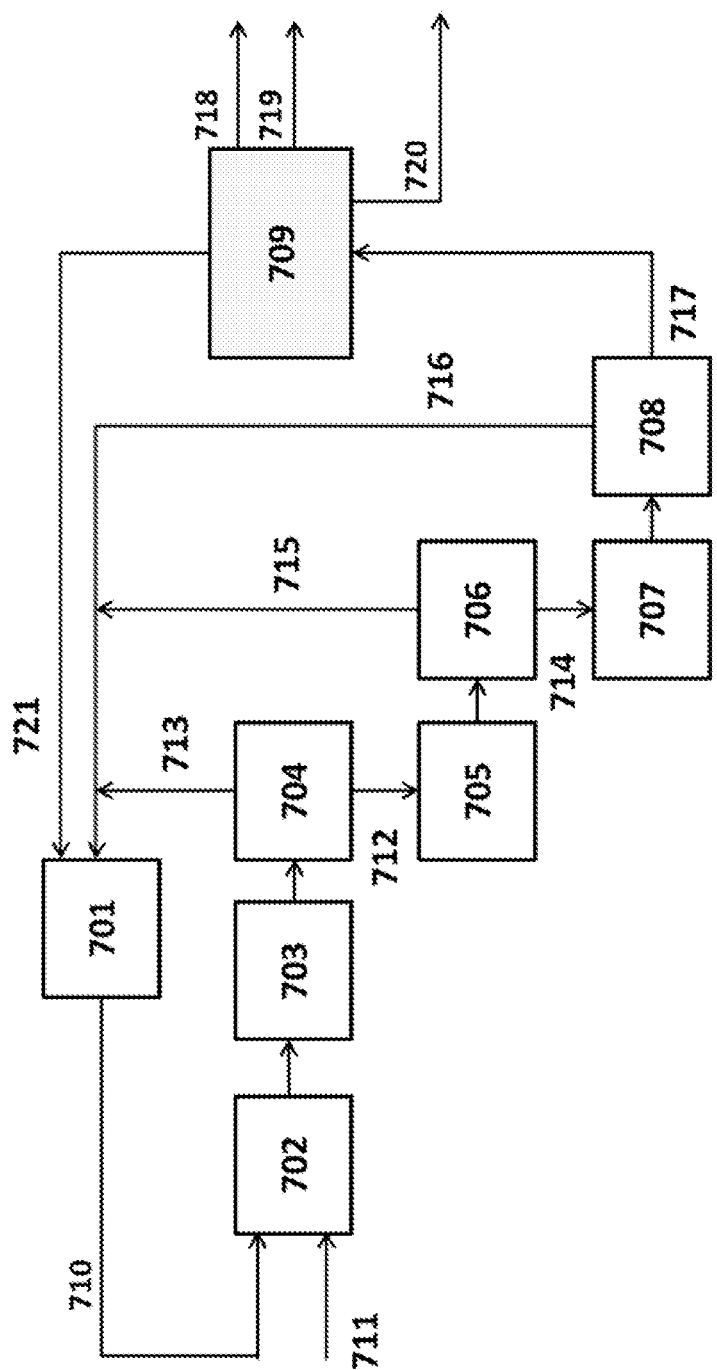
FIG. 7 shows an example system of the present disclosure using a retrofit of OCM to a cracker, with a multi stage PSA unit.

In certain cases, more than one stages or PSA columns may be employed to achieve higher recovery and higher product purity. As in shown FIG. 7, for example, up to 99.9% recovery is possible using the multi stage PSA units. An OCM reactor 702 can receive a methane stream 710 and an oxygen stream 711, and react the methane and oxygen to produce higher hydrocarbon products including ethylene in an OCM product stream. The OCM product stream can be compressed in a first compressor 703 and directed to a first PSA separation 704. The tail gas 712 from the first PSA can be compressed in a second compressor 705 and fed to a second PSA separation 706, the tail gas 714 from which can be compressed in a third compressor 707 and separated in a third PSA separation 708. The tail gas from the third PSA can be the final purified stream 717 can be directed to a cracker unit, such as an existing cracker unit, where it can be processed and separated into an ethylene product stream 718, a propylene product stream 719, and an additional product stream 720. PSA product streams 713, 715, and 716 can be directed to recycle, such as via a methanation unit 701, along with a demethanizer off gas stream 721 from the cracker unit. Each PSA stage can be a dual-bed PSA or a multi-bed PSA system.

The application of a PSA unit to OCM systems, standalone or retrofits to existing facilities exhibits immense potential in terms of cost savings and ease of integration and retrofit to existing facilities.

Figure 8:
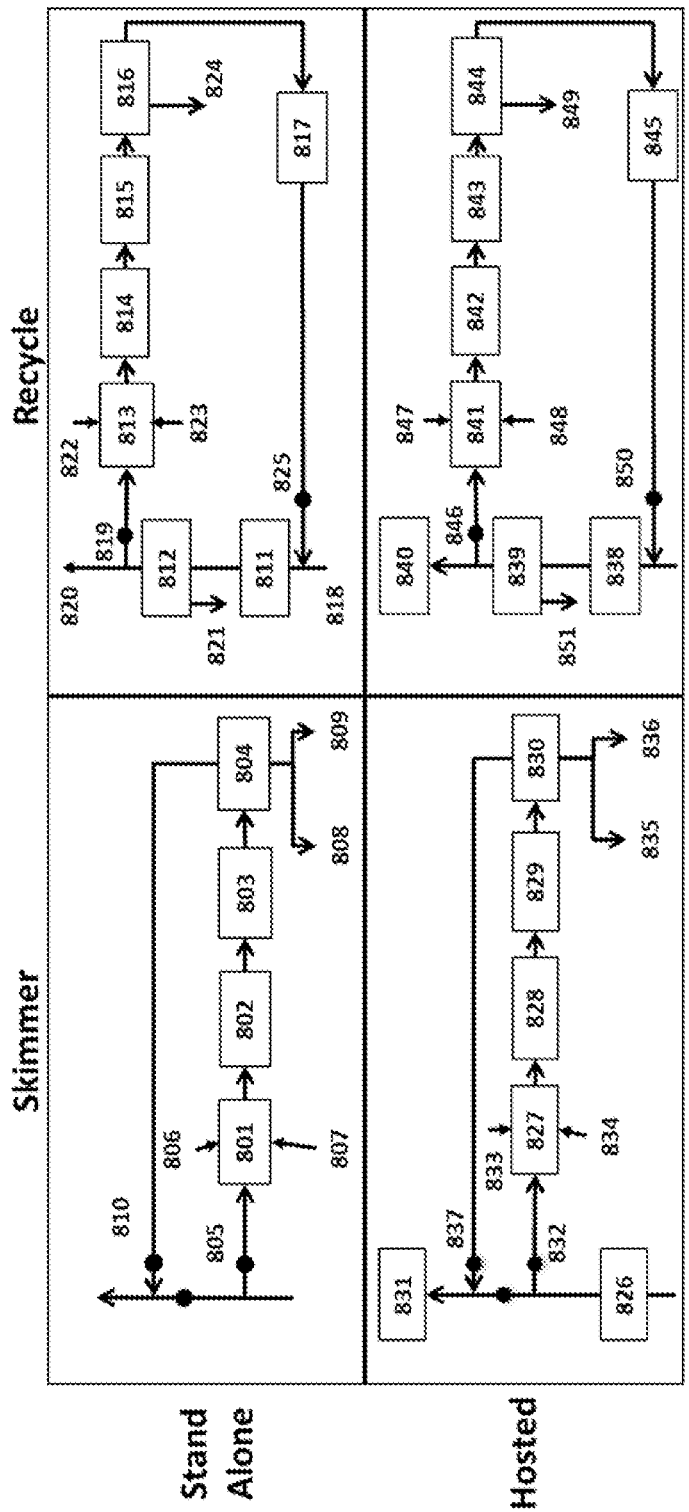
FIG. 8 shows configurations of an example system of the present disclosure using ethylene to liquids (ETL) systems without PSA.

ETL processes can use adsorptive separation. FIG. 8 shows various example configurations for an OCM-ETL process. In the upper left, FIG. 8 shows a standalone skimmer configuration, where a methane stream 805 can be directed into an OCM reactor 801 with an oxygen feed 806 and optionally an ethane feed 807. The OCM product stream can be directed into a compressor 802 and then into an ETL reactor 803. The ETL product stream can be directed into a gas separations unit 804, where it can be separated into a $C_{2+}$ product stream 808, a $C_{5+}$ product stream 809, and an overhead stream 810 comprising methane which can be returned to a pipeline, sold to a consumer, or otherwise used. In the upper right, FIG. 8 shows a standalone recycle configuration, where a methane feed stream 818 (e.g., from a natural gas pipeline) is directed into a treatment unit 811 and then into a separations system (e.g., cryogenic) 812. A methane feed stream 819 can be directed to an OCM reactor 813, while another methane stream 820 can be purged or used for power generation. A $C_{2+}$ stream 821 can also be recovered from the separations system. An oxygen feed stream 822 and optionally an ethane stream 823 can also be directed into the OCM reactor, and the reactor can produce an OCM product stream. The OCM product stream can be directed into a compressor 814 and then into an ETL reactor 815. The ETL product stream can be processed in a knockout drum 816 or other separator to remove a $C_{5+}$ product stream 824. The remaining ETL product stream can be directed to a compressor 817 and recycled to the treatment unit. In the lower left, FIG. 8 shows a hosted skimmer configuration, where a methane stream 832 can be directed from a separations system 826 (e.g., cryogenic) into an OCM reactor 827 with an oxygen feed 833 and optionally an ethane feed 834. The OCM reactor product stream can be directed into a compressor 828 and then into an ETL reactor 829. The ETL product stream can be directed into a gas separations unit 830, where it can be separated into a $C_{2+}$ product stream 835, a $C_{5+}$ product stream 836, and an overhead stream 837 comprising methane which can be returned to a recompressor 831. In the lower right, FIG. 8 shows a hosted recycle configuration, where a methane stream is directed into a treatment unit 838 and then into a separations system (e.g., cryogenic) 839. A methane feed stream 846 can be directed to an OCM reactor 841, while another methane stream can be directed to a recompressor 840. A $C_{2+}$ stream 851 can also be recovered from the separations system. An oxygen feed stream 847 and optionally an ethane stream 848 can also be directed into the OCM reactor, and the reactor can produce an OCM product stream. The OCM product stream can be directed into a compressor 842 and then into an ETL reactor 843. The ETL product stream can be processed in a knockout drum 844 or other separator to remove a $C_{5+}$ product stream 849. The remaining ETL product stream can be directed to a compressor 845 and recycled 850 to the treatment unit.

Figure 9:
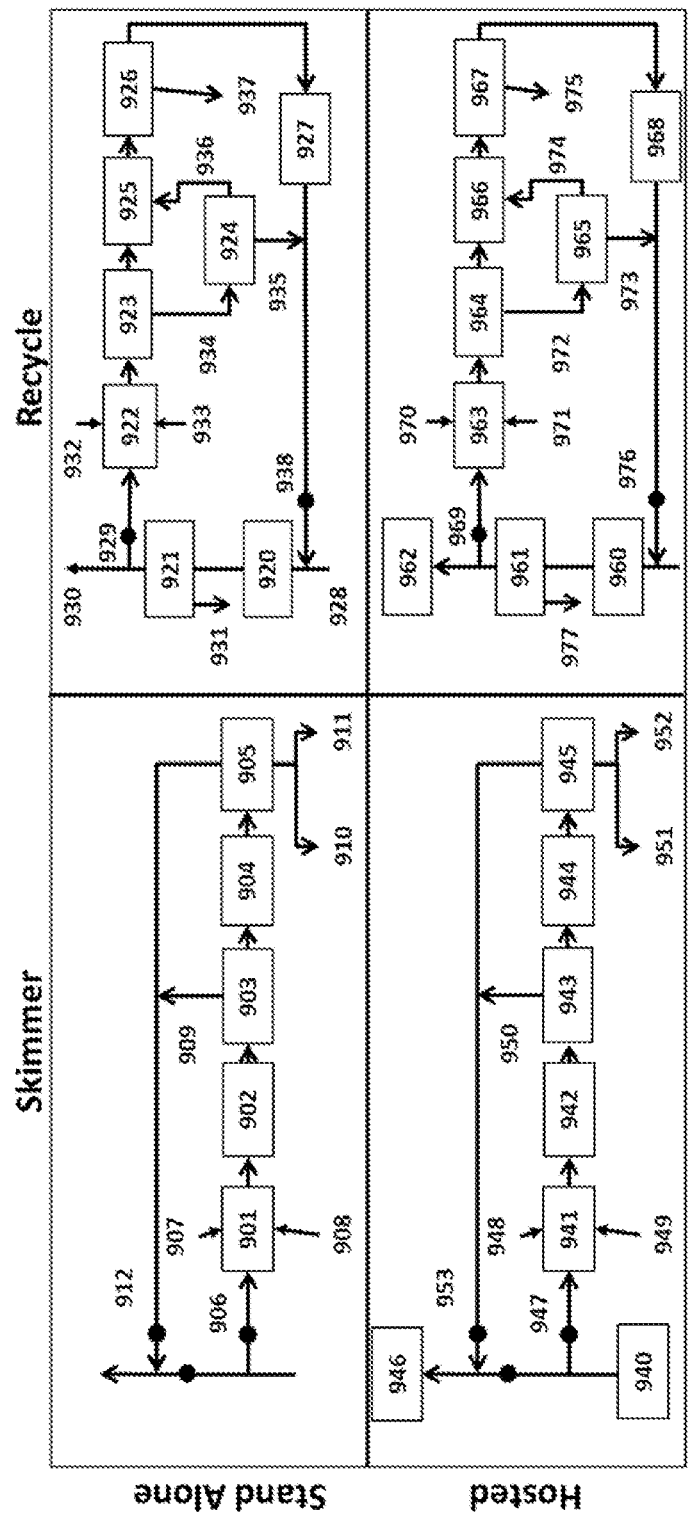
FIG. 9 shows configurations of an example system of the present disclosure using ETL systems with PSA.

FIG. 9 shows similar configurations as FIG. 8, with an added pressure swing adsorption (PSA) unit to pre-separate the OCM effluent to remove most of the methane, hydrogen, CO and $CO_2$ from the olefinic stream, which is then fed to the ETL reactor. This can result in a feed to the ETL reactor that is concentrated in olefins. Though the process remains similar, the entire ETL and separations train becomes considerably smaller; that is, larger capacities can be achieved in the same set-up or same footprint. In some cases this can improve the ETL reaction operation. In the upper left, FIG. 9 shows a standalone skimmer configuration, where a methane stream 906 can be directed into an OCM reactor 901 with an oxygen feed 907 and optionally an ethane feed 908. The OCM reactor product stream can be directed into a compressor 902 and then into a PSA unit 903. A light stream 909 comprising methane, hydrogen, CO and $CO_2$ can be directed from the PSA back to a pipeline, sold to a consumer, or otherwise used. An olefinic stream can be directed from the PSA to an ETL reactor 904. The ETL product stream can be directed into a gas separations unit 905, where it can be separated into a $C_{2+}$ product stream 910, a $C_{5+}$ product stream 911, and an overhead stream 912 comprising methane which can be returned to a pipeline, sold to a consumer, or otherwise used. In the upper right, FIG. 9 shows a standalone recycle configuration, where a methane feed stream 928 (e.g., from a natural gas pipeline) is directed into a treatment unit 920 and then into a separations system (e.g., cryogenic) 921. A methane feed stream 929 can be directed to an OCM reactor 922, while another methane stream 930 can be purged or used for power generation. A $C_{2+}$ stream 931 can also be recovered from the separations system. An oxygen feed stream 932 and optionally an ethane stream 933 can also be directed into the OCM reactor, and the reactor can produce an OCM product stream. The OCM product stream can be directed into a compressor 923, and at least a portion 934 of the OCM product stream can be directed from the compressor into a PSA unit 924. A light stream 935 comprising methane, hydrogen, CO and $CO_2$ can be directed from the PSA back to the treatment unit. An olefinic stream 936 can be directed from the PSA to an ETL reactor 925. The ETL product stream can be processed in a knockout drum 926 or other separator to remove a $C_{5+}$ product stream 937. The remaining ETL product stream can be directed to a compressor 927 and recycled to the treatment unit. In the lower left, FIG. 9 shows a hosted skimmer configuration, where a methane stream 947 can be directed from a separations system 940 (e.g., cryogenic) into an OCM reactor 941 with an oxygen feed 948 and optionally an ethane feed 949. The OCM reactor product stream can be directed into a compressor 942 and then into and then into a PSA unit 943. A light stream 950 comprising methane, hydrogen, CO and $CO_2$ can be directed from the PSA to a recompressor 946. An olefinic stream can be directed from the PSA to an ETL reactor 944. The ETL product stream can be directed into a gas separations unit 945, where it can be separated into a $C_{2+}$ product stream 951, a $C_{5+}$ product stream 952, and an overhead stream 953 comprising methane which can be returned to the recompressor. In the lower right, FIG. 9 shows a hosted recycle configuration, where a methane stream is directed into a treatment unit 960 and then into a separations system (e.g., cryogenic) 961. A methane feed stream 969 can be directed to an OCM reactor 963, while another methane stream can be directed to a recompressor 962. A $C_{2+}$ stream 977 can also be recovered from the separations system. An oxygen feed stream 970 and optionally an ethane stream 971 can also be directed into the OCM reactor, and the reactor can produce an OCM product stream. The OCM product stream can be directed into a compressor 964 and at least a portion 972 of the OCM product stream can be directed from the compressor into a PSA unit 965. A light stream 973 comprising methane, hydrogen, CO and $CO_2$ can be directed from the PSA back to the treatment unit. An olefinic stream 974 can be directed from the PSA to an ETL reactor 966. The ETL product stream can be processed in a knockout drum 967 or other separator to remove a $C_{5+}$ product stream 975. The remaining ETL product stream can be directed to a compressor 968 and recycled 976 to the treatment unit.

The ETL reactor can be a tubular, packed bed, moving bed, fluidized bed, or other reactor type. An ETL reactor can be an isothermal or adiabatic reactor. The ETL system can benefit from a feed concentrated in olefins. The ETL reactor system can use a recycle stream to control and moderate the temperature increase in the reactor bed due to the highly exothermic nature of the ETL reactions. ETL systems are described in, for example, U.S. Patent Publication No. 2015/0232395, which is entirely incorporated herein by reference.

In some cases, one or more of the fractionation towers can be deemed redundant if using the PSA, as an example, a demethanizer may not be required and the sales gas or purge gas to fuel can be sent from the PSA itself.

Retrofit applications for midstream and refining processes can use adsorptive separation. Systems, such as those of FIG. 10, can be integrated with an existing gas processing plant where one or more of the existing subsystems can be utilized. The utilization may arise from the fact that the existing subsystems are no longer used, or have an additional capacity available to allow for the integration.

Figure 10:
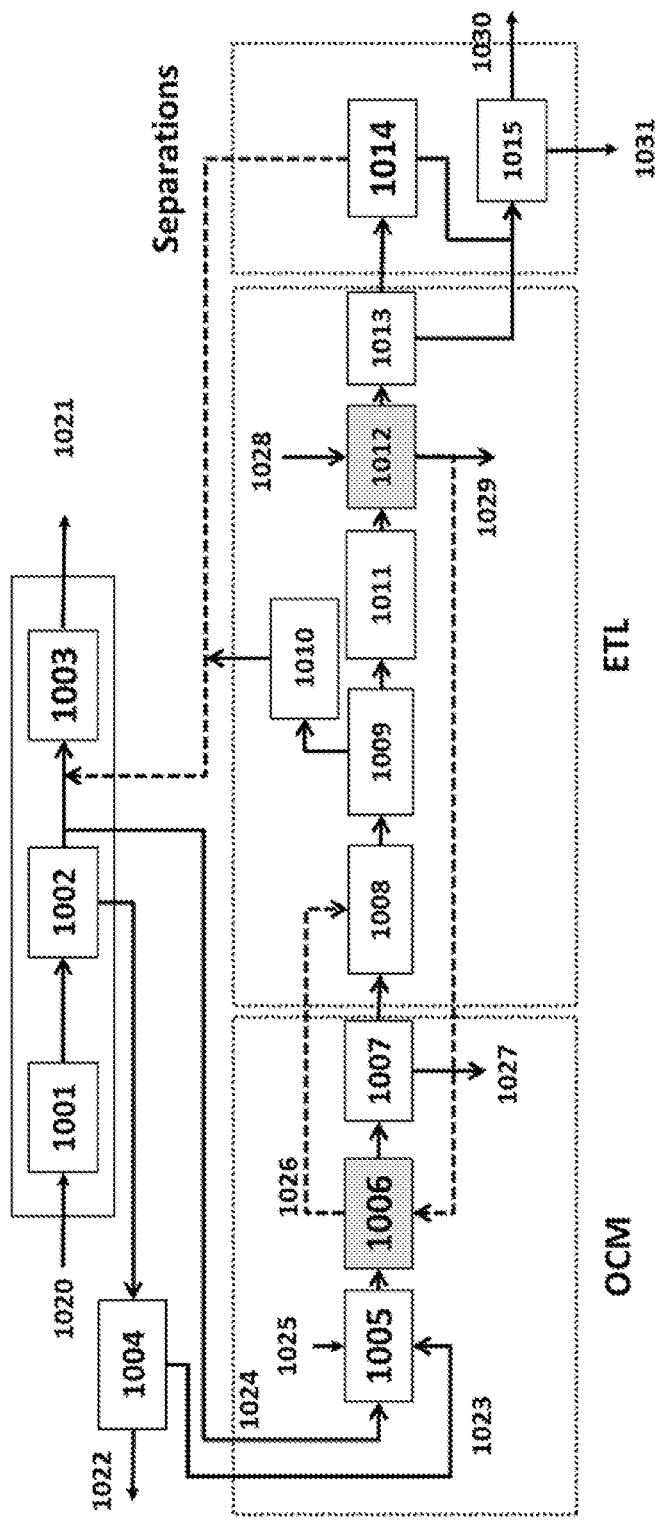
FIG. 10 shows an example system of the present disclosure using a PSA unit integrated with an OCM-ETL system for a midstream application.

FIG. 10 shows an example application of an OCM-ETL system using a PSA system for pre-separations to an existing gas processing plant, where one or more existing sub systems may be utilized. As shown in FIG. 10, the existing separations sub-system can be integrated with the OCM-ETL system to add value by converting natural gas to higher value liquid hydrocarbons. The PSA unit can be used to pre-separate the lighter components like methane, hydrogen, carbon monoxide, carbon dioxide, ethane, and other components, and the olefin rich stream can be sent to the ETL reactor that converts the olefins to higher molecular weight liquid hydrocarbons. One advantage of using a PSA system is the reduction in net additional feed to the existing separation system, which can be de-bottlenecked easily. If the separation system is no longer in use, addition of a PSA can bring about larger total capacities that can be achieved by adding larger OCM-ETL systems. A natural gas stream 1020 can be directed to a treatment unit 1001 and then into a separations system (e.g., cryogenic) 1002. At least portion of a methane stream 1024 from the separations unit can be directed to an OCM reactor 1005, while a portion of the methane stream can be directed to a compressor 1003 and used as sales gas 1021 or other purposes. A higher hydrocarbon stream can be directed from the separations system to a $C_2$ removal unit 1004, which can produce a natural gas liquids stream 1022 and a $C_2$ stream 1023. The $C_2$ stream can be fed into the OCM reactor with the methane stream and an oxygen stream 1025, and reacted to form higher hydrocarbon products including ethylene. The OCM product stream can be directed into a heat recovery system 1006, which can generate a high pressure superheated (HPSH) steam stream 1026. The OCM product stream can then be directed to a knockout drum to recover a condensate stream 1027. The OCM product stream can then be directed to a compressor 1008, which can operate using the HPSH steam stream. From the compressor, the OCM product stream can be directed to a PSA unit 1009. From the PSA unit, light stream comprising methane, hydrogen, CO and $CO_2$ can be directed to a methanation unit 1010, and an olefinic stream can be directed to an ETL reactor 1011 and reacted to form higher hydrocarbon products. The ETL product stream can be directed to a heat recovery unit 1012, where boiler feed water (BFW) 1028 can be heated, at least a portion of which can be fed 1029 to the heat recovery unit 1006. The ETL product stream can then be directed to another knockout drum 1013. The overhead stream from the knockout drum can be directed to a low temperature separations unit 1014, while the bottoms stream from the knockout drum can be directed to a $C_4$ removal unit 1015, which can produce a $C_4$ stream 1030 and a $C_{5+}$ stream 1031. Overhead from the low temperature separations unit, as well as product from the methanation reactor, can be directed back to the compressor 1003.

Figure 11:
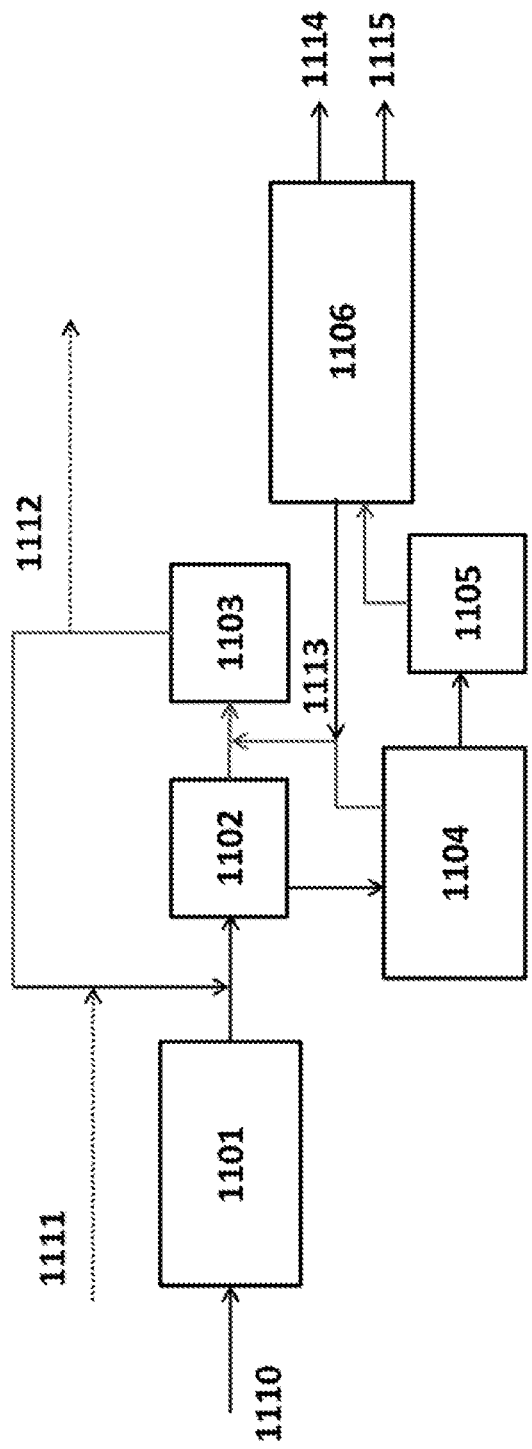
FIG. 11 shows an example system of the present disclosure using a PSA unit integrated with an OCM-ETL system in a natural gas liquids (NGL) application.

OCM-ETL systems of the present disclosure can be integrated into and combined into conventional natural gas liquids (NGL) extraction and NGL fractionation sections of a midstream gas plant. Where NGLs in the gas stream are declining (or gas is dry), the deployment of OCM-ETL can utilize an existing facility to produce additional liquid streams. The implementation of OCM-ETL can allow for the generation of on specification "pipeline gas." The products from the facility can be suitable for use (or on specification or "spec") as pipeline gas, gasoline product, hydrocarbon (HC) streams with high aromatic content, and mixed $C_4$ products. The PSA systems discussed above can be employed to separate, pre-separate or purify the hydrocarbon feed streams in the integrated NGL OCM-ETL system. FIG. 11 shows an example NGL extraction facility integrated with an OCM-ETL system. As shown in FIG. 11, for example, the feed to the PSA 1102 can be the net incoming gas from the treatment system 1101, which can treat a methane stream (e.g., natural gas) 1110. The PSA system can separate the feed to the OCM reactor 1103, which is mostly methane and lighter components with some ethane to utilize a PBC section of the OCM reactor, and the feed to the ETL reactor 1105, which can first be processed in a natural gas liquids extraction system 1104. The feed to the ETL system can be the PSA tail gas and OCM effluent comprising ethylene, propylene, ethane, propane, hydrogen, methane, and other components. In some cases, the OCM effluent can be directly fed to the ETL reactor. In some cases the OCM effluent is hydrogenated and fed to the ETL system. In some cases, as shown for example in FIG. 11, the OCM effluent is fed back to the PSA unit for separation; additional natural gas 1111 can be added, and a stream can be recovered 1112 (e.g., for use as pipeline gas). In some examples, the system may have a methanation unit that takes in the effluent from ETL reactor or OCM reactor and converts the CO, $CO_2$ and $H_2$ to methane, thereby further increasing the carbon efficiency of the process. The existing NGL extraction and product fractionation 1106 sub-systems can then be used to fractionate the final products, including into a mixed $C_4$ stream 1114 and a $C_{5+}$ product stream 1115.

Refinery gas typically contains valuable components like hydrogen, methane, ethane, ethylene, propane, propylene, and butane. Most commonly, refinery off-gases (ROG) are exported to the fuel gas system, thereby losing the value of the components contained therein. The OCM-ETL process can be used to improve the value of products as the OCM converts the methane to ethylene and the ETL converts olefins (e.g., those existing in the ROG and those generated by OCM) to higher value liquids as $C_4$ components, gasoline blends, or aromatic components.

Figure 12:
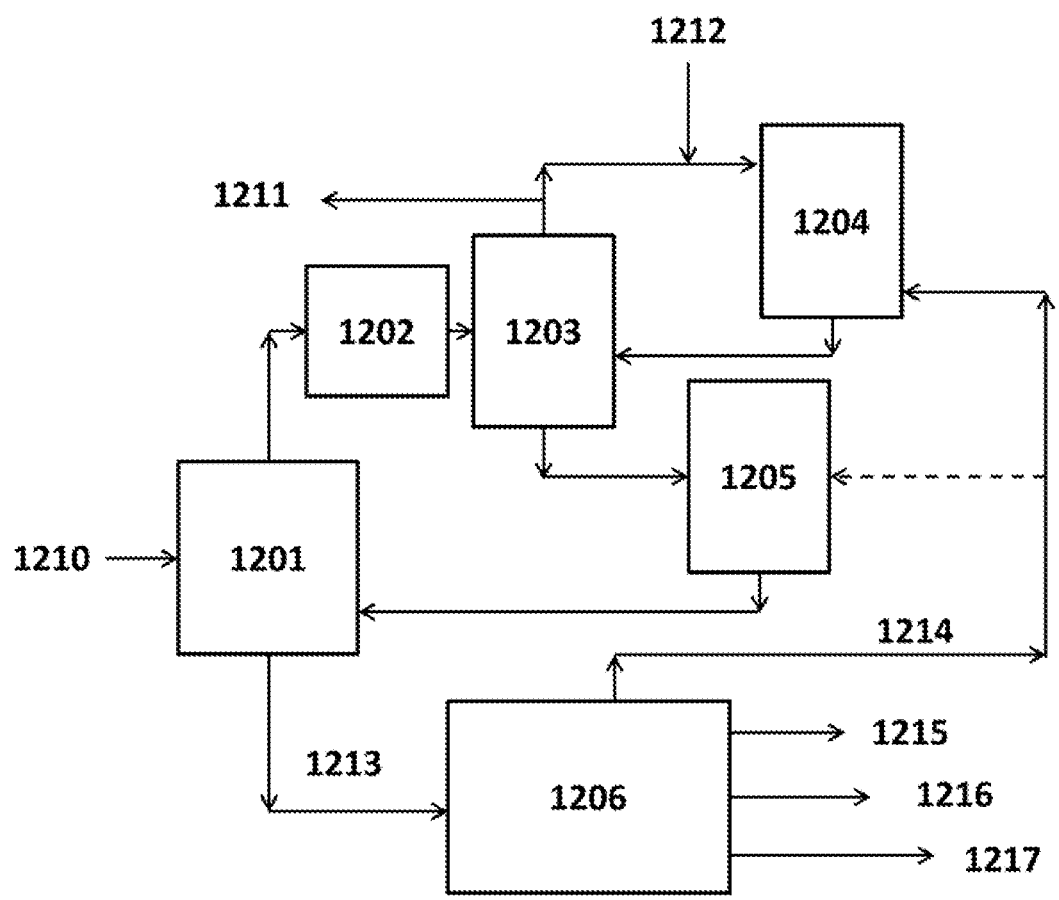
FIG. 12 shows an example system of the present disclosure using a PSA unit integrated with an OCM-ETL system for a refining application.

FIG. 12 shows an example PSA unit integrated to a refinery process scheme. A refinery gas plant 1201 can receive gas 1210 from cracking or other units. The PSA unit 1203 (after, for example, treatment of the gas in a treatment unit 1202) can separate components in refinery gas plant off gas to methane and a $C_{2+}$ cut which contains most or all of the olefinic materials. The methane can be used as refinery fuel 1211 and/or directed to an OCM unit 1204 with post-bed cracking. The OCM feed can be supplemented with additional natural gas 1212. The olefinic materials can be directed to an ETL reactor 1205. The OCM effluent can also be routed to the PSA where the olefins produced in the OCM are also sent to the ETL reactor. In some cases, the OCM effluent can be routed to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component from about 1% to 99%. A $C_{3+}$ stream 1213 from the refinery gas plant can be directed to a product fractionation system 1206, which can provide a $C_2/C_3$ stream 1214 (which can be directed to the OCM reactor), an $iC_4$ stream 1215, a gasoline blend stream 1216, and/or a kerosene/jet stream 1217.

As shown in FIG. 13, in some cases the system can have a methanation unit to further improve the carbon efficiency of the process. A refinery gas plant 1301 can receive gas 1310 from cracking or other units. The PSA unit 1303 (after, for example, treatment of the gas in a treatment unit 1302) can separate components in refinery gas plant off gas to methane and a $C_{2+}$ cut which contains most or all of the olefinic materials. The methane can be used as refinery fuel 1311 and/or directed to a methanation unit 1304, and then to an OCM reactor 1305 with post-bed cracking. The methanation feed can be supplemented with additional natural gas 1312. The olefinic materials can be directed to an ETL reactor 1306. The OCM effluent can be routed to the ETL reactor. In some cases, the OCM effluent can also be routed to the PSA where the olefins produced in the OCM are also sent to the ETL reactor. In some cases, the OCM effluent may be hydrogenated before being sent to the PSA unit or ETL reactor. Some techniques may dictate the use of a cryogenic demethanizer in place of the PSA, but the application of PSA to pre-separate the refinery off-gas into a product stream and a tail gas stream containing the heavier hydrocarbons which is the feed to ETL reactor can result in significant cost savings. The product stream can contain methane, ethane, CO, $CO_2$, and other components, with of each component being present at a concentration or relative amount from about 1 to 99%, for example. A $C_{3+}$ stream 1313 from the refinery gas plant can be directed to a product fractionation system 1307, which can provide a $C_2/C_3$ stream 1314 (which can be directed to the OCM reactor), an $iC_4$ stream 1315, a gasoline blend stream 1316, and/or a kerosene/jet stream 1317.

Adsorbent Based Systems for Hydrocarbon Separation with High Olefin Selectivity

An OCM process configuration that can reduce the overall capital costs can utilize non-cryogenic separations that do not require high process gas compressions and refrigeration. The cryogenic separation can operate at pressures in the order of 40-50 bar, whereas the PSA system described herein can be operated at much lower pressure range. A multi-stage adsorbent bed system can be used that is capable of removing the bulk of lighter components (e.g., methane, hydrogen, ethane, and carbon monoxide) in the first stage, and then removing the remaining of the lighter components in a subsequent stage. The materials used for the beds can be Calcium-X (CaX) zeolite (or CaLSX zeolite), or metal organic framework such as $M_2$(para or meta dobdc) (where dobdc is 2,5-dioxido-1,4-benzenedicarboxylate and M can be, without limitation Fe, Co, Ni, Mg, Mn), or a layered combination.

Since the ethylene is preferentially adsorbed on these materials, the choice of regeneration and/or purge gas can contribute to the final recovery and design of the overall process scheme in the system. Described herein are three example process schemes with different purge gases for regeneration of each bed. The process can be configured with different combinations of purge gas for different beds as well as operating one or more of the beds under vacuum for regeneration.

As used herein, the "product component" is the component in the gas stream that is considered to be the desired product, and is typically aimed to be recovered in as much high purity as possible. For example, in case of OCM process, ethylene can be the product component.

Usually PSAs are designed to handle streams that have few components in the feed (e.g. 2, 3, 4, or 5 components at greater than 3% concentration). In contrast, the systems and methods described herein can be capable of removing bulk of undesired components from a stream of multitude of components, like methane, hydrogen, ethane, carbon monoxide, and carbon dioxide, among others. The product stream can still be highly enriched in the product component (ethylene in this case) despite the large number of components.

Described herein is a method for separating a product from a gas mixture. The method may comprise, at a first total pressure, directing a gas mixture into a pressure swing adsorption (PSA) vessel. The gas mixture may comprise a product and at least one impurity (e.g., at least about 2, 3, 4, 5, 6, 7, 8, 9, 10, 11, 12, 13, 14, 15, 16, 17, 18, 19, 20 or more impurities). The product may have a concentration of less than or equal to about 50, 45, 40, 35, 30, 25, 20, 18, 16, 14, 12, 10, 8, 6, 4, 2, 1 mol %, or less in the gas mixture. The at least one impurity may comprise carbon monoxide (CO), carbon dioxide ($CO_2$), methane ($CH_4$), ethane ($C_2H_6$), hydrogen ($H_2$), or any combinations thereof. The gas mixture may comprise an effluent(s) from one or more processing units including for example, an OCM unit, an ETL unit, a cracking unit, a separations unit, a methanation unit, or combinations thereof. The PSA vessel may comprise an adsorbent. The adsorbent may comprise a metal organic framework (MOF) such as $M_2$(dobdc). The adsorbent may be configured to adsorb the product thereon. In some cases, the product has a first partial pressure.

Next, a sweep gas may be directed into the PSA vessel at a second total pressure. The sweep gas may be adsorbed on the adsorbent thereby displacing the product from the adsorbent to yield a displaced product. The sweep gas may have a second partial pressure. The second partial pressure may be greater than, less than or equal to the first partial pressure of the product in the gas mixture. Subsequently, the sweep has may be desorbed from the adsorbent at substantially (e.g., at least about 80%, 82%, 84%, 86%, 88%, 90%, 91%, 92%, 93%, 94%, 95%, 96%, 97%, 98%, 99%, or more) the first total pressure, such that additional product may be capable of adsorbing on the adsorbent. After the adsorption of the product from the gas mixture, the gas mixture may comprise a predetermined amount of a given impurity (e.g., $CO_2$). In some cases, an amount of the product that adsorbs on the adsorbent at the first partial pressure may be substantially equivalent to the amount of the sweep gas that adsorbs on the adsorbent at the second partial pressure.

Heat may be released upon adsorption of the product and/or the sweep gas on the adsorbent. An amount of heat released by the adsorption of the product may be the same as or different from an amount of heat released by the adsorption of the sweep gas. In some cases, the amount of heat released by the adsorption of the product is greater than or equal to about 50%, 60%, 70%, 80%, 85%, 90%, 91%, 92%, 93%, 94%, 95%, 96%, 97%, 98%, 99%, or more of the amount of heat released by the adsorption of the sweep gas. In some cases, the amount of heat released by the adsorption of the product is less than or equal to about 100%, 98%, 96%, 94%, 92%, 90%, 85%, 80%, 75%, 70%, 65%, 60%, 55%, 50%, or less of the amount of heat released by the adsorption of the sweep gas. In some cases, the amount of heat released by the adsorption of the product is substantially equivalent to (e.g., greater than or equal to about 90%, 95%, 99%, or more of) the amount of heat released by the adsorption of the sweep gas.

The displaced product may be enriched (e.g., concentration increased) relative to the product in the gas mixture by a factor of at least about 1.5, 2, 2.5, 3, 3.5, 4, 4.5, 5, 5.5, 6, 6.5, 7, 7.5, 8, 8.5, 9, 9.5, 10, 12, 14, 16, 18, 20, 25, 30, 35, 40, 45, 50, or more. In some cases, the displaced product may include some of the sweep gas, for example, at least about 0.001, 0.005, 0.01, 0.05, 0.1, 0.2, 0.3, 0.4, 0.5, 0.6, 0.7, 0.8, 0.9, 1, 2, 3, 4, 5, 6, 7, 8, 9, 10, 12, 14, 16, 18, 20 mol %, or more of the sweep gas. The product and/or the sweep gas may comprise olefins (e.g., ethylene, propylene, and butadiene), paraffins (e.g., methane, ethane, propane), and/or other types of hydrocarbon or nonhydrocarbons compounds (e.g., $CO_2$, $CO$, $O_2$, $N_2$, $H_2$). In some examples, the product is ethylene. In some examples, the sweep gas is ethane.

In some cases, at the first pressure, a selectivity of the adsorbent for adsorbing the product as compared to the at least one impurity is at least about 2, 5, 10, 12, 14, 16, 18, 20, 25, 30, 35, 40, 45, 50, 55, 60, 65, 70, 75, 80, 85, 90, 95, 100, 120, 140, 160, 180, 200 or more. As used herein, selectivity of component 1 over component 2 (e.g., the product over the at least one impurity), for an adsorbent at a specified total pressure, temperature, and gas phase composition, is defined as $(x1*y2)/(x2*y1)$, where $x1$=mole fraction of component 1 in adsorbed phase, $y1$=mole fraction of component 1 in gas phase, $x2$=mole fraction of component 2 in adsorbed phase, $y2$=mole fraction of component 2 in gas phase. The gas mixture may be derived from an effluent from an OCM reactor. The at least one impurity may be recycled to the OCM reactor following the adsorption of the product from the gas mixture.

The PSA system described herein can recover the product component even when it is present in very low concentrations in the feed stream (e.g., less than or equal to about 10%, 9%, 8%, 7%, 6%, 5%, 4%, 3%, 2%, 1%, 0.5%, 0.1%, or less). An example of such a case is an effluent of an OCM process. The bulk of OCM effluent may include methane and hydrogen. The product component (ethylene) can be in a very low concentration exiting the reactor. In an adsorbent based separation systems, a component with high partial pressure (i.e., having high concentration) may tend to adsorb more on the adsorbent, whereas a component with low partial pressure may tend to adsorb less strongly and/or in lesser amounts. In some cases, lighter components (e.g., methane and hydrogen in the case of OCM) tend to adsorb less, whereas heavier components tend to adsorb more (e.g., ethylene in the case of OCM). These competing tendencies of adsorption with respect to partial pressure and molecular weight can make it difficult to get a clear difference in adsorption capacities for the undesired and desired components. The systems and methods described herein resolve this conflict by using materials that preferentially adsorb the desired product (e.g., ethylene for OCM, which is the heavier component, but has a low partial pressure). Thus, the materials used herein can have the property of showing a strong adsorption preference for the product component over undesired components despite low partial pressure of the product component.

In PSA based separation systems, the product component may be the one that is not adsorbed and is recovered at a high purity in the light stream. The adsorbed undesired component may then be removed from the bed by desorbing it at a lower pressure (or even vacuum) using a portion of the light product as the sweep gas. In some cases, however, the desired product (e.g., ethylene in the case of OCM), may be the heavier component that gets adsorbed on the adsorbent. To desorb it and recover it as a product, the light product may not be used as a sweep gas, since this is the component that the product needs to be separated from in the first place.

In the systems and methods described herein, the sweep gas can be chosen on the basis of criteria including e.g., (a) it is separable from the product component (e.g., ethylene in the case of OCM) following the adsorptive separation; (b) it not just sweeps the desorbed product (e.g., as a convection effect), but also replaces it on the bed as a mass transfer effect, in order to enhance the rate of desorption; and/or (c) it is not detrimental to the reactor when a portion of it is carried over with the lighter stream during the adsorption step (which can be recycled back to the reactor). In some cases, the sweep gas achieves any two of (a)-(c). In some cases, the sweep gas achieves all of (a)-(c).

The desorption step in a PSA may be done at a lower pressure than the adsorption step. In some cases, the systems and methods of the present disclosure may be configured to perform the desorption step with a suitable sweep gas at a higher pressure than absorption. In some embodiments, the sweep gas shows a greater tendency to become adsorbed on adsorbent, and thus replace the product component (ethylene in case of OCM). This can be done to counter the adsorbent material's strong adsorption preference for the product component, and ensure recovery of the product component. The choice of the sweep gas is made such that it shows significantly higher tendency to replace the product component at a high pressure (in comparison to the partial pressure of the product component in the feed stream) during the desorption step, whereas the sweep gas itself can be easily desorbed from the bed by lowering the pressure to make way for the product component to take its place during the adsorption step in the next cycle. Thus, the adsorption isotherm of such a sweep gas can be very different from that of the product component such that product component shows high adsorption capacity even at very low partial pressure, whereas the proposed sweep gas shows high adsorption capacity only at high pressure.

PSA based separation systems can be designed to maximize recovery and purity of the product components. Even if one of these is compromised, it can be done as a trade-off to maximize the other objective. However, the intent remains to separate the components as much as possible. In the systems and methods described herein, however, a methodology is devised to get a specific split of a component ($CO_2$ in the present example). This component is not necessarily being the product component. The split can be such that a specific desired proportion goes into the lighter stream, while the rest goes into the heavier stream. Such a split may be a requirement of the overall process scheme (for example, in the OCM process, a specific portion of $CO_2$ is sent with the lighter stream to the methanation reactor, while the rest is separated out and purged). This can be done while still maximizing the capture of the product component (ethylene in the case of OCM). Therefore, the systems and methods described herein may use a combination of more than one type of materials in the adsorbent bed in such a way that one material is a weak adsorber of the component to be split, but a strong adsorber of the product component (e.g., $Co_2$(m-dobdc)), while another material may be a strong adsorber of both the component to be split and the product component (e.g., CaX). By using a proportionate layered combination of the two materials in the same bed or in separate beds, the product component can be fully captured, while the component to be split can be split in the desired proportion.

Figure 14:
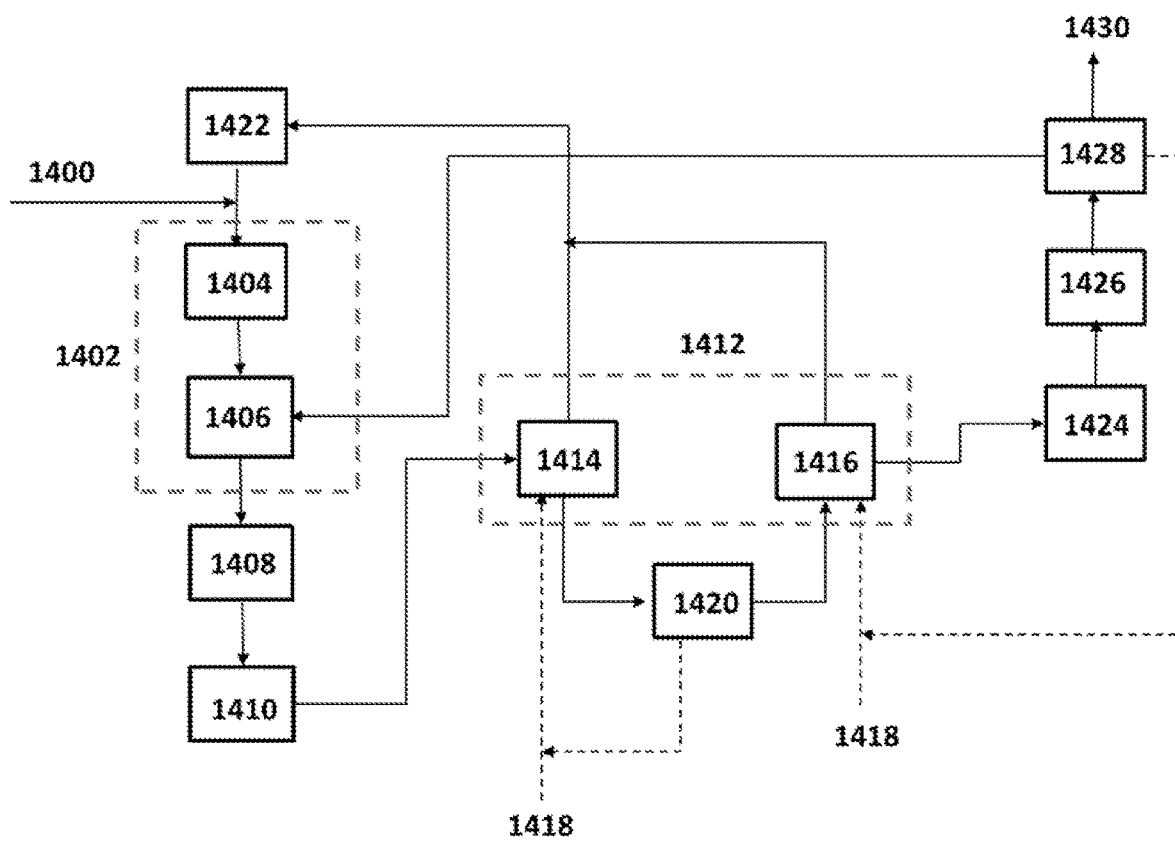
FIG. 14 shows an example system of the present disclosure using a separation system for OCM using propane as a purge gas.

Several examples of process configurations using adsorption purification to recover ethylene from OCM effluent are provided herein. FIG. 14 shows a process configuration with propane (or propane diluted with a light gas) used for purge gas in the PSA systems. Natural gas and oxygen 1400 are fed to the OCM reactor 1402 comprising a catalytic region 1404 containing an OCM catalyst and a post-bed cracking region 1406. The effluent from the reactor contains majority of unreacted methane, followed by hydrogen, ethylene, $CO_2$, ethane, CO, propylene and other minor components. The exotherm from the OCM reactor can be recovered using a HRSG (heat recovery steam generation) 1408 to recover the heat potential for steam generation for use within the process or for export. The heat can also be utilized for any internal stream heat exchange. The effluent can then be dried (e.g., in molecular sieves) 1410. The ethylene recovery can be based on adsorption separation rather than cryogenic separation. The effluent from drying can be sent to a bulk separation first stage 1414 of the PSA system 1412. The bed can be capable of strong adsorption for ethylene and $CO_2$ when compared to lighter components. Lighter components such as methane, hydrogen, ethane, and CO can breakthrough the bed during the adsorption step in some cases. Hence, the bed can be capable of separating majority of methane, hydrogen, ethane and CO from the bed. A portion of methane can still be adsorbed in the bed due to the high incoming concentration, resulting in high partial pressure, and thus some adsorption of the methane.

The regeneration of the bed can be performed using propane 1418, or propane diluted with a light gas that is weakly adsorbed on the bed. This step can be performed at a different pressure than adsorption to get a pressure swing effect and/or at a different temperature to get temperature swing effect. Propane being strongly adsorbed on the bed, is capable of replacing ethylene and $CO_2$ from the adsorption sites, therefore desorbing the ethylene and $CO_2$, including carryover of traces of light components. The effluent from the regeneration step can be the product of the first stage. Since the regeneration gas (propane) replaces ethylene during the desorption step, there can be a carryover of this propane with the lights stream during the adsorption step.

At this stage, propane can be separated 1420 (for example, using distillation) and resent into the purge gas system. This can result in a cleaner $C_2$ stream that can be recovered more efficiently in a second bed.

The stream now containing ethylene, $CO_2$, and a small portion of other components is sent into a second bed 1416 containing a layered combination of two materials such that one has strong adsorption for $CO_2$ (e.g., CaX), while the other has weak affinity for $CO_2$ (e.g., $M_2$(dobdc)). Such a combination can aid in a desired split of $CO_2$ in the adsorbed and non-adsorbed phases for further optimized processing of $CO_2$, while achieving high ethylene recovery. Methane, ethane and a portion of $CO_2$ can be released as lights during the adsorption step. This stream along with the stream from the adsorption step of the first bed can be combined to remove propane and then sent into the methanation unit 1422 for further conversion of CO and $CO_2$ into methane. This step improves the overall carbon efficiency of the unit.

The second bed (i.e., CaX+$M_2$(dobdc)) can be desorbed again using propane for efficient removal of the adsorbates. The desorbed gas now comprises the ethylene, the purge gas propane and minor amounts of ethane.

A $CO_2$ removal unit 1424 (which can be much smaller than the designs not having the absorption systems described herein) can remove $CO_2$ for venting. An acetylene hydrogenation 1426 step can be used for conversion of acetylene into ethylene.

A final purification column 1428 for ethylene can then separate the product ethylene 1430 from propane and ethane and other minor components, thus producing polymer grade ethylene as product. A propylene separation can be performed either as a small distillation column or in a combined ethylene/propylene separation unit in a membrane system that is capable of removing olefins over paraffins.

Figure 15:
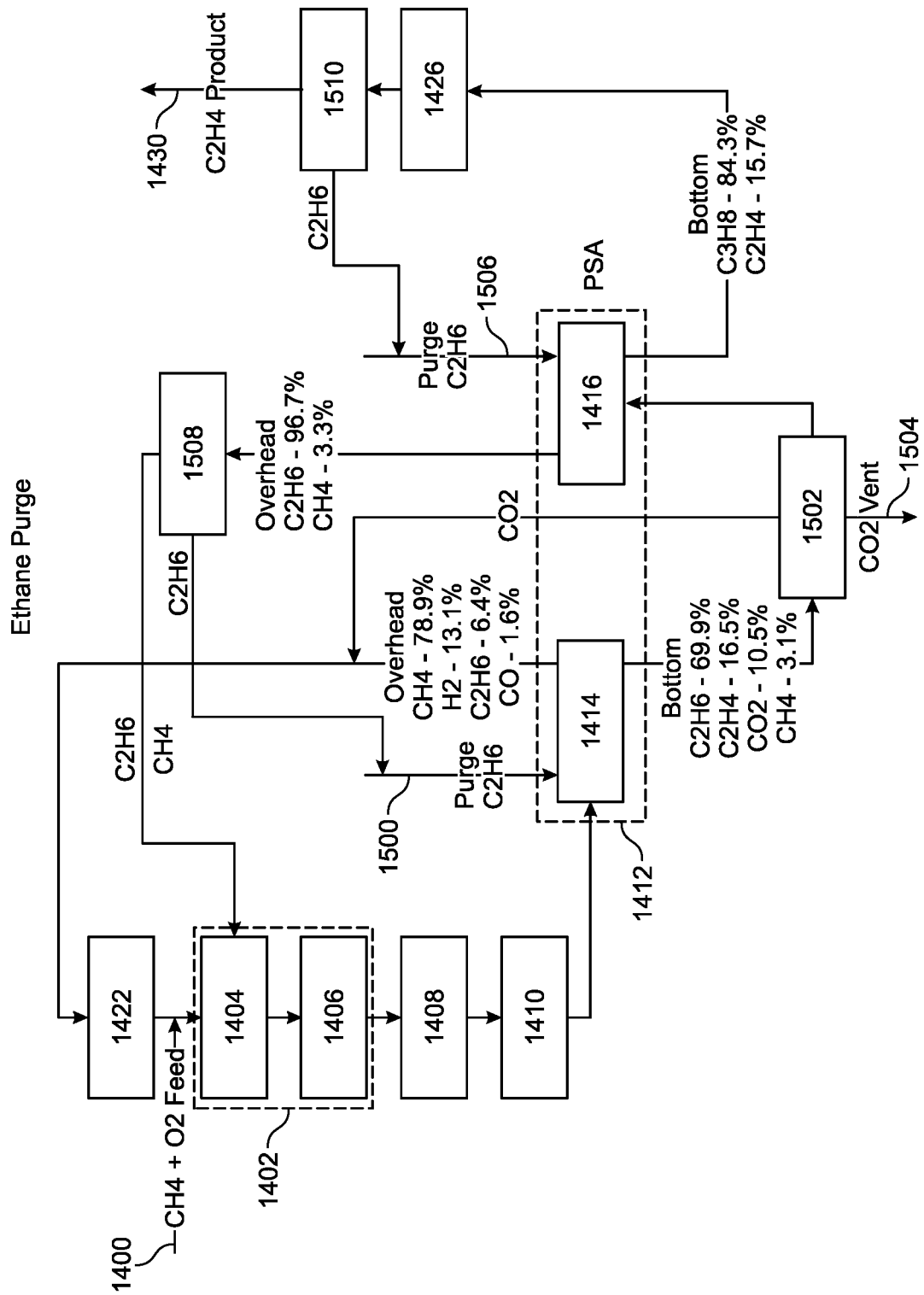
FIG. 15 shows an example system of the present disclosure using a separation system for OCM using ethane as a purge gas.

FIG. 15 shows a process scheme using ethane as a purge gas, where like numbered elements correspond to elements in FIG. 14. Described herein are examples of specific separations from each of the PSA beds and the recoveries obtained for the primary components of separation using the ethane as the purge gas for both of the beds. The effluent from drying is first sent into a CaX bed PSA system 1414. CaX has shown strong adsorption for ethylene and $CO_2$ when compared to ethane and other lighter components. Lighter components such as methane and hydrogen can breakthrough the bed during the adsorption step. Thus majority of methane and hydrogen can be removed in this step, and the unadsorbed stream may contain as much as about 79% methane and 13% hydrogen. A portion of methane is still adsorbed in the bed due to the high incoming concentration, thus resulting in high partial pressure and adsorption of the methane. This stream is directly sent into the methanation section 1422 before the OCM reaction.

The regeneration of the bed can be performed using ethane 1500. Ethane at approximately the same pressure as adsorption or higher pressure can bind in the CaX sites and release the ethylene and $CO_2$. This desorption gas can contain about 70% ethane (purge gas+adsorbed ethane), about 17% ethylene and about 10% $CO_2$, which can be sent into a $CO_2$ removal unit 1502.

At this stage, $CO_2$ can be removed and separated into two streams, one going back into methanation reactor along with the methane rich stream containing hydrogen, and the rest being vented 1504. In the methanation reactor, hydrogen from the system may be utilized to convert CO and $CO_2$ back into methane thus improving the overall carbon efficiency.

The stream now containing ethylene, ethane and a small portion of methane can be sent into a second PSA bed 1416 containing adsorbent (e.g., $M_2$(dobdc)). The adsorption step can remove all of the methane from the ethylene product stream, with the unadsorbed gas containing ethane (about 97%) and the methane carried over from CaX bed (about 3%). The desorption can be performed at adsorption pressure or slightly higher pressure with ethane 1506, where ethane replaces the ethylene bound in the second adsorbent bed (e.g., containing $M_2$(dobdc)). In some cases, the desorption gas can contain only two components: ethylene (about 16%) and ethane (about 84%). The high percentage of ethane in the desorption gas can be due to it being used as purge gas. However, this stream can be much easier to process and purify ethylene since all the other effluent components were thoroughly removed by the two PSA units. The purge gases can be resolved in a purge gas recovery module 1508. A $C_2$ splitter 1510 can perform the final purification of ethylene and produce polymer grade ethylene product. An advantage can be realized compared to cryogenic separations in utilizing smaller process units for final purification instead of huge compressions systems, refrigeration systems, $CO_2$ removal and distillation columns that process entire effluent streams.

Figure 16A:
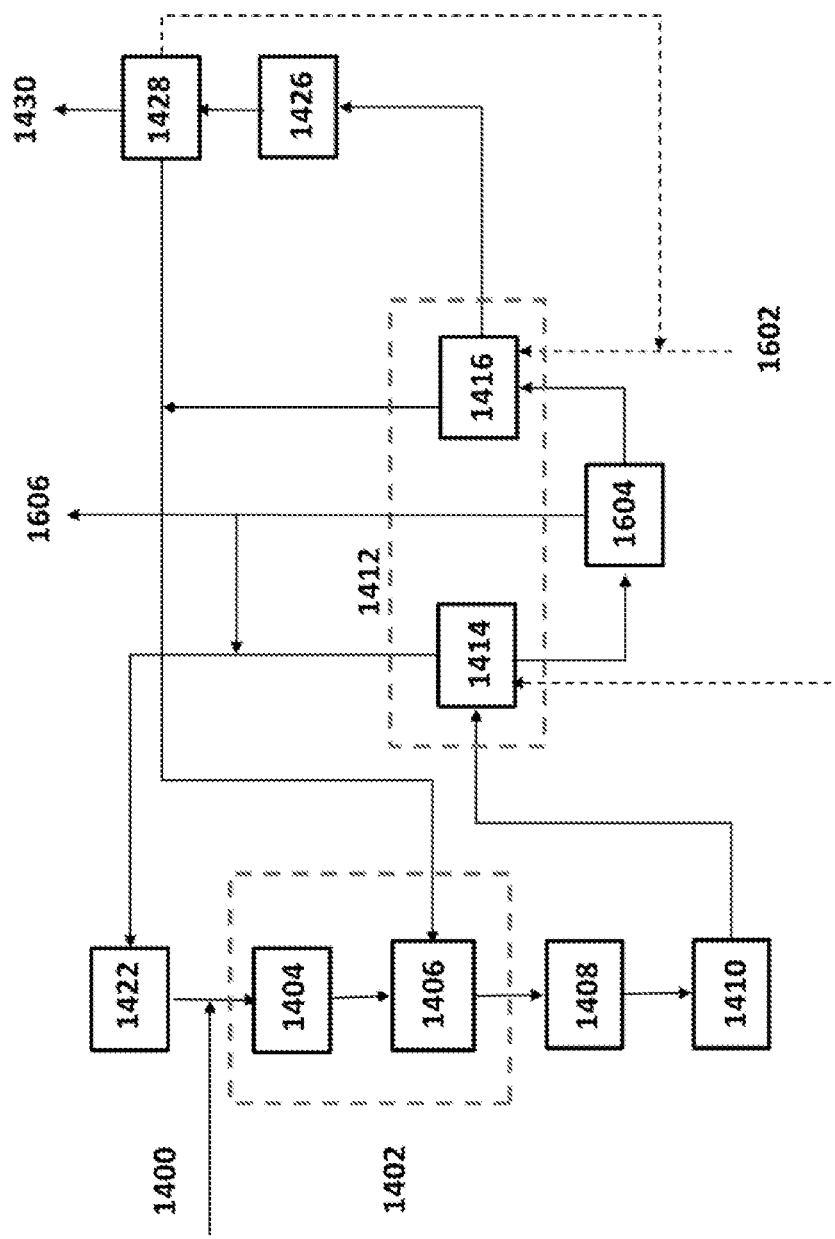
FIG. 16A and FIG. 16B show example systems of the present disclosure using a separation system for OCM using propane and ethane as a purge gas.
Figure 16B:
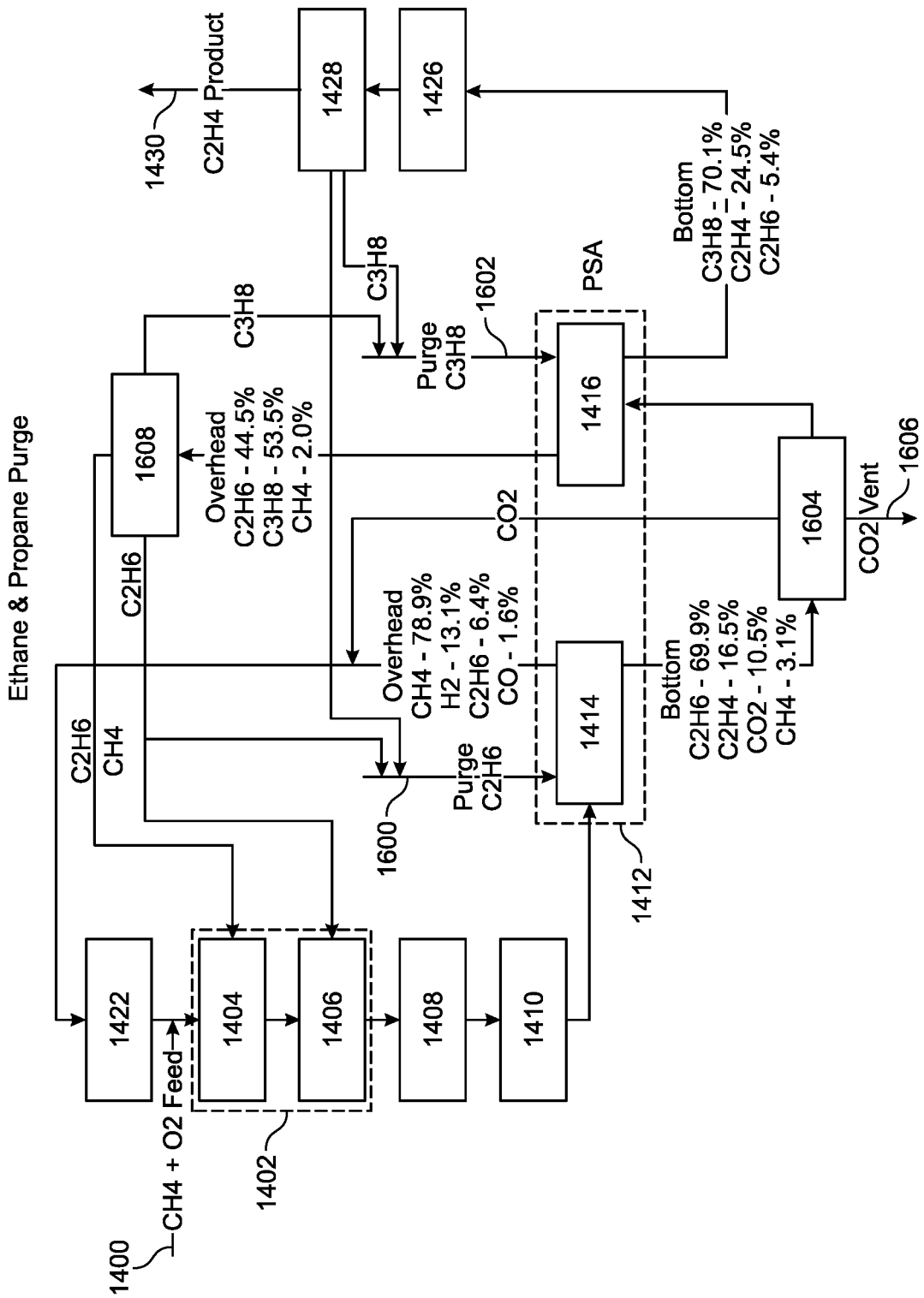

FIG. 16A and FIG. 16B show an example process with ethane and propane being used for purge gas in the PSA systems, where like numbered elements correspond to elements in FIG. 14. Compared with FIG. 16A, FIG. 16B shows additional detail regarding stream compositions and the purge gas recovery system 1608. The desorption of the first bed 1414 in this case can be performed utilizing ethane 1600 as purge gas. This removes a propane separation step between the two stages in comparison with FIG. 14. The desorbed gas which now contains mainly ethane (since it is the purge gas), ethylene, $CO_2$ and methane can be sent into a $CO_2$ removal unit 1604. This unit can be smaller than the $CO_2$ removal unit in designs using cryogenic separations due to a smaller volume of gas it processes (effluent stream minus majority of methane and hydrogen). The $CO_2$ that is removed can be split into two portions. A portion of the $CO_2$ can be sent into the methanation 1422 unit along with the light gas from the adsorption step of the first bed, which primarily contains methane, hydrogen, CO, and ethane. The methanation unit converts CO and $CO_2$ into valuable methane using hydrogen, thus improving the overall carbon efficiency of the system. The rest of the $CO_2$ from the desorption step of the CaX bed can be vented to the atmosphere 1606.

The effluent from the desorption step of the first bed can be sent into a second bed 1416. The stream from the adsorption step can then be directly sent into the post bed cracking section 1406 of the reactor, for the conversion of ethane into ethylene, thus increasing the overall ethylene production rate. Alternatively, a similar scheme such as in FIG. 14 with two adsorbent layers with different $CO_2$ adsorptivity can be used for the effluent from the first bed. In such a design, the $CO_2$ removal can be performed after the desorption from the second bed, since the second bed then removes a desired portion of $CO_2$ for conversion into methane using methanation.

The second bed can be desorbed using propane 1602, for efficient removal of ethylene. The desorbed gas now contains mainly ethylene and propane, with minor quantity of ethane. This stream can then be sent to an acetylene hydrogenation unit 1426 for conversion of ethylene into ethane and finally into an ethylene purification column. The final column 1428 now containing much smaller volumes of gases can be cryogenically separated (or separated in an olefin selective membrane) for high purity ethylene 1430.

Figure 17:
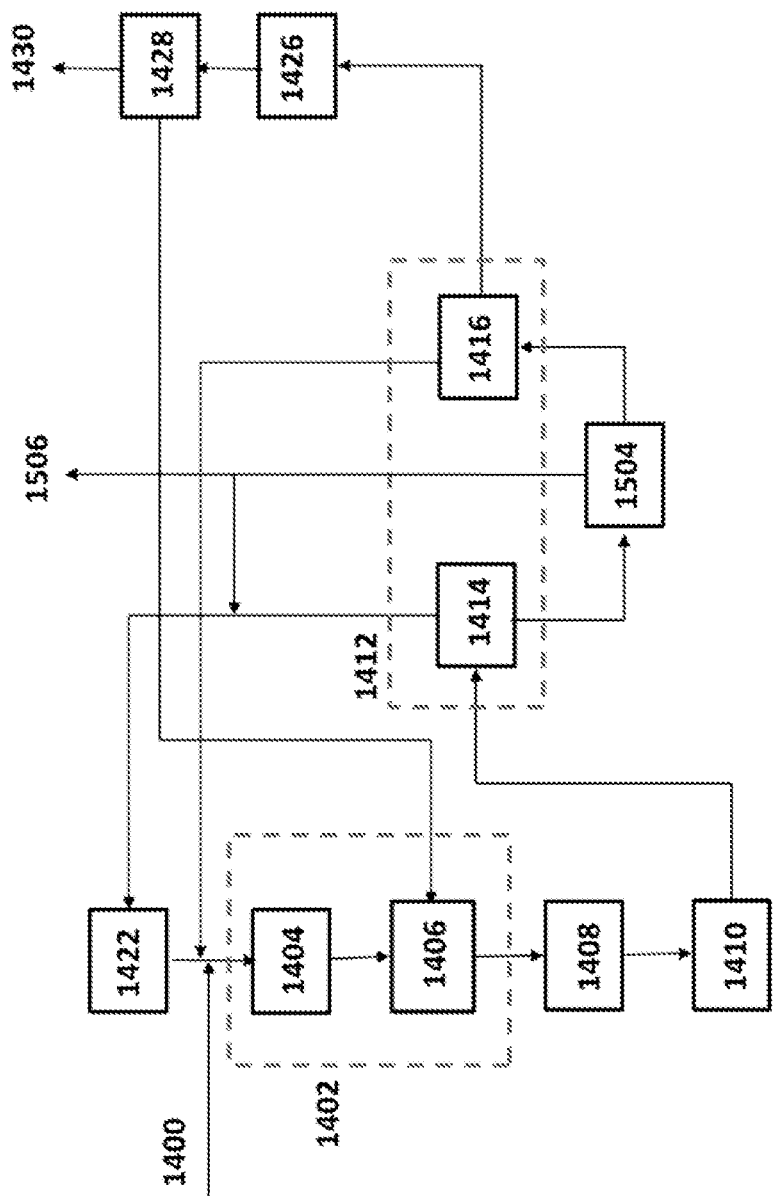
FIG. 17 shows an example system of the present disclosure using a separation system for OCM using a vacuum PSA.

FIG. 17 shows a process scheme using vacuum pressure swing adsorption for high purity separation, where like numbered elements correspond to elements in FIG. 14 and/or FIG. 16A. Vacuum can be used for the desorption step of the PSA beds. Although utilizing vacuum systems can potentially increase the capital and operating costs of the unit, they have the advantage of avoiding, or minimizing additional purge gas streams into the systems and resulting in higher purity product in some cases. In the above scheme, the adsorption step of the first bed releases methane, hydrogen, ethane, and CO. The desorption step under vacuum releases the adsorbed components such as ethylene, $CO_2$, and a small portion of methane and ethane.

The desorbed stream can then be sent into a $CO_2$ removal unit. A portion of the $CO_2$ can be mixed along with the lights stream from adsorption step and sent into the methanation unit for further conversion into methane. The desorbed product can be sent into the second step of bed.

The second stage bed adsorbs ethylene from the stream. Ethane and methane can be released during the adsorption step, which can be recycled back into the OCM reactor. The MOF bed can be desorbed under vacuum for recovering high purity ethylene. This stream containing ethylene and minor portions of ethane and acetylene is then sent into an acetylene hydrogenation system for conversion of acetylene into ethylene. A final ethylene purification column can then separate ethylene as polymer grade from ethane.

A combination of different purge gases (including but not limited to ethane, propane, butane, $CO_2$, hydrogen, etc.) and vacuum swing can also be utilized for each of the two beds, along with a combination of different layers of adsorbent materials in each bed in order to achieve different ethylene purity grades, recovery and overall carbon efficiency with the recycle.

Figure 18:
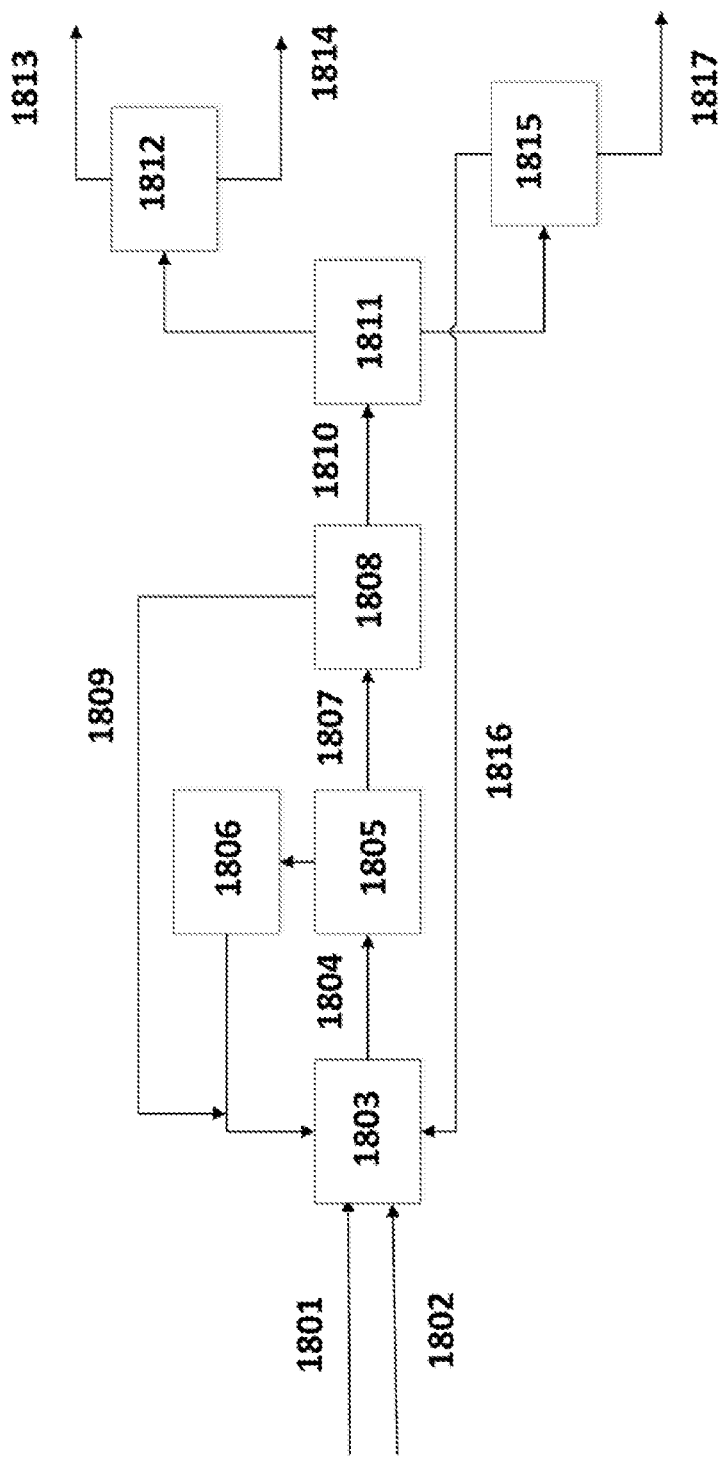
FIG. 18 shows an example system of the present disclosure using an OCM process scheme employing metal-organic framework (MOF) separations.

For an OCM process, MOFs can be utilized for separation of various light hydrocarbons. In FIG. 18, for example, oxygen 1801 and methane 1802 feed the OCM reactor 1803. The process effluent 1804 comprising mainly hydrogen, CO, $CO_2$, $CH_4$, $C_2H_4$, $C_2H_6$ and $C_{3+}$ hydrocarbons is first sent to a pretreatment unit 1805. Any potential contaminants to the downstream recovery systems (e.g., contaminants to membranes, adsorbent beds containing zeolites, polymers or MOF membranes or adsorbents) can be removed in this unit. This unit can include a $CO_2$ removal system, acetylene removal bed for diene sensitive beds, sulfur removal bed, or molecular sieve dryer. Hydrogen can also be recovered from this stream, for example by utilizing an MOF bed selective to hydrogen over other light hydrocarbons such as methane. Hydrogen removal can be important for separation systems using adsorbents/membranes that are sensitive to hydrogen in the operations that follow. The hydrogen, $CO_2$ and CO streams can be sent to the methanation unit 1806 for further conversion to methane. The outlet 1807 from the pretreatment unit can then be sent to a $C_1/C_{2+}$ bulk separation unit 1808 capable of separating methane from $C_2$ and higher hydrocarbons. In some cases, $C_1/C_2$ separation and olefin/paraffin separation can be performed in a single unit and/or using a single adsorbent (e.g., MOF). This separation unit can be a PSA, membranes made of zeolites such as CaX, NaX zeolite, microporous titanosilicates such as ETS-4, ETS-10, or selective MOF adsorbents/membrane systems that can perform the same function (for example, MOFs such as SBMOF-1, SBMOF-2, Zn-SIFSIX-Pyrazine, PCN-250, Cu-TDPAT, ZIF-67, ZJU-61, USTA-33, and USTA-10 can be used). These materials can be used for separating the light components including $N_2$ and $H_2$ along with methane and hence may not require any pre-treatment beds prior to a $C1/C_{2+}$ bulk separation unit. A methane gas stream 1809 separated can be recycled back to the OCM reactor. Alternatively, the outlet from the $C_1/C_2$ separation containing methane can be recycled back to the methanation unit 1806, for example if the stream contains portions of CO, $CO_2$ or $H_2$. The $C_{2+}$ stream 1810 can then be sent into an olefin/paraffin separation unit 1811, for example made of MOFs, zeolites, or polymeric membranes in a PSA or membrane unit. MOFs that can be useful for this operation include HKUST-1, $CO_2$ (dhtp), $Mg_2$ (dhtp), M (dobdc) (M can be Mg, Mn, Fe, Co, Ni, Zn), ZIF-7, ZIF-8, ZIF-4, and other Ag ion based MOFs such as Ag-MIL-101, Silver-Organic Frameworks Constructed with 1,1'-Biphenyl-2,2',6,6'-tetracarboxylic Acid or Silver m-phosphonobenzoate $Ag_6(m-O_3PC_6H_4CO_2)_2$, Ag(I) coordination polymer with 2,5-dimethylpyrazine ligand. Polymeric adsorbents capable of silver complexation such as Ag+ exchanged Amberlyst resin can also be used for such applications. The olefins stream can then be sent into a separator 1812 such as a flash unit operation or distillation column or any other separation system (e.g., PSA/TSA/membranes) that can separate pure ethylene 1813 from the $C_{3+}$ olefins 1814. A combination of the separation techniques can also be used to recover polymer grade ethylene. The paraffin stream can also be sent into a separator 1815 such as flash operation, distillation section, PSA, TSA unit, or membrane system to separate ethane from $C_{3+}$ paraffins. Ethane can be recycled 1816 back to the OCM reactor. Alternatively, the entire paraffin stream 1817 can also be recycled back into the OCM reactor to take advantage of the post bed cracking section of the reactor to convert into further ethylene. Separation of paraffins can also be performed using MOF adsorbent beds of RPM3-Zn.

Figure 19:
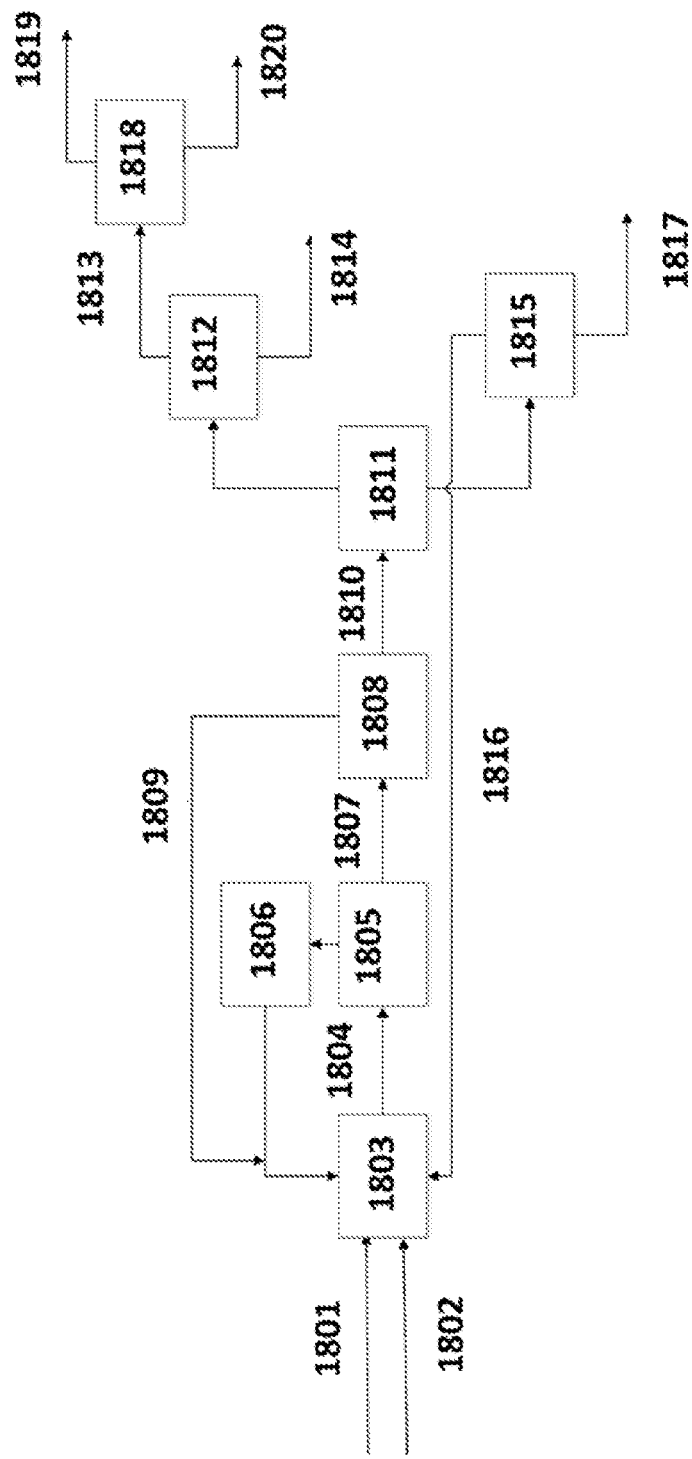
FIG. 19 shows an example of an OCM process scheme employing MOF separations.

In FIG. 19, a similar process scheme as FIG. 18 is proposed, except for the acetylene removal unit 1818 location, separating acetylene 1819 from ethylene 1820. Here the acetylene removal unit is downstream of the ethylene/propylene+ separation unit. This scheme can be utilized when acetylene is not a contaminant/poison to the olefin/paraffin separation beds or any of the separation systems prior to olefin separation unit (MOF/PSA/membrane systems). This scheme can be utilized if olefin/paraffin separation system is based on non-$Ag^+$ adsorbent beds/membranes such as Fe-MOF-74. In such a system, acetylene removal can be performed on the final product stream using MOF adsorbent beds/membranes selective to acetylene removal, for example, USTA-67a.

Figure 20:
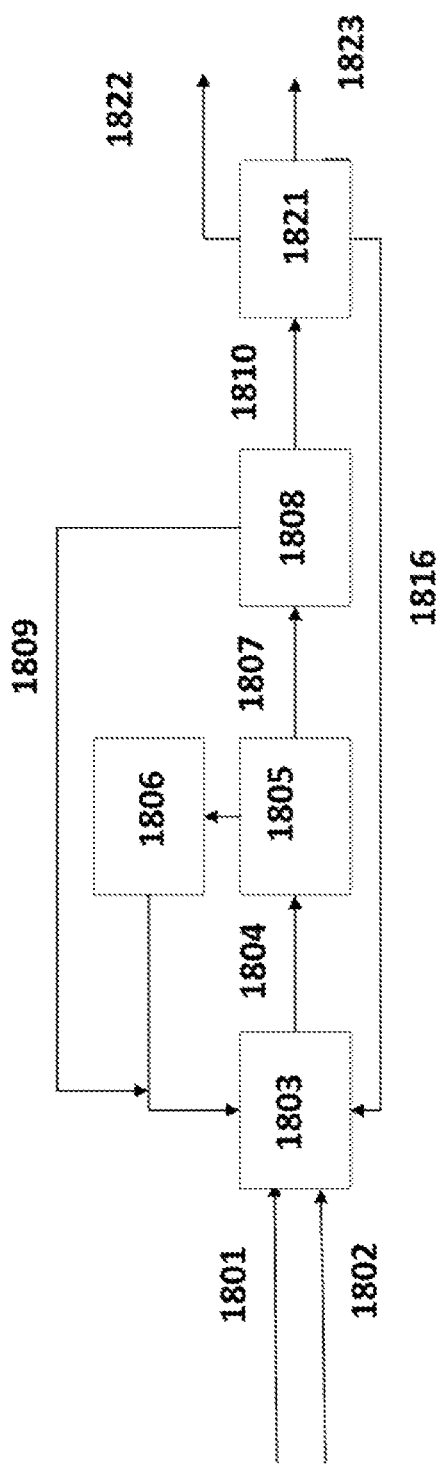
FIG. 20 shows an example of an OCM process scheme employing MOF separations.

In FIG. 20, the OCM effluent, after pre-treatment and hydrogen recovery (where necessary), is sent to adsorbent beds in a PSA system or to a membrane system containing MOFs such as $M_2$(dobdc) (meta or para form, M can be Mg, Mn, Fe, Co, Ni) 1808, 1821 that can be by themselves capable of separating all the lighter hydrocarbons into individual components ($CH_4$, $C_2H_4$, $C_2H_6$, $C_2H_2$). In such a system, the effluent from pre-treatment section can be first sent into an initial methane removal unit (PSA with multiple beds for simultaneous adsorption/desorption to run the process continuously). The desorbed mixture of $C_{2+}$ streams can then be separated into ethylene 1822, ethane 1816 and acetylene 1823 based at least in part on their different elution rates from the adsorbent bed (permeation times if membranes were to be used). Multiple beds operating simultaneously for this unit can help with continuous separation of the $C_2$ streams. Such a scheme can use a $C_{3+}$ removal system (PSA/membrane based on MOFs) for removing the $C_{3+}$ components prior to the methane removal unit.

Figure 21:
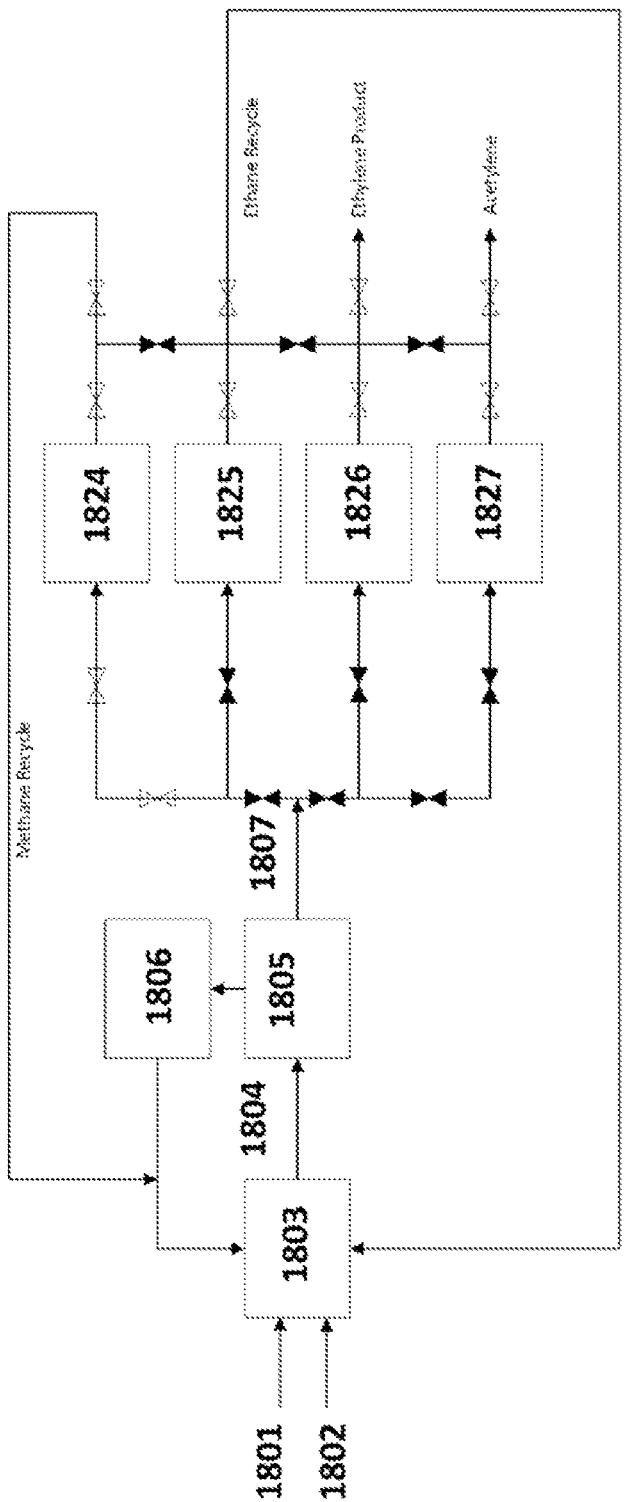
FIG. 21 shows an example of an OCM process scheme employing MOF separations.

FIG. 21 represents a similar system utilizing MOFs such as $M_2$(dobdc) (meta or para form, M can be Mg, Mn, Fe, Co, Ni) capable of separating individual light hydrocarbons, but each running in a different mode. A system utilizing 4 different adsorption systems (e.g., PSA) 1824, 1825, 1826, and 1827, with each bed operating in different mode is represented. Each bed is either in $CH_4$ removal mode 1824, $C_2H_2$ removal mode 1827, $C_2H_4$ recovery mode 1826 or $C_2H_6$ removal mode 1825. Using different valve-sequencing for the process gas (feed and outlet) between beds, the feed gas can be directed appropriately and effectively separated continuously into individual components thus recovering ethylene without lag times that may be generated in the adsorbent beds.

Figure 22:
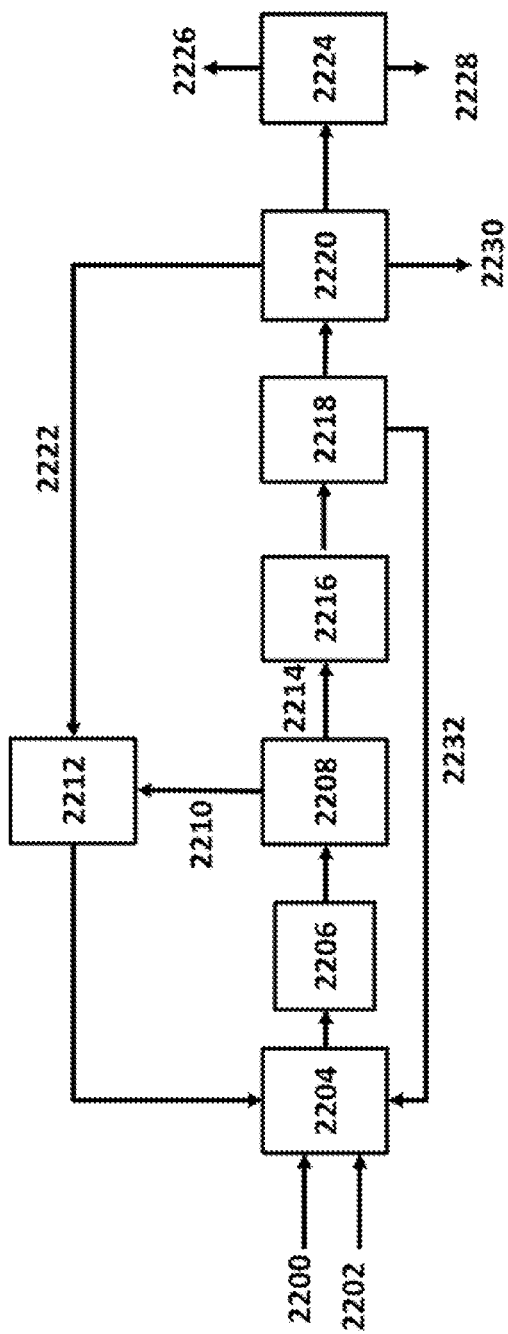
FIG. 22 shows an example of an OCM process scheme employing MOF separations.

FIG. 22 shows another example of an OCM system. In this case, oxygen 2200 and methane 2202 can be fed into an OCM reactor 2204 to produce an OCM effluent. The OCM effluent can be sent through a pre-treatment unit 2206 (e.g., for water, sulfur removal) followed by a (bulk) separation unit 2208 such as PSA or membranes that utilize adsorbent materials capable of separation $C_1$ compounds from $C_{2+}$ compounds. These materials can be adsorbents that aid in separation using molecular size differences (e.g., CaX Zeolite, ETS-4). This PSA/membrane can separate the quenched OCM reactor effluent into two streams. The methane rich stream with hydrogen 2210 can be recycled back to OCM via methanation 2212. The $C_{2+}$ compounds 2214 can be fed into an optional acetylene hydrogenation unit 2216 that selectively hydrogenates acetylene to ethylene and ethane. This stream can then be fed to the an olefin/paraffin separation module 2218 containing, for example adsorbents or membranes with pi-complexation materials such as silver ion MOFs, resins such as $Ag^+$ exchanged Amberlyst 15 resin or $M_2$(dobdc) (meta or para form, M can be Mg, Mn, Fe, Co, Ni) MOFs, or any material which can selectively separate olefin from paraffins. A post-$CO_2$ removal unit 2220 can follow. A post $CO_2$ removal unit can reduce the cost since the operation can be performed on a stream with a much lower flow rate. The $CO_2$ removal unit may use liquid absorption or $CO_2$ removal adsorbents in a PSA or TSA or a membrane system. The $CO_2$ stream 2222 can then be recycled into the methanation reactor for further conversion into methane. The $CO_2$-free stream can then be sent into an acetylene removal unit (if acetylene is not hydrogenated prior to olefin/paraffin separation) utilizing materials and adsorbents capable of removing acetylene from ethylene such as UTSA-100, SIFSIX, or ZJU-5 (not shown). Once free from acetylenes, the product stream can go through a final separation unit 2224 to separate ethylene 2226 and propylene 2228. In some cases, some $CO_2$ can be vented 2230 and/or the $C_{2+}$ paraffin stream 2232 can be recycled to (the cracking section of) the OCM reactor 2204.

Figure 23:
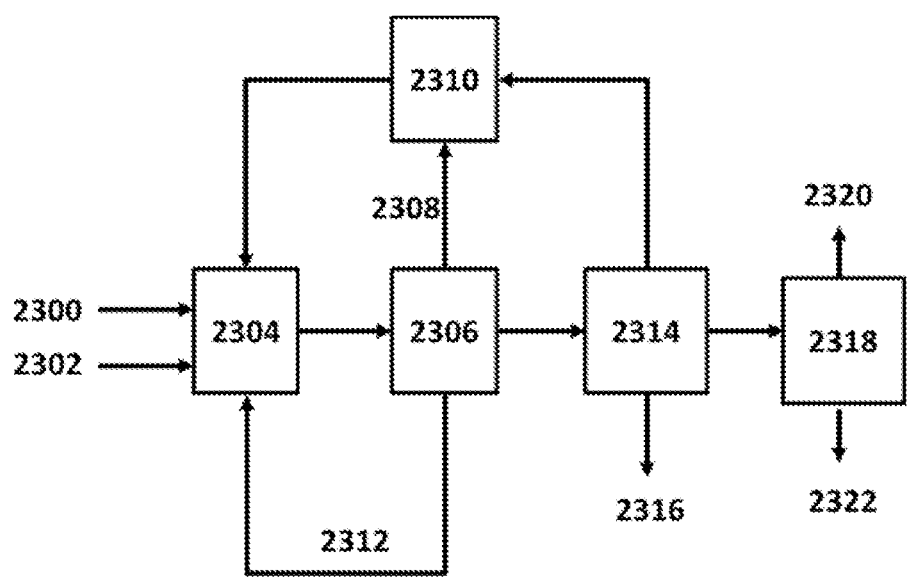
FIG. 23 shows an example of an OCM process scheme employing MOF separations.

FIG. 23 shows another example of an OCM system. In this case, oxygen 2300 and methane 2302 can be fed into an OCM reactor 2304 to produce an OCM effluent. The OCM effluent can, after pre-treatment where necessary (not shown), be sent to an olefin recovery module 2306. The olefin recovery module can contain adsorbent beds in a PSA or TSA system and/or can be a membrane system containing MOFs such as $M_2$(dobdc) (meta or para version, M can be Mg, Mn, Fe, Co, Ni for example) that are by themselves capable of separating the lighter hydrocarbons into individual components or groups thereof (e.g., $CH_4$, $C_2H_4$, $C_2H_6$, $C_2H_2$). In such a system, the effluent from pre-treatment section can be sent into an initial bulk lights removal unit (e.g., PSA with multiple beds for simultaneous adsorption/desorption to run the process continuously and remove methane and lighter components). The desorbed mixture of $C_{2+}$ streams (with lower amounts of $C_1$ and lighter components) can then be separated into ethylene, ethane and acetylene based at least in part on their different elution rates from the adsorbent bed (permeation times if membranes were to be used). Such a configuration can use a $C_{3+}$ removal system (e.g., PSA/membrane based on MOFs) for removing the $C_{3+}$ components prior to the methane removal unit. The separations module can send a stream of $C_1$ molecules and hydrogen 2308 to a methanation unit 2310 and/or can send $C_{2+}$ paraffins 2312 to (the cracking section of) the OCM reactor 2304. A back-end $CO_2$ and acetylene removal unit 2314 can then be utilized to purify olefins stream from $CO_2$ and acetylenes. The $CO_2$ removal unit can include typical $CO_2$ removal liquid absorption columns or PSA/TSA/membranes systems that incorporate $CO_2$ removal adsorbents. Acetylene removal may be performed by adding additional acetylene selective MOF beds such as UTSA-100, SIF SIX, ZJU-5. A back-end purification system can greatly reduce the operating and capital cost of removal units. The $CO_2$ removal unit can send $CO_2$ to methanation 2310 and/or to vent 2316. An olefin separation module 2318 can produce an ethylene stream 2320 and a propylene stream 2322.

In summary, different MOFs can be utilized for their specific selectivities and adsorption capabilities, for example in MMMs or adsorbent beds as PSA systems for hydrocarbon separation of the OCM effluent. MOFs can be very advantageous for their on-purpose synthesis and high surface areas (highest surface area/gram compared to any other material). MOFs in combination with other separation systems (such as polymeric membranes, zeolites, and cryogenic distillation) can be used in novel process schemes to produce OCM product (e.g., ethylene).

Adsorption may be an exothermic phenomenon that releases heat. In some cases, heat of adsorption is the amount of heat released when a unit amount of gas becomes adsorbed on the adsorbent. The heat of adsorption may be approximately equal to the amount of heat required to desorb the same amount of gas. Qualitatively, the greater the heat of adsorption, the more strongly the gas may be adsorbed on the adsorbent, and thus more heat may be required to desorb that gas.

In a PSA, after the adsorption step is complete, desorption of the adsorbed gas may be needed. Desorption can be facilitated by providing sufficient heat of desorption. This can be done by heating the adsorbent bed by various different methods, such as passing a hot purge gas through the bed. Such a mechanism may be referred to as Temperature Swing Adsorption (TSA). TSA may be a relatively slow process (e.g., because of limitation of the rate at which heat can be transported to each adsorption site). As described in the present disclosure, systems and methods are provided whereby the heat of desorption is provided directly at each site by desorbing using a purge gas that itself has high enough adsorption capacity on the adsorbent material such that the heat released by its adsorption can be used as desorption heat for the previously adsorbed feed gas component.

In some cases, the heat of adsorption of the purge gas on the adsorbent material is not equal to the heat of desorption of the feed gas component. Thus the adsorbent bed can either be under-heated (e.g., because of less heat of adsorption of the purge gas than the feed component), or over-heated (e.g., because of high heat of adsorption of the purge gas than the feed component)

The present disclosure provides methods and systems for overcoming such a problem by using a mixture of more than one adsorbent material, such that if one material has a high heat of adsorption for the purge gas, another material may have a low heat of adsorption for the purge gas. The mixture can be prepared homogeneously such that the extra heat released by the purge gas on one component may be readily used by the other material, which otherwise may not release sufficient energy on adsorption of the purge gas. The mixture can be prepared in such a proportion that overall, the heat required by the desorption of the feed gas may be sufficiently matched with adsorption of the purge gas on the mixture of the materials. The match may not need to be substantially precise, since there can be other methods employed at the same time to facilitate desorption, such as pressure swinging, which can have its own contribution on desorption. In some cases, the heat required by the desorption of the feed gas is greater than or equal to about 0.05%, 0.1%, 0.5%, 1%, 5%, 10%, 20%, 30%, 40%, or more of the heat released by the adsorption of the purge gas on the mixture of adsorbent materials. In some cases, the heat required by the desorption of the feed gas is less than or equal to about 40%, 30%, 20%, 15%, 10%, 9%, 8%, 7%, 6%, 5%, 4%, 3%, 2%, 1%, 0.5%, 0.1%, or less of the heat released by the adsorption of the purge gas on the mixture of adsorbent materials. In some cases, the heat required by the desorption of the feed gas is from about 0.01% to about 5%, or from about 0.05% to about 10% of the heat released by the adsorption of the purge gas on the mixture of adsorbent materials. The heat required by the desorption of the feed gas may be within about 0.05%, within about 0.1%, within about 0.5%, within about 1%, within about 5%, or within about 10% of the heat released by the adsorption of the purge gas on the mixture of adsorbent materials.

In some examples, an adsorbent may comprise a first material and a second material that is different from the first material. The first material may adsorb a product gas and/or a sweep gas. The first material may adsorb the product gas at a first heat of adsorption. The first material may adsorb the sweep gas at a second heat of adsorption. The second material may adsorb the product gas and/or the sweep gas. In some cases, the second material adsorbs the product gas and/or the sweep gas at a third heat of adsorption. The first material and the second material may be mixed in a relative proportion, e.g., having a (first material/second material) molar ratio greater than or equal to about 0.001, 0.005, 0.01, 0.05, 0.1, 0.5, 1, 2, 3, 4, 5, 6, 7, 8, 9, 10, 15, 20, 25, 30, 35, 40, 45, 50, 60, 70, 80, 90, 100, 200, 300, 400, 500 or more. The mixed material may have an average heat of adsorption of the sweep gas. The first heat of adsorption, the second heat of adsorption, the third heat of adsorption and the average heat of adsorption may be the same or different. In some cases, one or more of the first heat of adsorption, the second heat of adsorption and the third heat of adsorption have negative values (i.e., heat is released during the adsorption of the product gas and/or the sweep gas). In some cases, there is a difference between the first heat of adsorption and the average heat of adsorption. In some cases, there is a difference between the first heat of adsorption and the second heat of adsorption. In some cases, an absolute value of the difference between the first heat of adsorption and the average heat of adsorption is equal to, greater than or less than an absolute value of the difference between the first heat of adsorption and the second heat of adsorption. In some cases, the absolute value of the difference between the first heat of adsorption and the average heat of adsorption is less than or equal to about 50%, 40%, 30%, 20%, 10%, 5%, 4%, 3%, 2%, 1% or less of the absolute value of the difference between the first heat of adsorption and the second heat of adsorption.

In some cases, the first material adsorbs a product gas at a first heat of adsorption and adsorbs a sweep gas at a second heat of adsorption. In some cases, the second material adsorbs the product gas at a third heat of adsorption and the sweep gas at a fourth heat of adsorption. The first, second, third and fourth heat of adsorption may be the same or different. In some cases, one or more of the first, the second, the third and the fourth heat of adsorption have negative values (i.e., heat is released during the adsorption of the product gas and/or sweep gas). The first material and the second material may be mixed in a relative proportion, e.g., having a (first material/second material) molar ratio greater than or equal to about 0.001, 0.005, 0.01, 0.05, 0.1, 0.5, 1, 2, 3, 4, 5, 6, 7, 8, 9, 10, 15, 20, 25, 30, 35, 40, 45, 50, 60, 70, 80, 90, 100, 200, 300, 400, 500 or more. Such mixed material may have a first average (or mean) heat of adsorption for the product gas. The mixed material may have a second average (or mean) heat of adsorption for the sweep gas. The first average heat of adsorption may be equal to, greater than or less than the second average heat of adsorption. In some cases, the second average heat of adsorption if less than or equal to about 50%, 45%, 40%, 35%, 30%, 25%, 20%, 15%, 10%, 9%, 8%, 7%, 6%, 5%, 4%, 3%, 2%, 1%, or less of the first average heat of adsorption. In some cases, the second average heat of adsorption is substantially equivalent to (e.g., within ±10%, ±5%, or less of) the first average heat of adsorption. In some cases, there is a difference between the first average heat of adsorption and the second average heat of adsorption. In some cases, there is a difference between the first heat of adsorption and the second heat of adsorption. In some cases, an absolute value of the difference between the first average heat of adsorption and the second average heat of adsorption is equal to, greater than or less than an absolute value of the difference between the first heat of adsorption and the second heat of adsorption.

In some cases, the mixture of adsorbent materials comprises two different zeolites and/or MOFs. One of the adsorbent materials can be $M_2(dobdc)$, including para or meta versions of the dobdc and any suitable metal. The mixed adsorbent can have at least about 2, 3, 4, 5, 6, 7, 8, 9, 10, or more different materials. The mixed adsorbent can be intimately mixed, such as having particles of a single material having an average diameter of no more than about 10 micrometers (um), no more than about 50 um, no more than about 100 um, no more than about 500 um, no more than about 1 millimeter (mm), no more than about 5 mm, no more than about 10 mm, no more than about 100 um, or no more than about 500 mm. Adsorbents can be formed materials, which can include mixing powders of the materials (e.g., intimately) adding suitable binders and either tableting or extruding to form the mixed material. Tableted or extruded material can be calcined (e.g., heated) or have other treatments applied to form a robust adsorbent having a suitable crush strength and suitable for being used in a PSA or TSA separation unit.

$CO_2$ Separation

Carbon dioxide ($CO_2$) may be captured from various sources, such as from flue gases, natural gas, or from any process gas rich in $CO_2$. Various processes for post-combustion or pre-combustion capture can be used reduce $CO_2$ emissions. FIGS. 24A-24D illustrate example methods for separating $CO_2$ from a process gas or a flue gas.

Figure 24A:
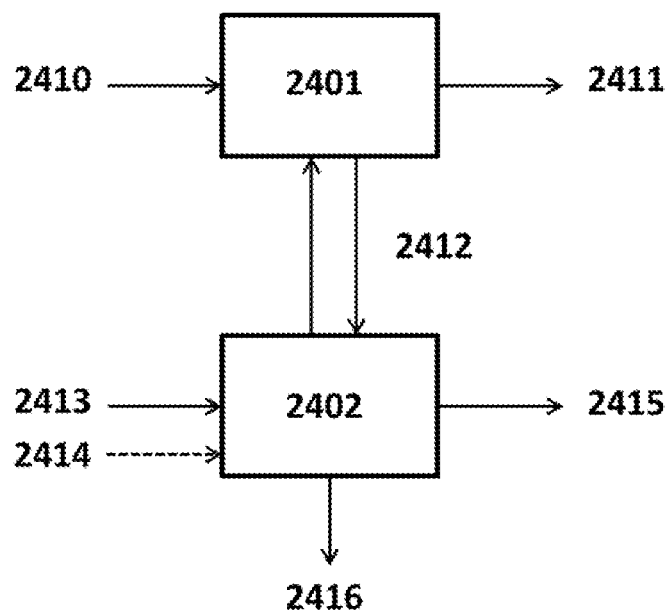
FIG. 24A shows an example of a $CO_2$ separation method of the present disclosure.

In some examples, OCM processes can utilize an amine based absorption system for $CO_2$ removal, which can be followed by use of a caustic scrubber to obtain high degree of separation. The amine system may be prone to corrosion, solvent degradation, and above all, may have high energy requirements. Separations with sorbents and/or solvents can involve placing the $CO_2$ containing gas in intimate contact with a liquid absorbent or a solid sorbent that is capable of capturing the $CO_2$. As shown in FIG. 24A, a stream with $CO_2$ 2410 can be directed into a capture vessel 2401, where it contacts sorbent which captures $CO_2$ from the stream. The stream, with reduced or removed $CO_2$, can then exit 2411 the vessel. Sorbent 2412 loaded with captured $CO_2$ can be transferred to a sorbent regeneration vessel 2402 where it releases the $CO_2$ after being heated (e.g., with the use of energy 2413), after a pressure decrease, or after any other change in the conditions around the sorbent, thereby regenerating the sorbent. Spent sorbent 2415 and $CO_2$ 2416 can be removed from the vessel, and make up sorbent 2414 can be added. After the regeneration step the sorbent can be sent back to capture more $CO_2$ in a cyclic process. The sorbent can be a solid. Solid sorbent can remain in a single vessel rather than being cycled between vessels; sorption and regeneration can be achieved by cyclic changes (e.g., in pressure or temperature) in the vessel where the sorbent is contained. A make-up flow of fresh sorbent can be used to compensate for natural loss of activity and/or sorbent losses.

Amine scrubbing technology can be used to remove acid gases from process gases. Primary amines (e.g., monoethanolamine (MEA), aminoethoxyethanol (DGA)), secondary amines (e.g., diethanolamine (DEA), diisopropanolamine (DIPA)), tertiary (e.g., methyldiethanolamine (MDEA), triethanolamine (TEA)), sterically hindered amines, chilled ammonia, potassium carbonate, and other compounds can be used to remove $CO_2$ from process gases. Traditional amine based systems can be characterized by high energy requirements and solvent degradation. Improved solvents, which can require less energy for regeneration of the solution, include the Benfield process and two stage diethanolamine. Combination with an OCM process can reduce the energy consumption of amine scrubbing processes. Improved solvents can reduce the energy requirements by at least about 10%, 20%, 30%, 40%, 50%, 60%, 70%, 80%, 90%, or more, compared to the traditional MEA solvents. This has the potential of reducing the energy, and hence steam, consumption of the OCM process, thereby increasing the amount of steam available for export from the OCM, or making alternative waste heat recovery methods feasible.

Physical absorption solvents used can include but are not limited to glycol dimethylethers (e.g., Selexol) and propylene carbonate (e.g., IPTS/EC). Regeneration of the solution can be performed by vacuum flashing and air stripping. This approach can consume significantly less energy than in chemical absorption. In using physical solvents $CO_2$ can be released mainly by depressurization, thereby avoiding the high heat of consumption of amine scrubbing processes.

Mixed or hybrid solvents can include but are not limited to sulfinol (sulfolane, water, and amine), such as sulfinol-M and sulfinol-X.

Solid adsorbents, such as zeolites and activated carbon, can be used to separate $CO_2$ from gas mixtures. In pressure swing adsorption (PSA), a gas mixture can flow through a packed bed of adsorbent at elevated pressure until the concentration of the desired gas approaches equilibrium. The bed can be regenerated by reducing the pressure. In temperature swing adsorption (TSA), the adsorbent can be regenerated by raising its temperature. In general usage, adsorption is not yet considered attractive for large scale separation of $CO_2$ because the capacity and $CO_2$ selectivity of available adsorbents are low. However, when the OCM process is a recycle process, an adsorbent based separation method can be used to separate bulk $CO_2$ followed by consuming the remaining $CO_2$ in a methanation reactor system, or by using a caustic scrubber to treat the remaining $CO_2$.

Figure 24B:
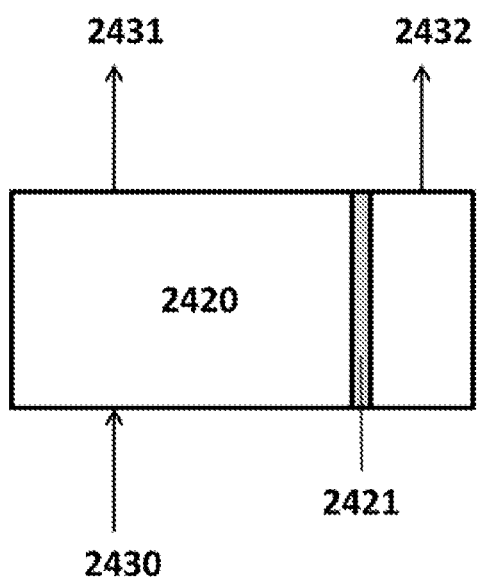
FIG. 24B shows an example of a $CO_2$ separation method of the present disclosure.

Many different types of membrane materials (e.g., polymeric, metallic, ceramic) can be used for $CO_2$ capture to preferentially separate $CO_2$ from a range of process streams. FIG. 24B shows an example schematic of separation of $CO_2$ from a gas stream 2430 in a separation vessel 2420 using a membrane 2421. $CO_2$ can be removed from the stream via the membrane, and $CO_2$ and other gases can exit the vessel in separate streams 2431 and 2432. The main limitation of currently existing membranes is the occurrence of severe plasticization of the membrane in the presence of high pressure $CO_2$. Due to excessive swelling of the polymer membrane upon exposure to $CO_2$, the performance (e.g., selectivity) can decrease significantly, thus reducing the purity of the $CO_2$ and consequently reducing the possibilities for reuse of the gas. Energy requirements can be significantly lower for membrane based technologies. For example, a membrane technology can use 70-75 kilowatthour (kWh) per ton of recovered $CO_2$ compared to significantly higher values for pressure swing adsorption (e.g., 160-180 kWh), cryogenic distillation (e.g., 600-800 kWh), or amine absorption (e.g., 330-340 kWh), making membrane technology an attractive option for integration with OCM for $CO_2$ separation.

Membrane and amine technologies can be combined to form a hybrid process to capture $CO_2$. Micro-porous hollow fiber membranes can be used for $CO_2$ separation using amine-based chemical absorption processes. Micro-porous membranes can be used in a gas-liquid unit where the amine solution is contacted with $CO_2$ containing gas. Use of membrane can lead to a reduction in the physical size and weight of the gas-liquid contacting unit. The separation is based on reversible chemical reaction, and mass transfer occurs by diffusion of the gas through the gas/liquid interface as in traditional contacting columns. Such a hybrid membrane contactor can provide a high contact area between gas and liquid, reduce or essentially eliminate foaming and flooding problems, and give better operational flexibility while reducing solvent degradation problems.

A membrane contactor can combine the advantages of membrane technology and solvent absorption for $CO_2$ separation. A membrane contactor is a combination of advanced membrane techniques with an effective absorption process. A membrane contactor is a hybrid mass exchanger where a porous membrane separates two phases. The selective sorbent performs the separation while the membrane facilitates the mass exchange process by expanding the phase contact surface area. The modified surface properties can improve the selectivity of the process by selectively inhibiting the transport of one of the mixture constituents. Compared to a conventional column device, membranes can allow for up to five times increase in yield per unit volume. Since the sorptive liquid flows within capillaries and both phases are not directly contacting each other, membrane absorbers can operate in any spatial configuration (horizontal or vertical) and at any flux rations between both phases. Also, there is no flooding or uneven packing moisturization. Since the system operates with unchanging yields, independent of the diameter and height; scaling up is fairly simple. Membranes used can be micromembranes or ultrafiltration membranes made up of a variety of different polymer and ceramic materials. Polypropylene fiber membranes can be used to separate $CO_2$ from $CH_4$, for example by using amines like MEA as absorption liquid. Hollow fiber membranes, such as porous polypropylene, perfluoroalkoxy (PFS), and asymmetric poly (phenylene oxide) hollow fiber membranes with a dense ultrathin skin at the outside of the membrane can also be used. In some cases, absorption liquids such as aqueous sarcosine salt solutions, for example in a gas-liquid membrane contactor system, may be used. A membrane contactor can be used to separate the $CO_2$ from the OCM effluent in which $CH_4$ is the major component. Membrane contactors can also be used for separation of olefins and paraffins, and the separation of $CO_2$ from light gases.

An activator, such as piperazine, diethanolamine, and arsenic trioxide, can be used to further enhance the effectiveness of $CO_2$ capture. DGA and tertiary amines may provide more improvement than primary or secondary amines.

Gas selective poly ionic liquid membranes, which are polymerized room temperature ionic liquids (RTIL), can be used to selectively separate $CO_2$. RTILs can be synthesized as a monomer and subsequently polymerized to obtain gas selective membranes. The ionic nature of the polymers can result in tight arrangements between the oppositely charged ionic domains in the poly RTIL, which can prevent the membrane from excessive swelling and deterioration of its performance at elevated pressure and/or temperature. This intrinsic property of poly RTIL can be used to increase the resistance against plasticization and/or to restrict strong swelling of the polymer membrane so as to maintain its permeation properties in the presence of a strong plasticizing agent such as $CO_2$ at higher pressures. For example, an imidazolium-based poly RTIL can be used as base material and the length of the alkyl chain can serve to strengthen or weaken the ionic interactions within the poly RTIL. High pressure mixed $CO_2/CH_4$ gas separation measurements at different temperatures.

Gas components like $CO_2$, from $N_2$ or $CH_4$ can be separated with supported ionic liquid membranes. Ionic liquids are molten salts with a very low melting point (many are liquids at room temperature). Many ionic liquids show a high solubility for carbon dioxide and hence can be highly suitable for use with an OCM process. For example, ionic liquids can include but are not limited to imidazolium, pyrollidinium, pyridinium, cuanidinium, phosphonium, morpholinium, piperidinium, sulfonium, ammonium, hexafluorophosphate, tetraflouroborate, alkylsulphate, triflate, dicyanamide, bis(trifluoromethylsulfonyl)imide, and combinations thereof. Specific advantages of ionic liquids include very low to negligible vapor pressure, good dissolution characteristics for many substances, and lack of flammability or toxicity. Ionic liquids can have good thermal, mechanical and chemical stability as well as favorable densities and viscosities. The required specifications can be adjusted easily by the large number of possible combinations of anions and cations when formulating an ionic liquid. Ionic liquids can be used as chemical solvents, catalysts, electrolytes in fuel cells as well as for gas-separation and storage by absorption. Ionic liquid membrane systems can comprise an adequate porous support material, e.g. a polymer film, coated by ionic liquids. The system can separate $CO_2$ and sulfur compounds from different gas mixtures. Competitive selectivity and permeability are obtained for the separations.

Novel membrane materials, such as polyetherimides, can be used as membrane material with improved plasticization resistance for $CO_2$ removal, for example with an OCM process. Other membrane materials that can be used include, but are not limited to, polymeric membranes based on or comprising polyamides, poly semicarbazides, polycarbonates, polyarylates, polyaniline, poly(phenylen oxide), polysulfones, polypyrrolones, or combinations thereof. In some cases, the polymeric membrane is solvent resistant and can reduce the plasticization effects of hydrocarbons in the feed stream, e.g., polyketone, polyether ketone, polyarylene ether ketone, polyimide, polyetherimide, and/or polyphenylene sulphide, which have intrinsic solvent inertness and can therefore withstand organic rich operation conditions.

An adequate porous support material, e.g. a polymer film, coated by ionic liquids can be used in continuous separation of $CO_2$ and sulfur compounds from different gas mixtures, including a methane rich stream. This separation can improve the efficiency of OCM processes. The OCM reactor effluent can enter the supported ionic liquid separation subsystem, and $CO_2$ and other contaminants can be removed from the process gas. Other contaminants can include but are not limited to traces of sulfur compounds, inerts, CO, $SO_2$, $H_2S$, and tetrahydrothiophene (THT).

Figure 24C:
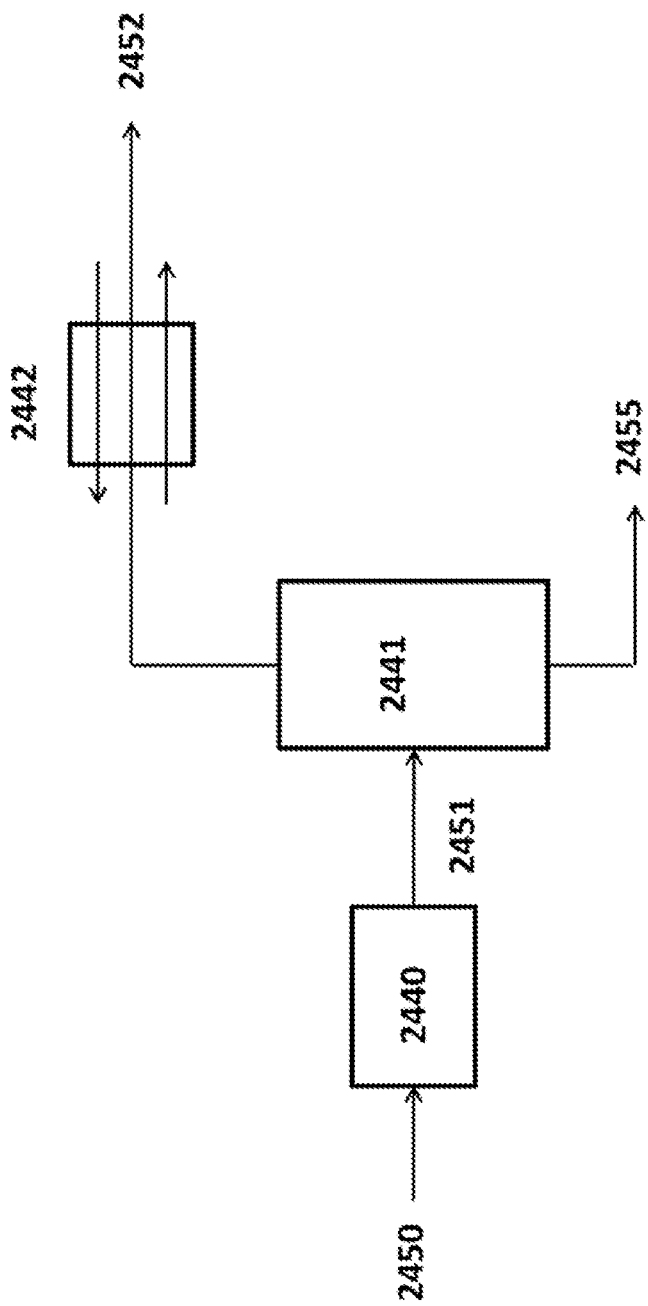
FIG. 24C shows an example of a $CO_2$ separation method of the present disclosure.

$CO_2$ can be separated from other gases by cooling and condensation, for example as shown in FIG. 24C. A stream containing $CO_2$ 2450 can be compressed in a compressor 2440, and the compressed stream 2451 can be directed to a distillation column 2441. Some components can be recovered from the overhead stream 2452, with heat recovered in a heat exchanger 2442. Other components can be recovered from the bottoms 2455. In some cases, cryogenic separation is utilized to separate $CO_2$. Cryogenic separation of $CO_2$ may enable direct production of high purity liquid $CO_2$ that can be used as a feedstock to convert the carbon to higher value hydrocarbons, or otherwise be captured. The amount of energy required can be high, and water may need to be removed before the feed gas is cooled.

In some cases, low temperature distillation is used to separate $CO_2$. Low temperature distillation can give better results when there is a high concentration of $CO_2$ in the feed gas. For the OCM process gas, the $CO_2$ concentration can be increased by, for example, having a recycle stream, or by using a modified OCM reactor where excess $CO_2$ is used as a quench medium for the reaction heat. Low temperature separation can refer to separations using temperature levels above −90° C.

Figure 24D:
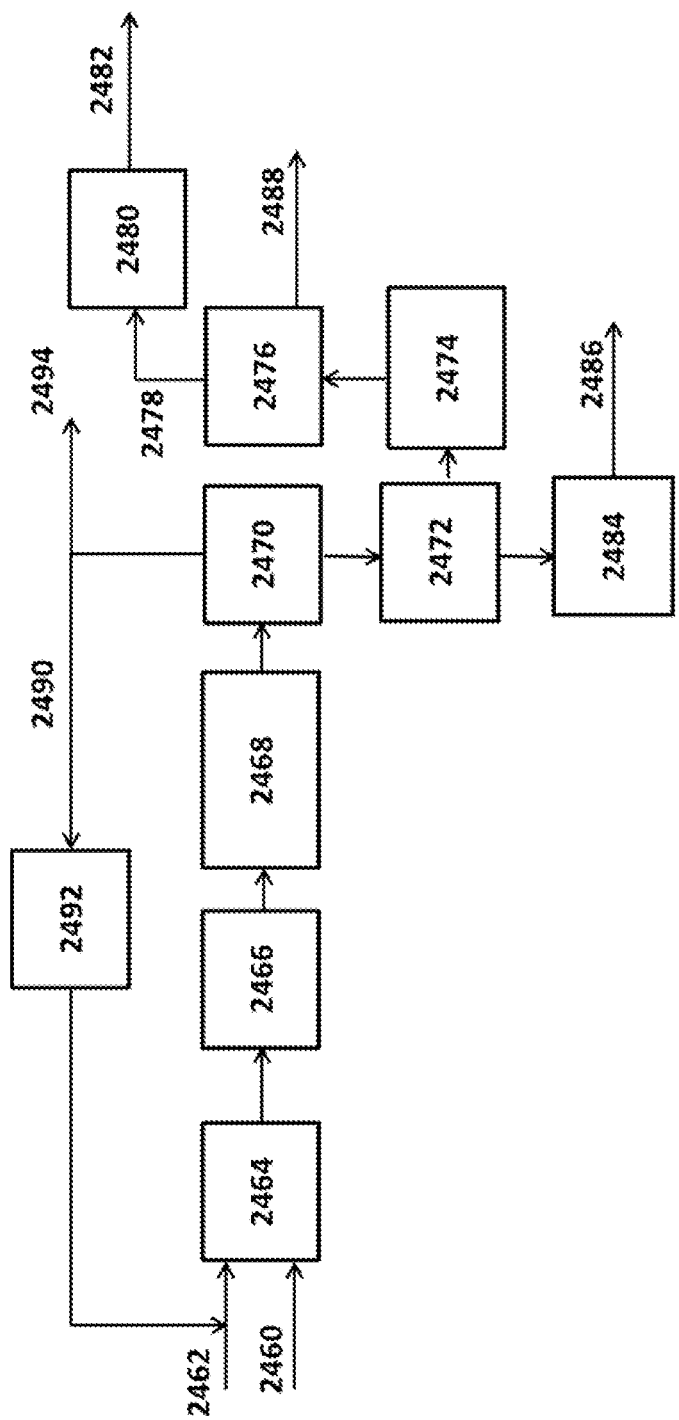
FIG. 24D shows an example of a $CO_2$ separation method of the present disclosure.

As shown in FIG. 24D, another method of the present disclosure for removing $CO_2$ from the OCM system involves a two-step $CO_2$ removal. The first step can be a bulk $CO_2$ removal, followed by the recovery section (e.g., cryogenic fractionation system), and then a second polishing step to remove the $CO_2$ from the purified ethylene product to meet the polymer grade ethylene specifications.

As shown in FIG. 24D, oxygen 2460 can be fed with methane 2462 into an OCM reactor 2464. The effluent can be compressed 2466. The first (bulk) $CO_2$ removal 2468 can be carried out before the cryogenic section. The first $CO_2$ removal lowers the $CO_2$ content to a level tolerable in the cryogenic de-methanizer 2470. The demethanizer is operated at conditions that ensure that no $CO_2$ freezes and all of the residual $CO_2$ that is not removed in the bulk separation 2468 is separated with the heavy $C_{2+}$ stream at the bottom and sent to the de-ethanizer 2472. An acetylene hydrogenation system 2474 and a $C_2$ splitter 2476 can follow the de-ethanizer 2472 to produce high purity ethylene 2478. The high purity ethylene can contain the residual $CO_2$ that is not removed by the first $CO_2$ removal unit 2468. This residual $CO_2$ can be removed by a second $CO_2$ removal step 2480 to produce polymer grade ethylene 2482. In some cases, a depropanizer 2484 can be used to produce a $C_{3+}$ product 2486, ethane 2488 can be recycled to (the cracking section of) the OCM reactor 2464, and $C_1$ compounds 2490 can be methanated 2492 and returned to the OCM reactor 2464 or purged 2494. In some cases $CO_2$ from the first 2468 or second 2480 $CO_2$ removal units can be send to the methanation reactor 2492 (not shown).

The first (bulk) $CO_2$ separations system can be a membrane or a PSA system, an amine removal system, or any other solvent based $CO_2$ removal system as described herein. The final $CO_2$ removal step can be a caustic tower, a membrane based system, a PSA based system, or any other $CO_2$ removal system as described herein. The ethylene product $CO_2$ removal system 2480 can be followed by further drying and/or purification steps.

One advantage of the two step process described herein can be energy saving that arise from decreasing the gas volumes being processed for the final $CO_2$ removal step. If $CO_2$ removal is done entirely upstream of the demethanizer, the energy consumption may be much greater than described in FIG. 24D because the entire methane rich recycle stream dilutes the $CO_2$. When final $CO_2$ removal is performed at the back-end, the ethylene product may have a far lower flow rate and hence the final $CO_2$ removal step is more energy efficient.

The concentration of $CO_2$ going into the de-methanizer (following the first $CO_2$ removal unit) can be any suitable amount (i.e., such that $CO_2$ doesn't freeze in the de-methanizer). In some cases, the concentration of $CO_2$ going into the de-methanizer is greater than or equal to about 0.1 mol %, 0.2 mol %, 0.3 mol %, 0.4 mol %, 0.5 mol %, 0.6 mol %, 0.7 mol %, 0.8 mol %, 0.9 mol %, 1.0 mol %, 1.2 mol %, 1.4 mol %, 1.6 mol %, 1.8 mol %, 2.0 mol %, 2.2 mol %, 2.4 mol %, 2.6 mol %, 2.8 mol %, 3.0 mol %, 3.5 mol %, 4.0 mol %, 5.0 mol %, or more. In some cases, the concentration of $CO_2$ going into the de-methanizer is less than or equal to about 5.0 mol %, 4.0 mol %, 3.5 mol %, 3.0 mol %, 2.8 mol %, 2.6 mol %, 2.4 mol %, at 2.2 mol %, 2.0 mol %, 1.8 mol %, 1.6 mol %, 1.4 mol %, 1.2 mol %, 1.0 mol %, 0.9 mol %, 0.8 mol %, 0.7 mol %, 0.6 mol %, 0.5 mol %, 0.4 mol %, 0.3 mol %, 0.2 mol %, 0.1 mol %, or less. In some cases, the concentration of $CO_2$ going into the de-methanizer is between any of the two values described above, for example, between about 0.5 mol % and about 2.0 mol %.

Figure 25:
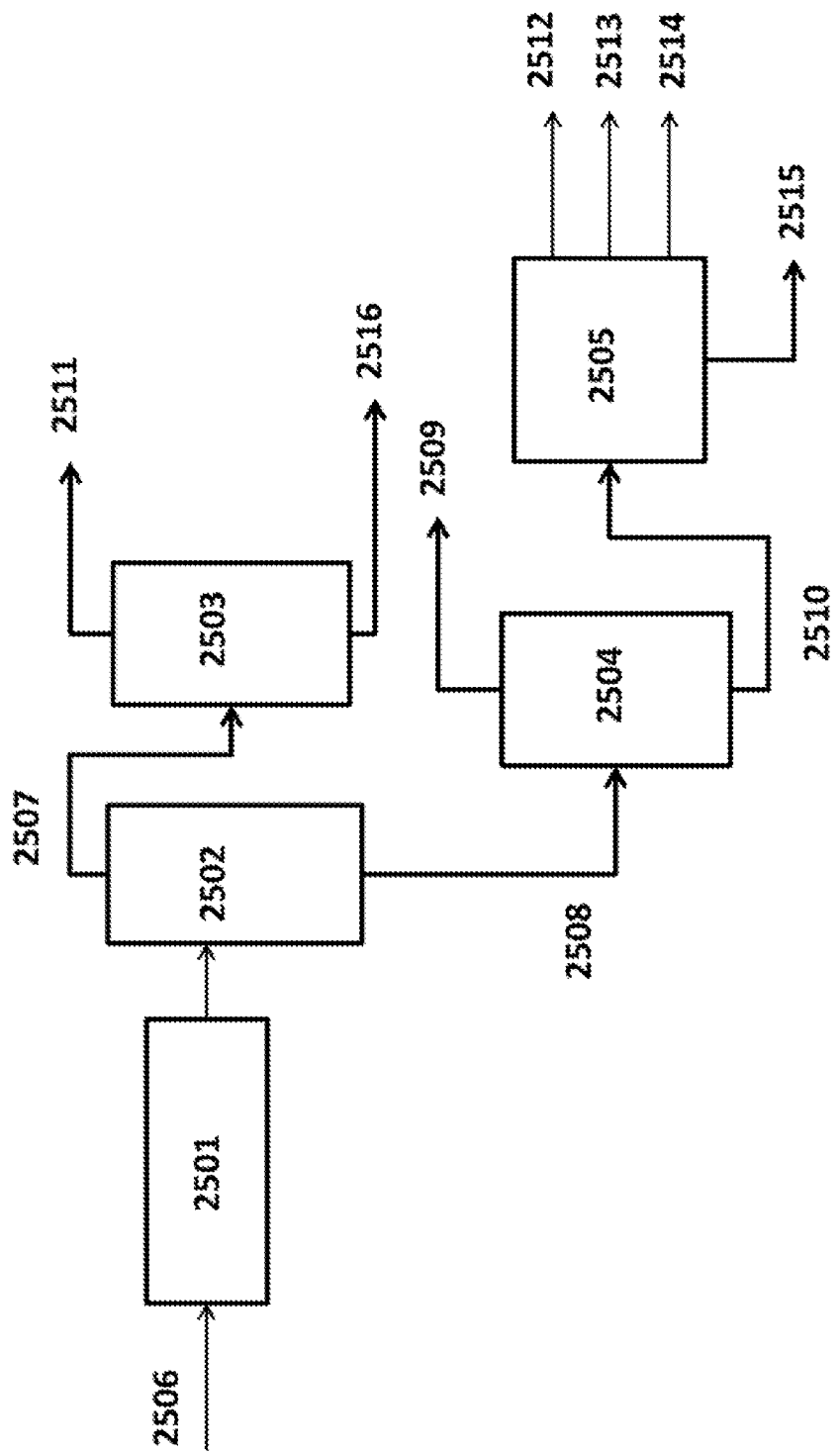
FIG. 25 shows an example $CO_2$ distillation system of the present disclosure.

FIG. 25 shows a schematic of $CO_2$ separation using distillation. OCM reactor effluent 2506 can be fed to a treatment unit 2501, such as a molecular sieve dryer, a sulfur removal bed, or an acetylene removal bed. The treated gas is fed to the first distillation column 2502 that separates the bulk of the methane from the $CO_2$ and other heavier hydrocarbons. Depending on the $CO_2$ concentration in the stream 2506, the bottom stream 2508 may contain at least about 50%, 60%, 70%, 80%, 90%, or more (or any value in between) of the incoming $CO_2$. The overhead from 2507 contains majority of the methane and other light gases and is fed to the column 2503. Column 2503 further recovers methane rich gas 2511, which can be the feed to a methanation system. The bottoms product 2516 may be recycled or sent as a purge to the fuel gas system. The $CO_2$ rich gas 2508 is distilled in the $CO_2$ column 2504 to recover pure $CO_2$ 2509 in the overhead. The bottoms product 2510 can contain some methane along with ethane, ethylene, and other heavier hydrocarbons, and can be sent to recover the ethylene product in a separator 2505. The $CO_2$ product can be sent to methanation unit, and a part of the $CO_2$ can be recycled to achieve the desired concentration of $CO_2$ in the feed stream 2506. Such a $CO_2$ distillation sub system can offer many benefits, including but not limited to reducing the loop size of the OCM process considerably, as the function of the existing cryogenic demethanizer can be reduced by a large extent. Additionally, amine and caustic systems can be replaced by cryogenic or low temperature distillation systems.

Alkaline salt-based processes can be used for $CO_2$ removal. These processes can utilize the alkali salts of various weak acids, such as sodium carbonate and potassium carbonate. These processes can provide advantages such as low cost and minimal solvent degradation. Processes that can be used for $H_2S$ and $CO_2$ absorption include those using aqueous solutions of sodium or potassium compounds. For example, potassium carbonate can absorb $CO_2$ at high temperatures, an advantage over amine-based solvents.

Hot potassium carbonate ($K_2CO_3$) solutions can be used for the removal of $CO_2$ from high-pressure gas streams, among other applications. Potassium carbonate has a low rate of reaction. To improve $CO_2$ absorption, mass transfer promoters such as piperazine, diethanolamine, and arsenic trioxide can be used. Less toxic promoters such as borate can also be used, for example with flue gas streams (see, e.g., Ghosh et al., "Absorption of carbon dioxide into aqueous potassium carbonate promoted by boric acid," Energy Procedia, pages 1075-1081, February 2009, which is hereby incorporated by reference in its entirety). To limit corrosion, inhibitors can be added. These systems can be known as activated hot potassium carbonate systems. Licensed hot activated potassium carbonate systems include the Benfield and the Catacarb process. The processes can be used for bulk $CO_2$ removal from high-pressure streams, but can also produce high-purity $CO_2$.

Flue gas impurities such as SOx and NOx can reduce the operational efficiency of the potassium carbonate as a solvent. $SO_2$ and $NO_2$ may not able to be released from the solvent under industrial conditions. Selective precipitation of the impurity salts formed by SOx and NOx can be used to remove such compounds (see, e.g., Smith et al., "Recent developments in solvent absorption technologies at the CO2CRC in Australia" Energy Procedia, pages 1549-1555, February 2009, which is hereby incorporated by reference in its entirety).

A variety of materials can be used as $CO_2$ sorbents through chemical reactions and physical absorptions, including but not limited to soda-lime, active carbon, zeolites, molecular sieves, alkali metal oxides, silver oxide, lithium oxide, lithium silicate, carbonates, silica gel, alumina, amine solid sorbents, metal organic frameworks and others.

Physical impregnation of $CO_2$-reactive polymers, such as tetraethylene pentamine or polyethyleneimine, inside a porous support, such as alumina, pumice, clay or activated carbon, can be used for $CO_2$ removal. Amine based sorbents can be easily regenerated. Alternatively, a mixture of an amine compound with a polyol compound can be impregnated in a porous support. The polyol compound can be used to increase the $CO_2$ desorption rate of the amine. The supported amine-polyol sorbent can comprise at least about 1 wt %, 5 wt %, 10 wt %, 15 wt %, 20 wt %, 25 wt %, 30 wt %, 35 wt %, or more amine and/or polyol. In some cases, the supported amine-polyol sorbent can comprise from about 1 wt % to about 25 wt % amine and from about 1 wt % to about 25 wt % polyol, with the balance being the support. Solid sorbent can adsorb and desorb $CO_2$ a relatively high rates at ambient temperatures. Enhanced $CO_2$ cyclic removal capacities in either dry or humid air flows can further be achieved by using a solid sorbent at an increased amine concentration of amines from about 35 wt % to about 75 wt %.

Solid sorbents that can selectively remove multiple gases can be used to remove $CO_2$, $H_2O$, nitrogen oxides, and hydrocarbons. This can be achieved by using composite adsorbents, for example by using a mixed adsorbent of alumina and zeolite to remove $CO_2$ and $H_2O$ simultaneously.

$CO_2$ can be separated from flue gas using an ion pump method instead of relying on large temperature and pressure changes to remove $CO_2$ from a solvent. Ion pump methods can substantially increase the overlying vapor pressure of $CO_2$. As a result, the $CO_2$ can be removed from the downstream side of the ion pump as a pure gas. The ion pumping can be obtained from techniques including but not limited to reverse osmosis, electro dialysis, thermal desalination methods, or an ion pump system having an oscillation flow in synchronization with an induced electric field.

By making use of energy such as renewable or nuclear energy, $CO_2$ and water can be recycled into sustainable hydrocarbon fuels in a non-biological process. Various pathways can enable such a conversion, for example by $H_2O$ and $CO_2$ dissociation followed by fuel synthesis. The methods of dissociation can include heat, electricity, and solar driven methods such as thermolysis, thermochemical loops, electrolysis, and photoelectrolysis. High temperature electrolysis can make efficient use of electricity and heat, provide high reaction rates, and integrate well with fuel synthesis.

Synthetic analogues of enzymes as a polymer thin film supported on micro-porous substrates can be used to separate $CO_2$ from gas mixtures. For example, a polymer thin film containing carbonic anhydrase mimicking sites can supported on a porous substrate and can separate $CO_2$ from a stream containing $O_2$ and $N_2$. The system can be, for example, about 30% lower in cost compared to amine-based systems.

$CO_2$ anti-sublimation can be used to remove $CO_2$. $CO_2$ anti-sublimation can use an $SO_2$ removal unit followed by a water cooling step. The water can be eventually removed, for example first as liquid then below the triple point as ice. Dry flue gas can be further cooled until $CO_2$ precipitates. The process can employ anti-sublimating $CO_2$ on a low temperature surface, thus transforming the carbon dioxide from its gaseous phase to a solid phase frosted on a cold surface. Anti-sublimation can allow $CO_2$ capture at a pressure slightly higher than atmospheric. $CO_2$ anti-sublimation can be used with a flue gas system (flue gas composition, e.g., in mol %: $CO_2$ 15%, $H_2O$ 13%, $N_2$ 70% and $O_2$ 3%) at various temperatures (e.g., about 51° C.).

The triple point of $CO_2$ is -56.4° C. and 5.11 atm. For 100% pure $CO_2$ at a pressure P' (where P' is less than 5.11 atm) the frosting temperature can be given by T'=(P'-15.6)*(22.1/4.11). Accordingly, for a pressure of 4.5 atm, T=-59.6° C.

The sublimation temperature of a substance within a gas mixture can depend on its partial pressure (its corresponding concentration within the mixture). Table 1 shows frosting temperatures at different exemplary $CO_2$ concentrations.

TABLE 1

| Frosting temperature versus concentration. | | | | |
| --- | --- | --- | --- | --- |
| Concentration (% v/v) | 100 | 10 | 1 | 0.1 |
| Frosting temperature (° C.) | -78.5 | -103.1 | -121.9 | -136.7 |

For use in an OCM process, a $CO_2$ anti-sublimation unit may encounter higher pressure of OCM effluent (e.g., feed to $CO_2$ capture system), lower $CO_2$ concentration, and higher hydrocarbon content (e.g., methane, ethane, ethylene). Lower $CO_2$ concentration can be addressed by a recycle.

Figure 26:
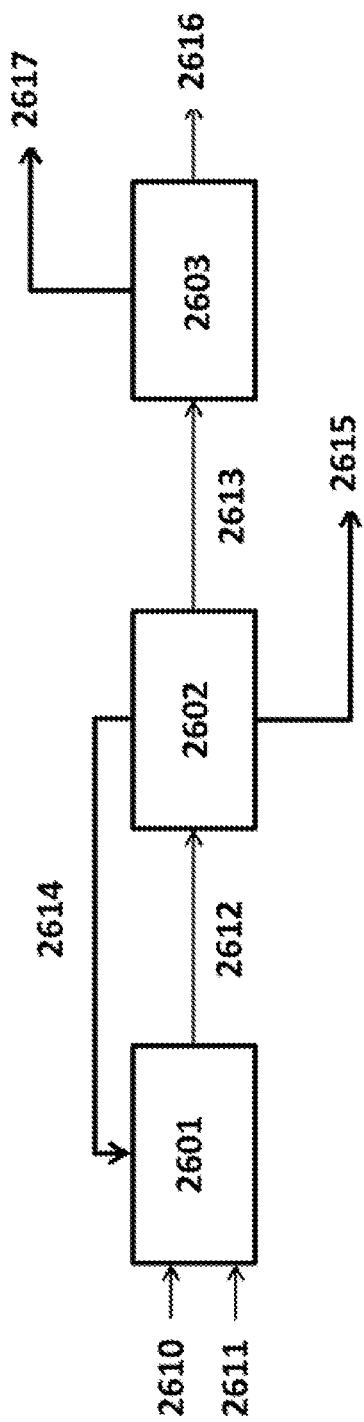
FIG. 26 shows an example OCM system of the present disclosure with $CO_2$ as a quench medium.

The OCM reaction is highly exothermic. Various quenching media can be used to extract the OCM reaction heat. For example, $CO_2$ can be injected to extract the heat, which results in the OCM effluent containing excess $CO_2$. Such effluent can be suitable for the advanced $CO_2$ recovery methods described herein. FIG. 26 shows an exemplary system where $CO_2$ 2614 is removed from an OCM product stream 2612 (generated in an OCM unit 2601 from an oxygen stream 2610 and a methane stream 2611) in a $CO_2$ separation unit 2602 and recycled from back to the OCM reactor 2601. A waste gas or purge stream 2615 can also be removed from the $CO_2$ separation unit. The OCM product stream 2613 can then be separated in a separations unit 2603 into a product stream 2616 comprising ethylene and a purge and/or recycle stream 2617. Separation methods can include low temperature separation, membrane separation, or other separation methods discussed herein. The OCM loop can be decreased to just a $CO_2$ recycle stream. The system can also comprise a methanation unit (not shown).

Such an approach can provide advantages including a smaller recycle loop and more efficient $CO_2$ removal methods, resulting in lower capital expenditure (CAPEX). This can also result in the feasibility of small distributed scale OCM units, since after the removal of excess $CO_2$, the relatively richer ethylene stream needs fewer treatment and recovery steps.

Separation of Air

Production of $O_2$ or $N_2$ may be performed using cryogenic distillation of air which requires liquefaction. In some cases, oxygen condenses at about −183° C. at atmospheric pressure, which makes the cryogenic process very energy intensive. Pressure Swing Adsorption (PSA) systems based on zeolites may be used for air separation to reduce energy consumption in cryogenic processes. However, there is a need for new systems and methods for separating air into $O_2$ and/or $N_2$ fractions at reduced operational (OPEX) and capital (CAPEX) expense, particularly in cases where pure $O_2$ and/or $N_2$ is not required.

In some cases, the systems and methods described herein use materials having much higher surface areas when compared to zeolites (e.g., at least about 2, about 3, about 4, about 5, about 6, about 7, about 8, about 9, about 10, or more fold increase in surface area). Examples of suitable materials include metal organic frameworks (MOFs) such as those described herein. In some cases, these materials exhibit very high selectivity (as compared to zeolites) towards one component (e.g., $O_2$ and/or $N_2$) in a mixture of gases (e.g., air). For example, some $M_2$(dobdc) MOFs have excellent adsorption capacity and selectivity for $O_2$ (e.g., $Fe_2$(dobdc) MOF).

However, it can be very difficult to make a viable process that extracts the desired product at high recovery and purity, especially if the desired component is the one that gets strongly adsorbed on the material (such as, $O_2$ on $Fe_2$(dobdc)). Therefore, provided herein are methods and system configurations that make MOF materials economically viable for air separation by careful choice of purge gas and cycle conditions.

Presented herein are four examples (Cases I-IV) based upon which component is adsorbed and which component is the desired product. In Case I, $O_2$ is preferentially adsorbed on the adsorbent material and $O_2$ is the desired product. In an adsorption phase of a PSA cycle, air can be fed to the adsorbent bed at a pressure such that the partial pressure of $O_2$ falls in a range at which it substantially saturates the bed, thus utilizing the bed's capacity. For example, the $O_2$ partial pressure can be about 0.2 bar in case of $Fe_2$(dobdc) at a temperature of 226K. Note that that the total pressure of the feed air would be greater, since air has approximately 21% $O_2$. Due to the material's high selectivity for $O_2$, $O_2$ gets adsorbed whereas $N_2$ adsorption is much lower, and negligible in some cases. Adsorption can be performed at high feed flow rate, so that the PSA cycle time is very short (for example, less than a minute). Short cycle times can require less of the adsorbent material per ton of $O_2$ produced in a day, thus taking advantage of the high capacity of the adsorbent material. The lighter component stream from the PSA can contain $N_2$ and a portion of the purge gas that replaces $O_2$ (as described below).

Following adsorption for Case I, the system can be depressurized (e.g., for a few seconds) to remove gas from the void spaces of the system. This gas can have a composition similar to air. Desorption can follow depressurization. Since the adsorbed component ($O_2$) is the desired product, the choice of purge gas for desorbing it from the bed can be carefully chosen as described herein. A suitable purge gas may have one or more of the following characteristics: (a) it can readily replace the adsorbed $O_2$, thus resulting in quick desorption of the $O_2$ (i.e., short desorption times can result in a smaller adsorbent bed, thus reducing the amount of adsorbent required); (b) it can be compatible with the downstream process where the $O_2$ is consumed (e.g., if the $O_2$ is to be consumed in an OCM process, $CO_2$, $CH_4$, steam, or any other downstream compatible gas can be used as purge gas); and (c) the lighter gas stream from the adsorption step (e.g., nitrogen) can be used as the purge gas (although the product then would not be ultra-high purity $O_2$, yet the process can be economical in case lower levels of $O_2$ purity is tolerable by the downstream process). In some cases, the purge gas satisfies and two of (a)-(c). In some embodiments, the purge gas satisfies all of (a)-(c).

In some embodiments, the desorption step can be performed at a pressure lower than the adsorption pressure. The bed can then be repressurized with air before the next adsorption step of the cycle.

In Case II, $O_2$ preferentially adsorbs on the adsorbent material and $N_2$ is the desired product. In the adsorption step for Case II, air can be fed to the adsorbent bed at a pressure such that the partial pressure of $O_2$ falls in a range at which it substantially saturates the bed, thus utilizing its capacity. For example, the $O_2$ partial pressure can be around 0.2 bar in case of $Fe_2$(dobdc) at a temperature of 226 K. Note that the total pressure of the feed air would be greater, since air has approximately 21% $O_2$. Due to the high selectivity of the adsorbent, $O_2$ gets adsorbed whereas $N_2$ adsorption in small or insignificant amounts. The lighter component stream from the PSA contains $N_2$ (which is considered to be the product in this Case II) and a portion of the purge gas that replaces $O_2$ (as described below).

Following adsorption for Case II, the system can be depressurized to remove gas from the void spaces of the system. This gas can have a composition similar to air. Desorption can follow depressurization. Since the purge gas replaces $O_2$ on the adsorbent and sweeps the $O_2$ out and the purge gas later gets replaced by $O_2$ during the adsorption step, choice of the purge gas can be crucial as described herein. A suitable purge gas can have one or more (i.e., 1, 2 or 3) of the following characteristics: (a) the purge gas can replace the adsorbed $O_2$ (e.g., $CO_2$), thus resulting in quick desorption of the $O_2$ (i.e., short desorption steps can result in smaller bed having less adsorbent material); (b) the purge gas can be compatible with the downstream process where $N_2$ is being used (i.e., even though the $N_2$ may not be 100% pure due to presence of a portion of purge gas, it is still almost nearly separated from $O_2$); and (c) the lighter gas stream from the adsorption step (e.g., $N_2$ in this case) can be used as the purge gas. The desorption step can be performed at a pressure lower than the adsorption pressure. The bed can be repressurized with air before the adsorption step restarts.

In Case III, $N_2$ preferentially adsorbs on the adsorbent material and $O_2$ is the desired product. In the adsorption step for Case III, air can be fed to the adsorbent bed at a pressure such that the partial pressure of $N_2$ falls in a range at which it substantially saturates the bed, thus utilizing the capacity of the adsorbent material. Note that the total pressure of the feed air would be slightly more because air has approximately 79% $N_2$. Due to the high selectivity of the adsorbent, $N_2$ gets adsorbed whereas $O_2$ adsorption is low or even insignificant. This adsorption step can be performed at high feed flow rate, such that the cycle time is very short (e.g., less than about a minute). The lighter component stream from the PSA contains $O_2$ and a portion of the purge gas that replaces $N_2$ (as described below). The lighter component is considered to be the product in this case.

Following adsorption for Case II, the system can be depressurized (e.g., for few seconds) to remove gas from the void spaces of the whole system. This gas can have a composition similar to air. For desorption, since the purge gas replaces $N_2$ while sweeping it out and itself gets replaced by $N_2$ during the adsorption step, the choice of the purge gas can be crucial as described herein. A suitable purge gas can have one or more (e.g., 1, 2 or 3) of the following characteristics: (a) the purge gas may readily replace the adsorbed $N_2$, thus resulting in quick desorption of the $N_2$; (b) the purge gas can be compatible with the downstream process where $O_2$ is consumed (e.g., if the $O_2$ is to be consumed in an OCM process, $CO_2$, $CH_4$, or steam can be used as purge gas); and (c) the lighter gas stream from the adsorption step (i.e., $O_2$ in this case) can be used as the purge gas. The desorption step can be performed at a pressure lower than the adsorption pressure. The bed can be repressurized with air before the adsorption step restarts.

In Case IV, $N_2$ preferentially adsorbs on the adsorbent material and $N_2$ is the desired product. In adsorption, air can be fed to the adsorbent bed at a pressure such that the partial pressure of $N_2$ falls in a range at which it substantially saturates the bed, thus utilizing its capacity. Note that the total pressure of the feed air would be slightly more, since air has approximately 79% $N_2$. Due to its high selectivity, $N_2$ gets adsorbed whereas $O_2$ adsorption is less, or even insignificant in some cases. This step can be performed at high feed flow rate, such that the cycle time is very short (for example, less than a minute). The lighter component contains $O_2$ and a portion of the purge gas that replaces $N_2$ (as described below). The system can be depressurized for few seconds to remove gas from the void spaces of the system. This gas can have a composition similar to air.

For desorption for Case II, the purge gas replaces $N_2$ while sweeping it out and itself being replaced by $N_2$ during the adsorption step, so choice of the purge gas can be crucial as described herein. A suitable purge gas can have one or more (e.g., 1, 2) of the following characteristics: (a) the purge gas can replace the adsorbed $N_2$ (for example, $CO_2$), thus resulting in quick desorption of the $N_2$; and/or (b) the purge gas can be compatible with the downstream process where $N_2$ is consumed (even though the $N_2$ may not be 100% pure due to presence of a portion of purge gas, it is still almost entirely separated from $O_2$). The desorption step can be performed at a pressure lower than the adsorption pressure. The bed can be repressurized with air before the adsorption step restarts.

In some cases, the feed to the separation system can be the product from either an OCM reactor as discussed above, an OCM process integrated with a Methanol to Olefins (MTO) unit, an OCM process integrated with a steam cracker, or an OCM process integrated with a dimerization and metathesis unit for example.

Methods and systems of the present disclosure can be combined with or modified by other methods and systems, such as those described in U.S. Patent Publication No. 2015/0232395; U.S. Patent Publication No. 2014/0012053; U.S. Patent Publication No. 2014/0018589; U.S. Pat. No. 9,469,577; U.S. Patent Publication No. 2015/0152025; U.S. Patent Publication No. 2015/0210610; and U.S. Pat. No. 9,334,204, each of which is entirely incorporated herein by reference.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for generating compounds with two or more carbon atoms ($C_{2+}$ compounds), comprising:
   (a) directing oxygen ($O_2$) and methane ($CH_4$) into an oxidative coupling of methane (OCM) reactor that reacts the $O_2$ and the $CH_4$ in an OCM process to yield a product stream comprising (i) $C_{2+}$ compounds including olefins and paraffins and (ii) carbon dioxide ($CO_2$); and
   (b) directing the product stream from the OCM reactor into a separations unit that selectively adsorbs the olefins from the paraffins, wherein the separations unit comprises (i) a pressure swing adsorption (PSA) unit, (ii) a temperature swing adsorption (TSA) unit, or (iii) a membrane unit, and wherein the PSA unit, the TSA unit or the membrane unit comprises a sorbent that selectively adsorbs the olefins;
   (c) desorbing the olefins from the sorbent to generate an olefins stream comprising olefins and $CO_2$; and
   (d) directing the olefins stream to a CO2 removal unit to remove CO2 from the olefins stream.

2. The method of claim 1, wherein the separations unit selectively separates ethylene from the paraffins.

3. The method of claim 1, wherein the sorbent has dispersed metal ions that are capable of complexing with the olefins.

4. The method of claim 1, wherein the sorbent is selected from a zeolite, a molecular sieve sorbent, a carbon molecular sieve, an activated carbon, a carbon nanotube, a metal-organic framework (MOF), and a polymeric resin.

5. The method of claim 1, further comprising recycling at least a portion of the $CO_2$ removed from the olefins stream to a methanation unit.

6. The method of claim 1, wherein the sorbent is a MOF, the olefin is ethylene, and the ethylene is desorbed from the MOF using ethane, propane or any combination thereof.

7. A method for generating compounds with two or more carbon atoms ($C_{2+}$ compounds), comprising:

(a) directing oxygen ($O_2$) and methane ($CH_4$) into an oxidative coupling of methane (OCM) reactor that reacts the $O_2$ and $CH_4$ in an OCM process to yield a product stream comprising $C_{2+}$ compounds comprising olefins including ethylene ($C_2H_2$) and propylene ($C_3H_6$) and paraffins including ethane ($C_2H_6$), un-reacted $CH_4$, carbon dioxide ($CO_2$), and hydrogen ($H_2$);

(b) directing the product stream into a first separations unit containing an adsorbent that produces (i) a bottoms stream comprising the $C_{2+}$ compounds and the $CO_2$ and (ii) an overhead stream enriched with the unreacted $CH_4$ and $H_2$, (c) directing the bottoms stream to a second separations unit containing a metal organic framework (MOF) that selectively adsorbs olefins over paraffins;

(d) desorbing olefins from the MOF in the second separations unit to generate a desorbed olefins stream comprising the olefins and the $CO_2$; and (e) directing the desorbed olefins stream to a $CO_2$ removal unit to remove $CO_2$ from the desorbed olefins stream to generate a substantially $CO_2$-free olefins stream.

8. The method of claim 7, further comprising:
directing the overhead stream enriched with the un-reacted $CH_4$ and $H_2$ and at least a portion of the $CO_2$ removed from the desorbed olefins stream to a methanation unit to generate a methane ($CH_4$) stream; and directing the $CH_4$ stream into the OCM reactor.

9. The method of claim 7, further comprising: directing the substantially $CO_2$-free olefins stream to a third separations unit to separate ethylene from propylene.

10. The method of claim 7, wherein the second separations unit comprises a pressure swing absorber (PSA) that contains the MOF.

11. The method of claim 7, wherein the second separations unit comprises a temperature swing absorber (TSA) that contains the MOF.

12. The method of claim 7, wherein the olefins are desorbed from the MOF using ethane, propane or any combination thereof.

13. A method for generating compounds with two or more carbon atoms ($C_{2+}$ compounds), comprising:
(a) directing oxygen ($O_2$) and methane ($CH_4$) into an oxidative coupling of methane (OCM) reactor having a catalytic section and a cracking section to produce an OCM product stream, which catalytic section reacts the $O_2$ and $CH_4$ to yield ethylene ($C_2H_4$), ethane ($C_2H_6$) and heat, which cracking section uses the heat to convert $C_2H_6$ into $C_2H_4$, and wherein the OCM product stream comprises $C_{2+}$ compounds including $C_2H_6$, un-reacted $CH_4$, carbon dioxide ($CO_2$), and hydrogen ($H_2$);

(b) directing the OCM product stream into a first separations unit comprising an adsorbent that produces (i) a first light stream comprising un-reacted $CH_4$, $H_2$, and a first portion of the $CO_2$ and (ii) a first heavy stream comprising $C_2H_4$, $C_2H_6$, and a second portion of the $CO_2$;

(c) directing the first heavy stream to a CO2 removal unit to separate the second portion of the $CO_2$ from the first heavy stream to produce a $CO_2$-free first heavy stream; and (d) directing the $CO_2$-free first heavy stream to a second separations unit comprising a metal organic framework (MOF) to separate the $CO_2$-free first heavy stream into a second light stream comprising $C_2H_6$ and a second heavy stream comprising $C_2H_4$.

14. The method of claim 13, further comprising directing the first light stream and a portion of the second portion of the $CO_2$ to a methanation unit to generate a methane ($CH_4$) stream, and directing the $CH_4$ stream into the catalytic section of the OCM reactor.

15. The method of claim 13, wherein the second separations unit comprises a pressure swing absorber (PSA) or a temperature swing absorber (TSA) that contains the MOF.

16. The method of claim 13, wherein the first separations unit comprises a CaX zeolite and the second separations unit comprises $M_2$(dobdc) MOF.

17. The method of claim 13, further comprising directing a portion of the second light stream to the cracking section of the OCM reactor.

18. The method of claim 13, further comprising directing a purge gas comprising ethane, propane, or combinations thereof to the first separations unit to desorb components of the first heavy stream from the adsorbent, and directing a purge gas comprising ethane, propane, or combinations thereof to the second separations unit to desorb components of the second heavy stream from the MOF.

* * * * *